US012712065B2

(12) United States Patent
Aoyama et al.

(10) Patent No.: US 12,712,065 B2
(45) Date of Patent: Aug. 18, 2026

(54) MEDICAL IMAGE PROCESSING APPARATUS, METHOD, AND MEDICAL SYSTEM

(71) Applicant: Canon Kabushiki Kaisha, Tokyo (JP)

(72) Inventors: Gakuto Aoyama, Otawara (JP); Takuya Sakaguchi, Utsunomiya (JP); Yufei Li, Beijing (CN); Qi Zhu, Beijing (CN); Changsheng Qu, Beijing (CN); Yongjun Ma, Beijing (CN)

(73) Assignee: Canon Kabushiki Kaisha, Tokyo (JP)

( * ) Notice: Subject to any disclaimer, the term of this patent is extended or adjusted under 35 U.S.C. 154(b) by 366 days.

(21) Appl. No.: 18/326,415

(22) Filed: May 31, 2023

(65) Prior Publication Data

US 2023/0386647 A1 Nov. 30, 2023

(30) Foreign Application Priority Data

May 31, 2022 (CN) ......................... 202210607591.3
Jun. 20, 2022 (JP) ................................. 2022-099083

(51) Int. Cl.
*G16H 30/40* (2018.01)
*A61B 6/03* (2006.01)
*G06T 7/00* (2017.01)
*G16H 30/20* (2018.01)

(52) U.S. Cl.
CPC ........... *G16H 30/40* (2018.01); *G06T 7/0012* (2013.01); *G16H 30/20* (2018.01); *A61B 6/032* (2013.01)

(58) Field of Classification Search
CPC ........ G16H 30/40; G16H 50/20; G16H 50/70; G16H 30/20; G06T 7/0012; G06T 7/60; G06T 2207/20084; G06T 2207/20104; G06T 5/92; G06T 7/33; G06T 2207/30004; A61B 6/469; A61B 6/5217; A61B 5/7271; A61B 6/032
See application file for complete search history.

(56) References Cited

U.S. PATENT DOCUMENTS

| | | | | |
|---|---|---|---|---|
| 10,229,498 | B2 * | 3/2019 | Kitamura | A61B 1/041 |
| 10,779,786 | B2 * | 9/2020 | Sakaguchi | A61B 6/504 |
| 2022/0164951 | A1 | 5/2022 | Chui et al. | |

FOREIGN PATENT DOCUMENTS

| | | | | |
|---|---|---|---|---|
| CN | 108491770 A | | 9/2018 | |
| JP | 2020-171475 A | | 10/2020 | |
| WO | WO-2018133118 A1 | * | 7/2018 | G16H 30/40 |

OTHER PUBLICATIONS

Machine translation obtained from google patents of WO-2018133118-A1 (Year: 2018).*
Combined Chinese Office Action and Search Report issued Dec. 3, 2025 in Chinese Patent Application No. 202210607591.3, 6 pages.
(Continued)

*Primary Examiner* — Courtney Joan Nelson
(74) *Attorney, Agent, or Firm* — Oblon, McClelland, Maier & Neustadt, L.L.P.

(57) ABSTRACT

A medical image processing apparatus according to an embodiment includes processing circuitry and storage circuitry. The processing circuitry acquires a medical image. The processing circuitry extracts a region of interest from the medical image. The processing circuitry sets a calculation rule for calculating a characteristic amount for the region of interest. The storage circuitry stores therein the calculation rule.

11 Claims, 40 Drawing Sheets

(56) References Cited

OTHER PUBLICATIONS

Office Action issued Mar. 25, 2026, in corresponding Japanese Patent Application No. 2022-099083, citing document 1 herein, 6 pages.
Office Action issued Apr. 2, 2026, in corresponding Chinese Patent Application No. 202210607591.3, with English translation, 12 pages.

* cited by examiner

Point Name:

Grid point

Quantile of line

Quantile of open curve

Center of gravity

Farthest or nearest point

Intersection point

Quantile: 2 ~1122

Please select the line:

~1121

Antero-Posterior line

Inter-commissural line

Custom line1

Open Curve Name:

User input
b/w plane to surface
b/w surface to surface
Shortest distance
Projection Input at least 3 points type: Curve 1301

Anterolateral Commissure
Posteromedial Commissure
Posteromedial Trigone
Anterolateral Trigone
Midpoint of two trigone

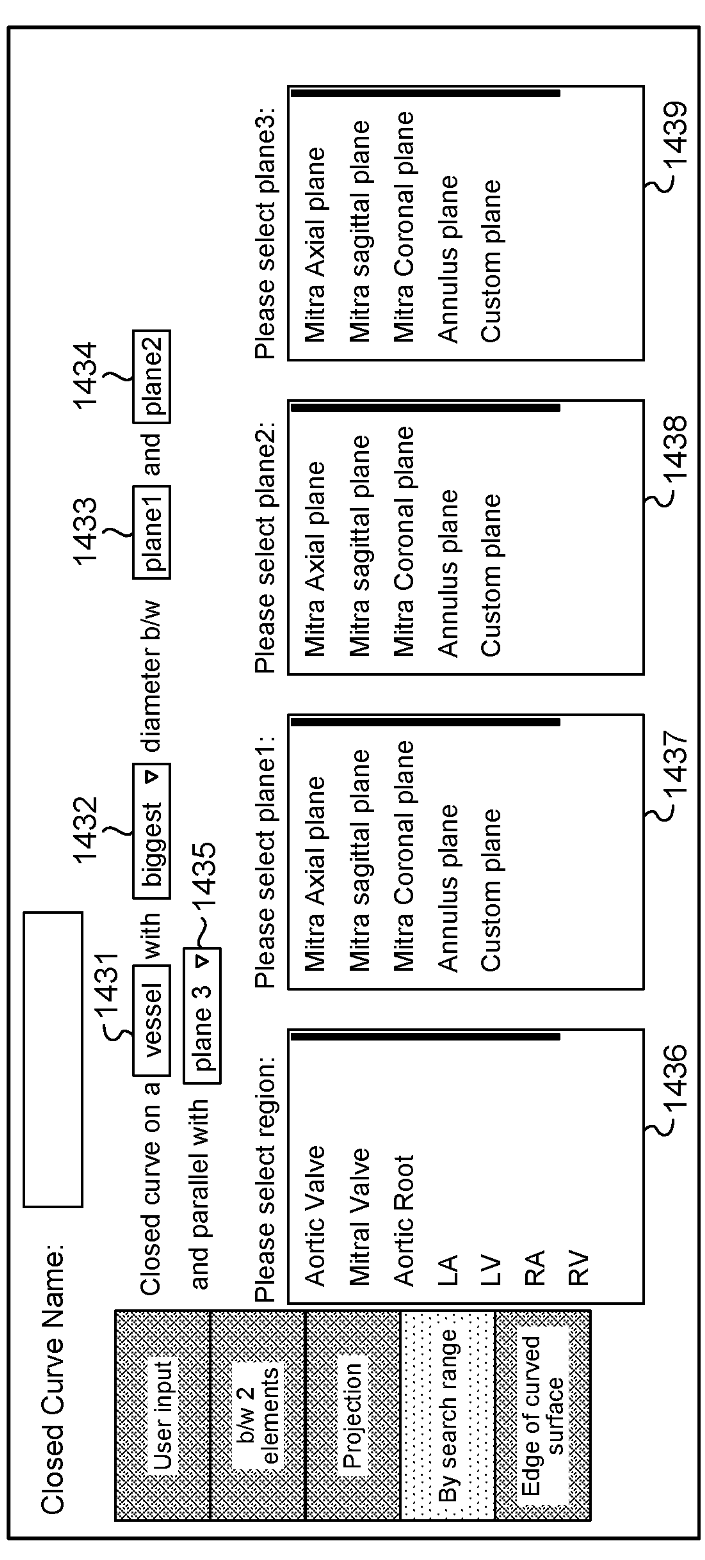
FIG.14E
Closed Curve Name:
Closed curve on a
vessel
1431
with
biggest
1432
diameter b/w
plane1
1433
and
plane2
1434
and parallel with
plane 3
1435
User input
b/w 2 elements
Projection
By search range
Edge of curved surface
Please select region:
Aortic Valve
Mitral Valve
Aortic Root
LA
LV
RA
RV
1436
Please select plane1:
Mitra Axial plane
Mitra sagittal plane
Mitra Coronal plane
Annulus plane
Custom plane
1437
Please select plane2:
Mitra Axial plane
Mitra sagittal plane
Mitra Coronal plane
Annulus plane
Custom plane
1438
Please select plane3:
Mitra Axial plane
Mitra sagittal plane
Mitra Coronal plane
Annulus plane
Custom plane
1439

Closed Curve Name:

User input b/w plane to surface

Projection

By search range

Edge of curved surface

Edge of user specified curved surface 1451

Please select curved surface:

Anterior leaflet

Posterior leaflet

Custom surface 1

Figure 24:
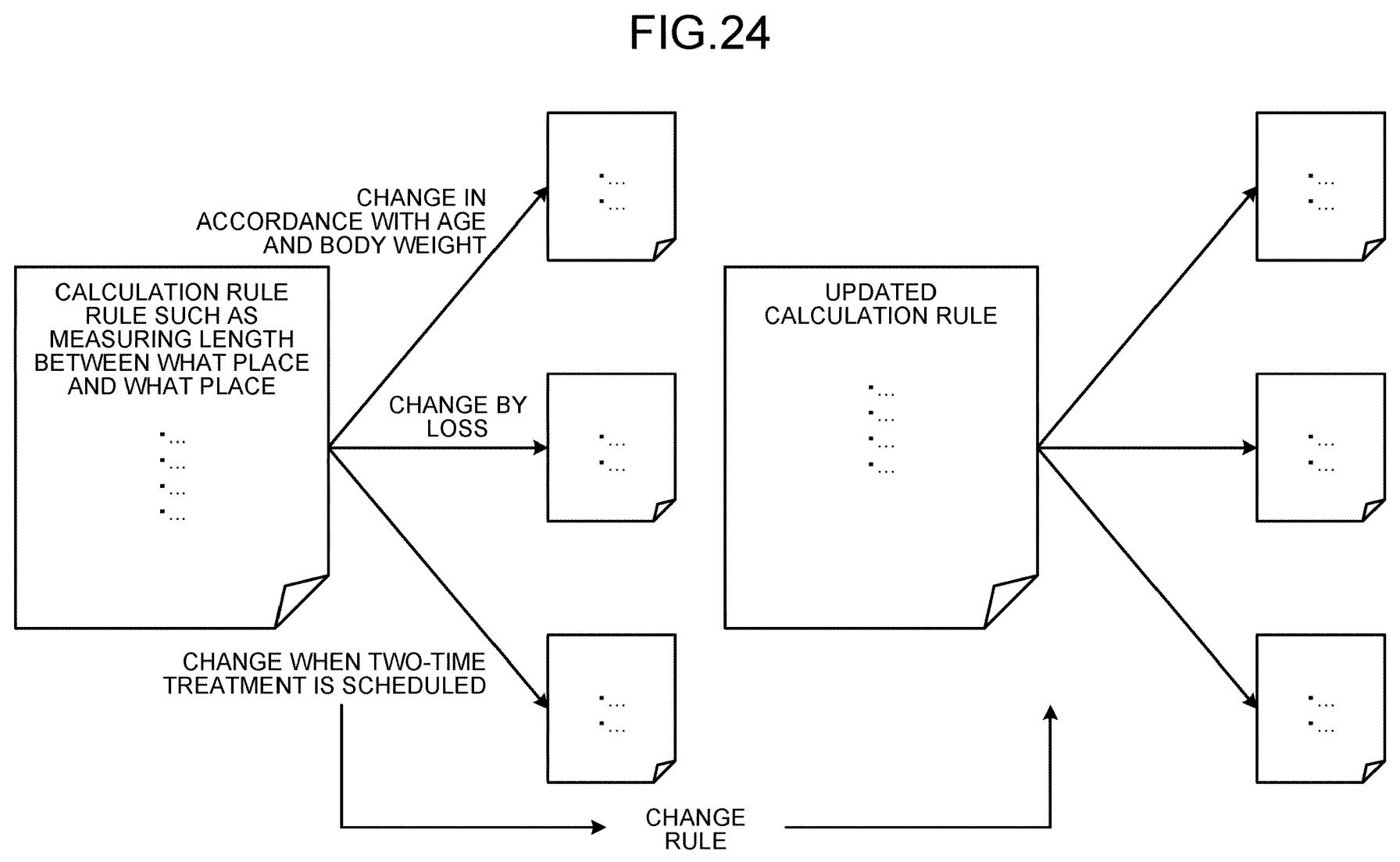

CALCULATION RULE
RULE SUCH AS
MEASURING LENGTH
BETWEEN WHAT PLACE
AND WHAT PLACE

CHANGE IN
ACCORDANCE WITH AGE
AND BODY WEIGHT

CHANGE BY
LOSS

CHANGE WHEN TWO-TIME
TREATMENT IS SCHEDULED

CHANGE
RULE

UPDATED
CALCULATION RULE

・DISTRIBUTE MONTHLY
・FREELY DOWNLOAD DURING CONTRACT PERIOD

・PROVIDE NOTIFICATION OF NUMBER OF TIMES USED USING CALCULATION RULE (NUMBER OF PATIENTS AND NUMBER OF TIMES USED)
・UPLOAD DEFINITION FILE CREATED BY MEDICAL INSTITUTION

・AUTHENTICATE UPLOADED FILE

MEDICAL IMAGE PROCESSING APPARATUS, METHOD, AND MEDICAL SYSTEM

CROSS-REFERENCE TO RELATED APPLICATIONS

This application is based upon and claims the benefit of priority from Chinese Patent Application No. 202210607591.3, filed on May 31, 2022; and Japanese Patent Application No. 2022-099083, filed on Jun. 20, 2022, the entire contents of all of which are incorporated herein by reference.

FIELD

Embodiments described herein relate generally to a medical image processing apparatus, a method, and a medical system.

BACKGROUND

In the medical field, various methods of treatment are being developed day to day. For the various methods of treatment, to determine the applicability of the methods of treatment, to select an appropriate method of treatment from a plurality of methods of treatment, and to make a specific treatment plan using the selected method of treatment, it is important to have an appropriate understanding of a treatment target or an anatomical structure involved in the treatment target. For example, to assist in having an understanding of the anatomical structure, there are known techniques that automatically (or semi-automatically) acquire information on a target anatomical structure from medical images.

These techniques acquire a region of the target anatomical structure (hereinafter, a "region of interest") from the medical image and calculate measured values for preset measurement items registered in a product based on the region of interest. However, these techniques calculate the measured values for the preset measurement items, and thus when a new method of treatment is developed and a measured value of a new measurement item is needed, these techniques cannot automatically calculate the measured value for the new measurement item.

BRIEF DESCRIPTION OF THE DRAWINGS

FIG. 11C is a diagram of an example of the GUI setting the Element of "Point" according to the first embodiment;

FIG. 11D is a diagram of an example of the GUI setting the Element of "Point" according to the first embodiment;

FIG. 14A is a diagram of an example of a GUI setting the Element of "Closed Curve" according to the first embodiment;

FIG. 14B is a diagram of an example of the GUI setting the Element of "Closed Curve" according to the first embodiment;

FIG. 14E is a diagram of an example of the GUI setting the Element of "Closed Curve" according to the first embodiment;

FIG. 24 is a diagram for illustrating an example of a change of the calculation rule according to the second embodiment;

DETAILED DESCRIPTION

A medical image processing apparatus according to an embodiment includes processing circuitry and storage circuitry. The processing circuitry is configured to acquire a medical image. The processing circuitry is configured to extract a region of interest from the medical image. The processing circuitry is configured to set a calculation rule for calculating a characteristic amount for the region of interest. The storage circuitry is configured to store therein the calculation rule.

The following describes embodiments of a medical image processing apparatus, a method, a non-transitory computer readable medium, and a medical system in detail with reference to the accompanying drawings. The medical image processing apparatus, the method, the non-transitory computer readable medium, and the medical system according to the present application are not limited by the embodiments shown below. In the following description, similar components are denoted by common symbols, and duplicate descriptions are omitted.

First Embodiment

Figure 1:
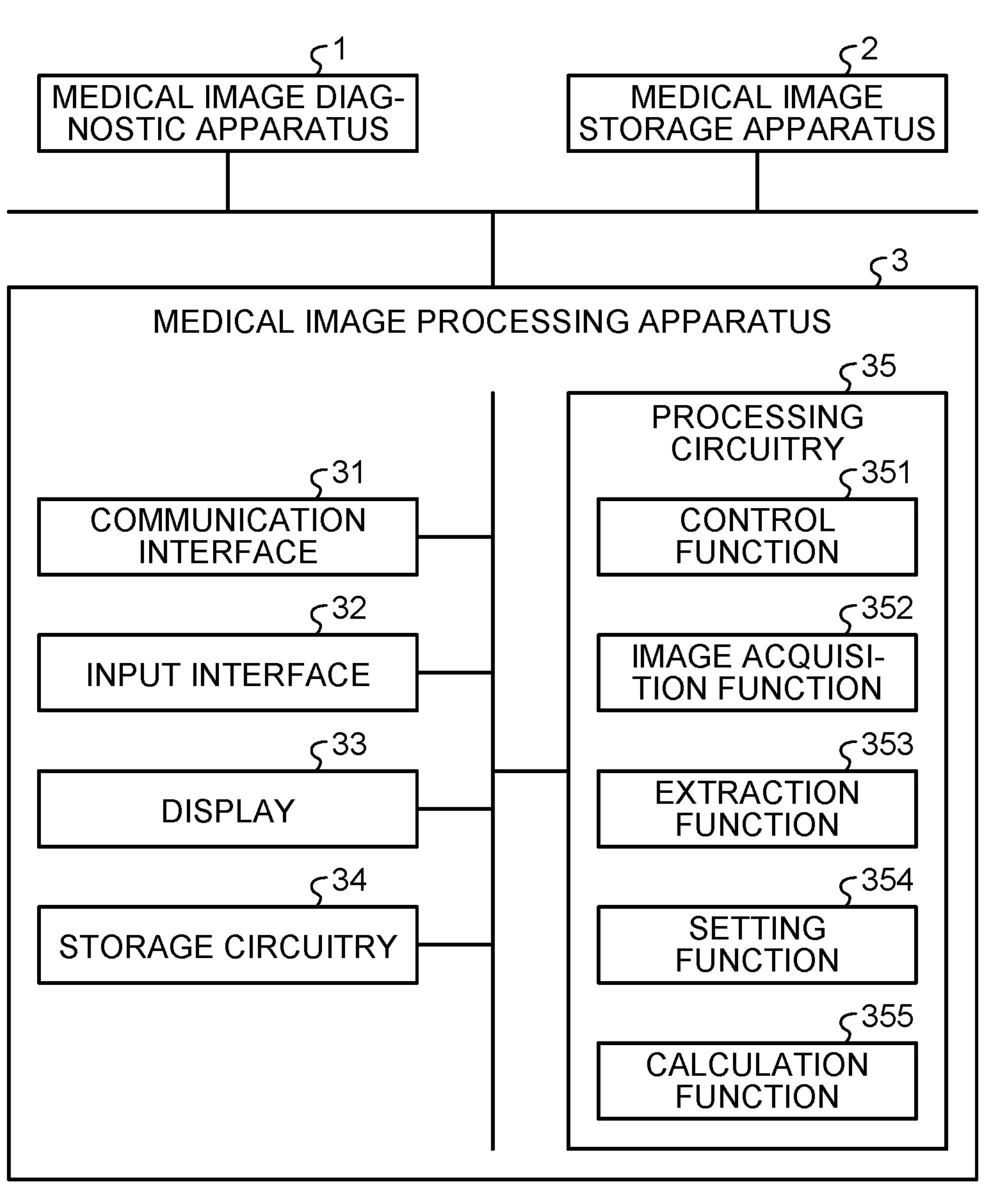
FIG. 1 is a diagram of a configuration example of a medical image processing apparatus according to a first embodiment.

FIG. 1 is a diagram of a configuration example of a medical image processing apparatus according to a first embodiment. For example, as illustrated in FIG. 1, this medical image processing apparatus 3 according to the present embodiment is communicably connected to a medical image diagnostic apparatus 1 and a medical image storage apparatus 2 via a network. Various other apparatuses and systems may be connected to the network illustrated in FIG. 1.

The medical image diagnostic apparatus 1 takes an image of a subject to generate a medical image. The medical image diagnostic apparatus 1 then transmits the generated medical image to various apparatuses on the network. For example, the medical image diagnostic apparatus 1 is an X-ray diagnostic apparatus, an X-ray computed tomography (CT) apparatus, a magnetic resonance imaging (MRI) apparatus, an ultrasound diagnostic apparatus, a single photon emission computed tomography (SPECT) apparatus, or a positron emission computed tomography (PET) apparatus.

The medical image storage apparatus 2 stores therein various medical images for the subject. Specifically, the medical image storage apparatus 2 receives the medical image from the medical image diagnostic apparatus 1 via the network and stores and keeps the medical image in its own internal storage circuitry. For example, the medical image storage apparatus 2 is implemented by a computer device such as a server or a workstation. For example, the medical image storage apparatus 2 is implemented by Picture Archiving and Communication System (PACS) or the like and keeps the medical image in a format compliant with Digital Imaging and Communications in Medicine (DICOM).

The medical image processing apparatus 3 performs various processing for the medical image of the subject. Specifically, the medical image processing apparatus 3 receives the medical image from the medical image diagnostic apparatus 1 or the medical image storage apparatus 2 via the network and performs various information processing using the medical image. For example, the medical image processing apparatus 3 is implemented by a computer device such as a server or a workstation.

For example, the medical image processing apparatus 3 includes a communication interface 31, an input interface 32, a display 33, storage circuitry 34, and processing circuitry 35.

The communication interface 31 controls transmission and communication of various data transmitted and received between the medical image processing apparatus 3 and other apparatuses connected via the network. Specifically, the communication interface 31 is connected to the processing circuitry 35 and transmits data received from other apparatuses to the processing circuitry 35 or transmits data received from the processing circuitry 35 to other apparatuses. For example, the communication interface 31 is implemented by a network card, a network adapter, or a network interface controller (NIC).

The input interface 32 receives input operations of various instructions and various information from a user. Specifically, the input interface 32 is connected to the processing circuitry 35 and converts an input operation received from the user into an electric signal and transmits it to the processing circuitry 35. For example, the input interface 32 is implemented by a trackball, a switch button, a mouse, a keyboard, a touchpad performing input operations through touching on an operating surface, a touchscreen with a display screen and a touchpad integrated, a noncontact input interface including an optical sensor, or a voice input interface. In the present specification, the input interface 32 is not limited to those including physical operating components such as a mouse or a keyboard. Examples of the input interface 32 include electric signal processing circuitry receiving an electric signal corresponding to an input operation from an external input device provided separately from the apparatus and transmitting this electric signal to control circuitry.

The display 33 displays various information and various data. Specifically, the display 33 is connected to the processing circuitry 35 and displays various information and various data received from the processing circuitry 35. For example, the display 33 is implemented by a liquid crystal display, a cathode ray tube (CRT) display, a touch panel, or the like.

The storage circuitry 34 stores therein various data and various computer programs. Specifically, the storage circuitry 34 is connected to the processing circuitry 35 and stores therein data received from the processing circuitry 35 or reads stored data and transmit it to the processing circuitry 35. For example, the storage circuitry 34 is implemented by a semiconductor memory element such as a random access memory (RAM) or a flash memory, a hard disk, an optical disc, or the like.

The processing circuitry 35 controls the entire medical image processing apparatus 3. For example, the processing circuitry 35 performs various processing in response to input operations received from the user via the input interface 32. For example, the processing circuitry 35 receives data transmitted from other apparatuses via the communication interface 31 and stores the received data in the storage circuitry 34. For example, the processing circuitry 35 transmits the data received from the storage circuitry 34 to the communication interface 31 to transmit the data to other apparatuses. For example, the processing circuitry 35 displays the data received from the storage circuitry 34 on the display 33.

A configuration example of the medical image processing apparatus 3 according to the present embodiment has been described so far. For example, the medical image processing apparatus 3 according to the present embodiment is installed in medical institutions such as hospitals and clinics to support various diagnoses, the formulation of treatment plans, and the like performed by users such as doctors. For example, the medical image processing apparatus 3 performs various processing to easily calculate a measured value of a new measurement item for a region of interest. The following describes the medical image processing apparatus 3 in detail.

For example, as illustrated in FIG. 1, in the present embodiment, the processing circuitry 35 of the medical image processing apparatus 3 executes a control function 351, an image acquisition function 352, an extraction function 353, a setting function 354, and a calculation function 355. The processing circuitry 35 is an example of processing circuitry.

The control function 351 performs control to generate various graphical user interfaces (GUIs) and various display information and to display them on the display 33 in response to operations via the input interface 32. For example, the control function 351 causes the display 33 to display a GUI for setting a measurement item for the region of interest and morphological information of the region of interest. The processing by the control function 351 will be described in detail below.

The image acquisition function 352 acquires a medical image of the subject from the medical image diagnostic apparatus 1 or the medical image storage apparatus 2 via the communication interface 31. Specifically, the image acquisition function 352 acquires volume data including the region of interest (heart valves, for example). The image acquisition function 352 can also acquire a plurality of pieces of volume data obtained by taking a plurality of images in a time direction in three dimensions. For example, the image acquisition function 352 acquires CT images, ultrasound images, MRI images, X-ray images, Angio images, PET images, SPECT images, or the like as the volume data described above. The processing circuitry 35 executes the image acquisition function 352 described above to receive the medical image of the subject from the medical image diagnostic apparatus 1 or the medical image storage apparatus 2 and to store the received medical image in the storage circuitry 34.

The extraction function 353 extracts the region of interest from the medical image. Specifically, the extraction function 353 extracts the region of interest in the volume data acquired by the image acquisition function 352. The processing by the extraction function 353 will be described in detail below.

The setting function 354 sets a calculation rule for calculating a characteristic amount for the region of interest. Specifically, the setting function 354 sets a rule for extracting anatomical information of the region of interest as the calculation rule for calculating the characteristic amount. The storage circuitry 34 stores therein the calculation rule set by the setting function 354. The processing by the setting function 354 will be described in detail below.

The calculation function 355 calculates the characteristic amount of the region of interest based on the calculation rule. The processing by the calculation function 355 will be described in detail below.

The processing circuitry 35 described above is implemented by a processor, for example. In that case, each processing function described above is stored in the storage circuitry 34 in the form of a computer program that can be executed by a computer. The processing circuitry 35 reads each computer program stored in the storage circuitry 34 and executes it to implement the function corresponding to each computer program. In other words, the processing circuitry 35, which has read each computer program, has each processing function illustrated in FIG. 1.

The processing circuitry 35 may be configured by combining a plurality of independent processors, and each of the processors may execute the computer program to implement each processing function. Each processing function of the processing circuitry 35 may be implemented by being distributed or integrated into a single circuit or a plurality of processing circuitries as appropriate. Each processing function of the processing circuitry 35 may be implemented by a combination of hardware such as circuits and software. An example of a case in which the computer program corresponding to each processing function is stored in the single storage circuitry 34 has been described, but the embodiment is not limited to this example. For example, a computer program corresponding to each processing function may be stored in a plurality of storage circuits in a distributed manner, and the processing circuitry 35 may read each computer program from each storage circuitry and execute it.

Figure 2:
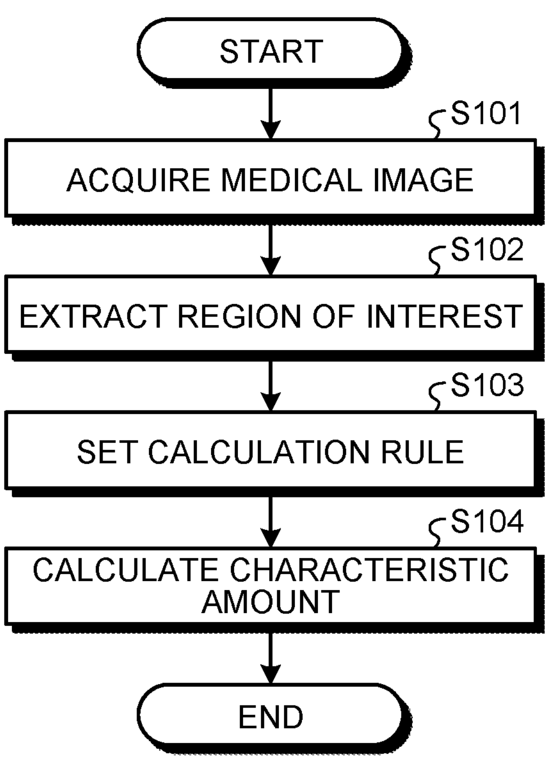
FIG. 2 is a flowchart of a processing procedure of processing performed by processing functions of processing circuitry of the medical image processing apparatus according to the first embodiment.

The following describes a procedure of processing by the medical image processing apparatus 3 with reference to FIG. 2 and then describes the details of each processing. FIG. 2 is a flowchart of a processing procedure of processing performed by each processing function of the processing circuitry 35 of the medical image processing apparatus 3 according to the first embodiment.

For example, as illustrated in FIG. 2, in the present embodiment, the image acquisition function 352 acquires a medical image (volume data) of the subject from the medical image diagnostic apparatus 1 or the medical image storage apparatus 2 (Step S101). For example, the image acquisition function 352 acquires volume data including morphological information of an anatomical structure of the region of interest in response to a volume data acquisition operation via the input interface 32. This processing is implemented by the processing circuitry 35 calling the computer program corresponding to the image acquisition function 352 from the storage circuitry 34 and executing it, for example.

Subsequently, the extraction function 353 extracts the region of interest (a heart valve, for example) contained in the medical image for the acquired volume data (Step S102). This processing is implemented by the processing circuitry 35 calling the computer program corresponding to the extraction function 353 from the storage circuitry 34 and executing it, for example.

Then, the setting function 354 sets the calculation rule for calculating the characteristic amount in the region of interest (Step S103). This processing is implemented by the processing circuitry 35 calling the computer program corresponding to the setting function 354 from the storage circuitry 34 and executing it, for example.

Subsequently, the calculation function 355 calculates the characteristic amount in the region of interest based on the set calculation rule (Step S104). This processing is implemented by the processing circuitry 35 calling the computer program corresponding to the calculation function 355 from the storage circuitry 34 and executing it, for example.

The following describes the details of each processing executed by the medical image processing apparatus 3. The following describes processing in a case in which the mitral valve is used as the region of interest as an example, but the target to be processed described in the present embodiment is not limited to this example, and various other regions of interest can be used as the target. The following describes a case in which a CT image is used as the medical image, but the target to be processed described in the present embodiment is not limited to this example, and various other medical images can be used as the target. Acquisition Processing for Medical Image.

As described at Step S101 in FIG. 2, the image acquisition function 352 acquires the volume data including three-dimensional morphological information of the region of interest (the mitral valve) in response to the volume data acquisition operation via the input interface 32. For example, the image acquisition function 352 acquires a CT image of the mitral valve taken in three dimensions.

The acquisition processing for the medical image at Step S101 may be started by a user instruction via the input interface 32 as described above, but the processing may be automatically started. In such a case, for example, the image acquisition function 352 monitors the medical image storage apparatus 2 and automatically acquires the volume data each time new volume data is kept.

The image acquisition function 352 may determine the newly kept volume data based on a preset acquisition condition and execute the acquisition processing when the volume data satisfies the acquisition condition. For example, the acquisition condition that can determine the state of the volume data is stored in the storage circuitry 34, and the image acquisition function 352 determines the newly kept volume data based on the acquisition condition stored in the storage circuitry 34.

To give an example, the storage circuitry 34 stores therein as the acquisition condition "acquisition of volume data taken with an imaging protocol for the heart," "acquisition of an enlarged and reconstructed medical image," or a combination thereof. The image acquisition function 352 acquires the volume data satisfying the acquisition condition described above.

Extraction Processing for Region of Interest

As described at Step S102 in FIG. 2, the extraction function 353 extracts the region of interest for the volume data. Specifically, the extraction function 353 identifies the region of interest (the mitral valve) in the CT image and extracts information on the identified region in a preset format. More specifically, the extraction function 353 extracts characteristic positions preset in the region of interest as positions having the same anatomical meaning in the region of interest regardless of differences in the subject. That is, the extraction function 353 acquires coordinate information of part or all of pixels preset in the region indicated by the mitral valve on the CT image.

For example, the extraction function 353 acquires each position in the region of interest as information expressed by an identifier based on an anatomical structure of the identified region of interest. The identifier includes coordinate information based on the anatomical structure of the region of interest and a character string, an ID, and a tag freely assigned to the coordinate information, for example.

To give an example, the extraction function 353 extracts the region of interest as a grid point group in a certain format. That is, the extraction function 353 extracts the region of interest as a mesh represented by a plurality of grid point groups. When the region of interest is extracted as a mesh, the respective grid points will indicate the characteristic positions. By presetting the number and arrangement of the grid points making up this mesh, the region of interest can be extracted in the same format regardless of differences in the form of the region of interest due to differences in the subject (of course, when the form of the region of interest is different, the distance between the grid points will differ). The certain format for extracting the region of interest (the number and arrangement of the grid points making up the mesh, for example) is defined for each type of the region of interest (for each biological organ or each anatomical structure making up a biological organ, for example).

Examples of the characteristic positions of heart valves include the position of the Commissure in the mitral valve and the position of the Arantius body and Nadir in the aortic valve. The characteristic positions in the region of interest may be defined by relative positional relations with the characteristic positions described above. That is, the positions of the respective grid points other than the characteristic positions described above are extracted as positions having the same anatomical meaning between subjects in which all grid points are different from each other by presetting the relative positional relations with the positions of the grid points at the characteristic positions. The relative positions may each be predefined at each grid point or may be defined by defining a method of division in each column or each row (being divided at regular intervals into a preset number, for example).

Figure 3A:
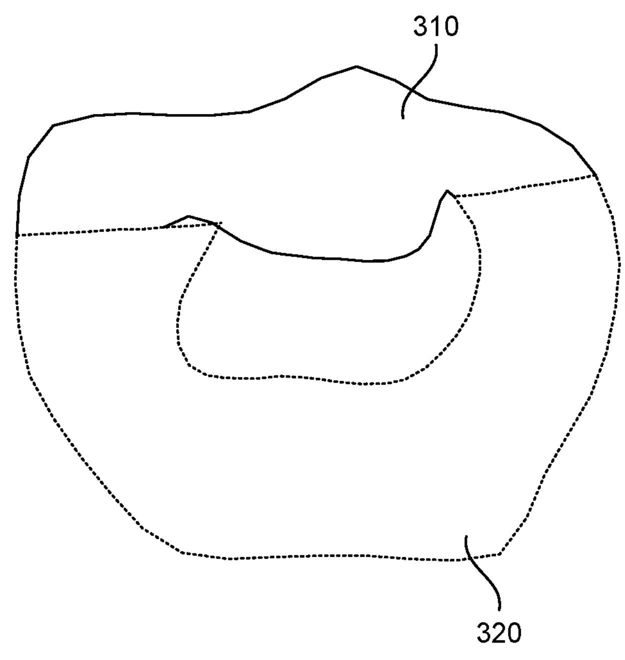
FIG. 3A is a diagram of an example of extraction processing for a region of interest according to the first embodiment.
Figure 3A:
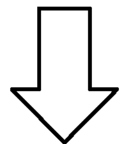
Figure 3A:
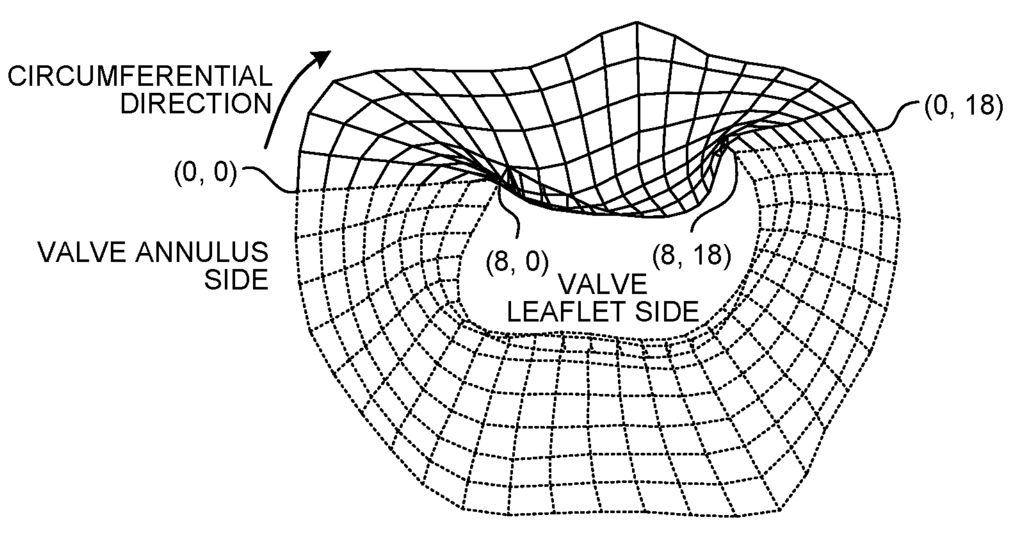
Figure 3B:
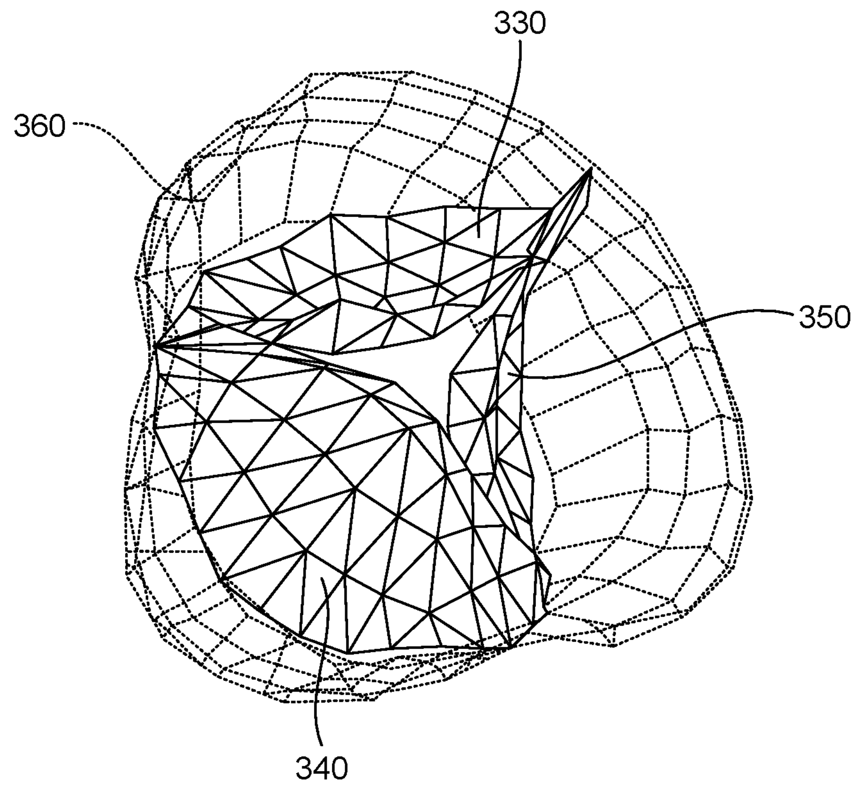
FIG. 3B is a diagram of an example of the extraction processing for the region of interest according to the first embodiment.

The following describes an example of the processing by the extraction function 353 using FIG. 3A and FIG. 3B. FIG. 3A and FIG. 3B are diagrams of an example of the extraction processing for the region of interest according to the first embodiment. For example, as illustrated in the upper drawing in FIG. 3A, the extraction function 353 identifies regions corresponding to the mitral valve in the CT image (an anterior leaflet 310 and a posterior leaflet 320). As illustrated in the lower part in FIG. 3A, the extraction function 353 then extracts each identified region as coordinate information expressed by a plurality of grid point groups in a preset format.

For example, the extraction function 353 extracts the mitral valve as a grid point group expressed in a format based on an (x, y) coordinate system in which the direction from the valve annulus side toward the valve leaflet side is represented by x coordinates with the valve annulus being "0" and the circumferential direction of the valve annulus is represented by y coordinates with the position between the anterior leaflet 310 and the posterior leaflet 320 being "0." In FIG. 3A, the mitral valve is represented by 378 grid points in 9 rows*42 columns present at the positions (0, 0) to (8, 41).

The extraction function 353 may extract the region of interest including a plurality of structures, such as the mitral valve (the anterior leaflet and the posterior leaflet), with a format set in advance for each structure. For example, the anterior leaflet 310 of the mitral valve is represented by 171 points in 9 rows*19 columns present at the positions (0, 0) to (8, 18), and the posterior leaflet 320 of the mitral valve is represented by 225 points in 9 rows*25 columns present at the positions (0, 19) to (8, 44). In this example, by sharing end grid points ((0, 0) to (8, 0) and (0, 18) to (8, 18)) in the anterior leaflet 310 and end grid points ((0, 19) to (8,19) and (0, 44) to (8, 44)) in the posterior leaflet, a grid point group in 9 rows*42 columns is provided as the entire mitral valve as illustrated in the lower part in FIG. 3A.

As illustrated in FIG. 3B, the extraction function 353 can also extract the aortic valve in the same manner with a right coronary cusp 330, a left coronary cusp 340, and a non-coronary cusp 350 represented by a plurality of grid points in a certain preset format. In addition to the grid point group indicating the structure of interest, the extraction function 353 can also extract characteristic positions in a region other than the region of interest that is related to the region of interest together as characteristic points. For example, as illustrated in FIG. 3B, the extraction function 353 can extract a Valsalva sinus 360, which is a periaortic structure, represented by a plurality of grid points.

The extraction function 353 can extract the region of interest by various methods other than the mesh described above. For example, the extraction function 353 extracts the region of interest based on anatomical characteristic points. That is, the extraction function 353 extracts the region of interest by means of a point group indicating the anatomical characteristic points.

As described above, the extraction function 353 extracts the characteristic positions preset in the region of interest as the positions having anatomical meaning. The extraction processing by the extraction function 353 can be implemented by various methods. For example, the extraction function 353 can extract a pixel position corresponding to each grid point position specified on the CT image via the input interface 32. That is, the extraction function 353 extracts each grid point position manually specified by the user as the region of interest.

For example, the extraction function 353 can extract a grid point group based on an anatomical structure represented in the CT image using a known point group extraction technique. For example, the extraction function 353 extracts the region of interest based on an anatomical structure represented in the CT image using a known region extraction technique, then sets a grid point group in a format predefined for the extracted region, and can thereby extract the grid point group.

The extraction function 353 can use, as the known region extraction technique, Otsu's binarization method based on CT values, the region expansion method, the snake method, the graph cut method, or the mean shift method, for example. The extraction function 353 can achieve setting of the grid point group by deforming the grid point group in a predefined format to fit to the extracted region using non-linear deformation alignment processing. For example, known methods such as the free-form deformation (FFD) method and the large deformation diffeomorphic metric mapping (LDDMM) method can be used as the non-linear deformation alignment processing.

In addition, the extraction function 353 can also directly extract the grid point group using a learned model (a point group model) constructed based on data for learning prepared in advance using a machine learning technique (including deep learning). The extraction function 353 can also identify the region of interest using a learned model (a shape model of the region of interest) constructed based on data for learning prepared in advance using a machine learning technique (including deep learning) and then extract the grid point group from the region of interest.

When the region extraction processing such as the graph cut method or the deformation alignment processing such as the LDDMM method is applied to the entire image, calculation costs may be excessively high. Given these circumstances, the extraction function 353 can identify a region that is related to the region of interest and that is larger than the region of interest but smaller than the entire image (hereinafter referred to as a "related region," which is, for example, when the mitral valve is a target organ, a heart region, a region around the left ventricle and the left heart, or the like) and apply the above processing only to the identified related region. The related region may be set manually using the input interface 32.

Once the region of interest is extracted as described above, the extraction function 353 stores an extraction result in the storage circuitry 34. That is, the extraction function 353 stores the extraction result as information indicating a relative positional relation at any position so that each position can be identified for the extracted grid point group. For example, the extraction function 353 performs recording as a coordinate position with the origin of the image or one of the extracted characteristic points as a starting point.

Setting Processing for Calculation Rule

As described at Step S103 in FIG. 2, the setting function 354 sets the calculation rule for calculating the characteristic amount of the region of interest. Specifically, the setting function 354 sets the calculation rule based on the characteristic positions in the region of interest extracted by the extraction function 353. In other words, the setting function 354 sets the calculation rule associating the identifier expressed (specified, defined, added) by the extraction function 353.

For example, the setting function 354 sets the calculation rule based on the grid point group extracted by the extraction function 353. Alternatively, the setting function 354 sets the calculation rule based on the anatomical characteristic points extracted by the extraction function 353. That is, the setting function 354 sets the calculation rule for calculating the characteristic amount using positions extracted as positions having anatomical meaning in the region of interest. The setting function 354 sets the calculation rule for calculating at least one of morphological information and property information of the region of interest as the characteristic amount for the region of interest.

For example, the characteristic amount includes morphological information such as the distance, area, volume, and angle of a specific position in the region of interest and property information such as the maximum value, minimum value, average value, variance value, and histogram of pixel values in a specific range in the region of interest. The characteristic amount described above is only an example, and any type of characteristic amount may be used so long as it is a characteristic amount that can be set by the setting function 354 based on the region of interest extracted at Step S102.

The following describes examples of the characteristic amount set by the setting function 354 using FIG. 4 to FIG. 9. FIG. 4 to FIG. 9 are diagrams for illustrating examples of setting of the calculation rule according to the first embodiment.

Figure 4:
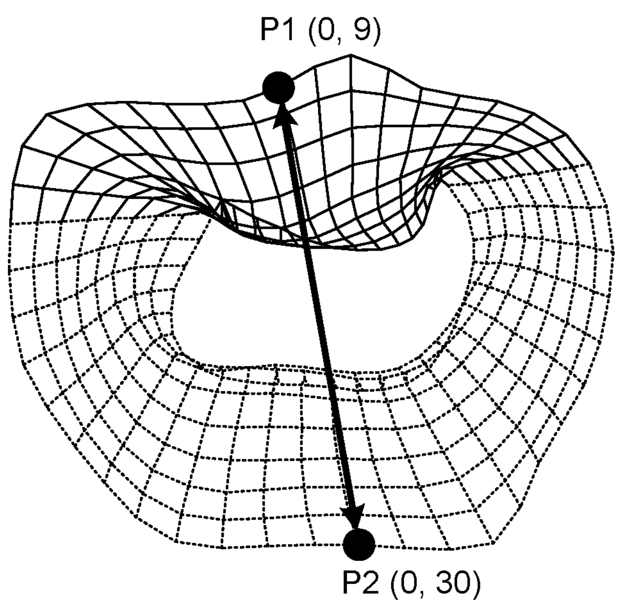
FIG. 4 is a diagram for illustrating an example of setting of a calculation rule according to the first embodiment.

For example, the setting function 354 sets the calculation rule for calculating the characteristic amount indicating a straight-line distance using the characteristic positions in the region of interest. To give an example, as illustrated in FIG. 4, the setting function 354 specifies two points of a grid point P1 at the position (0, 9) and a grid point P2 at the position (0, 30), based on the grid point group indicating the region of interest and sets the calculation rule calculating the distance between the two points. The setting function 354 can set the calculation rule for calculating the distance between any grid points, not limited to between the two points illustrated in the drawing.

Not only the distance between two points, the setting function 354 can also set the calculation rule calculating the distance between any figures that can be defined from the grid point group in the region of interest, such as points, lines, curves, planes, and curved surfaces, such as the distance between a point and a line, the distance between a curve and a curve, the distance between a plane and a point, and the distance between a curved surface and a plane.

Figure 5A:
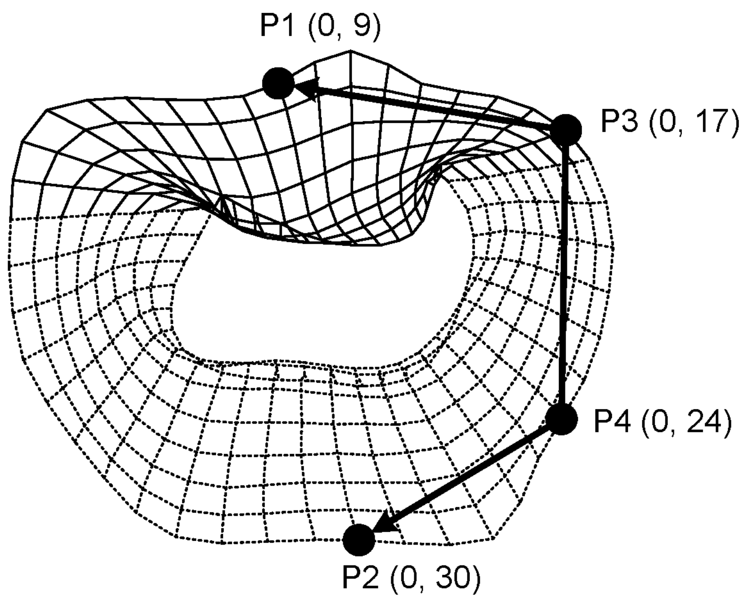
FIG. 5A is a diagram for illustrating an example of setting of the calculation rule according to the first embodiment.

For example, the setting function 354 sets the calculation rule for calculating the characteristic amount indicating the distance of a broken line using the characteristic positions in the region of interest. To give an example, as illustrated in FIG. 5A, the setting function 354 specifies four points of the grid point P1 at the position (0, 9), the grid point P2 at the position (0, 30), a grid point P3 at the position (0, 17), and a grid point P4 at the position (0, 24), based on the grid point group indicating the region of interest and sets the calculation rule calculating the total value of the distance between P1 and P3, the distance between P3 and P4, and the distance between P4 and P2. The setting function 354 can set the calculation rule for calculating the distance of a broken line formed between any points, not limited to the points illustrated in the drawing.

Figure 5B:
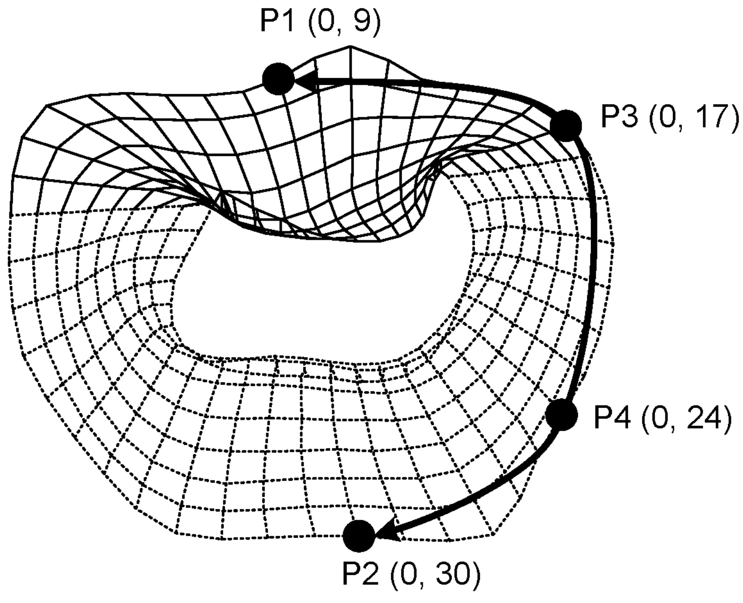
FIG. 5B is a diagram for illustrating an example of setting of the calculation rule according to the first embodiment.

For example, the setting function 354 sets the calculation rule for calculating the characteristic amount indicating the distance of an open curve using the characteristic positions in the region of interest. To give an example, as illustrated in FIG. 5B, the setting function 354 specifies four points similar to those in FIG. 5A and sets the calculation rule calculating the distance of a smooth open curve (a spline curve, for example) passing through the four points. The setting function 354 can set the calculation rule for calculating the distance of an open curve formed using any points, not limited to the points illustrated in the drawing.

Figure 6A:
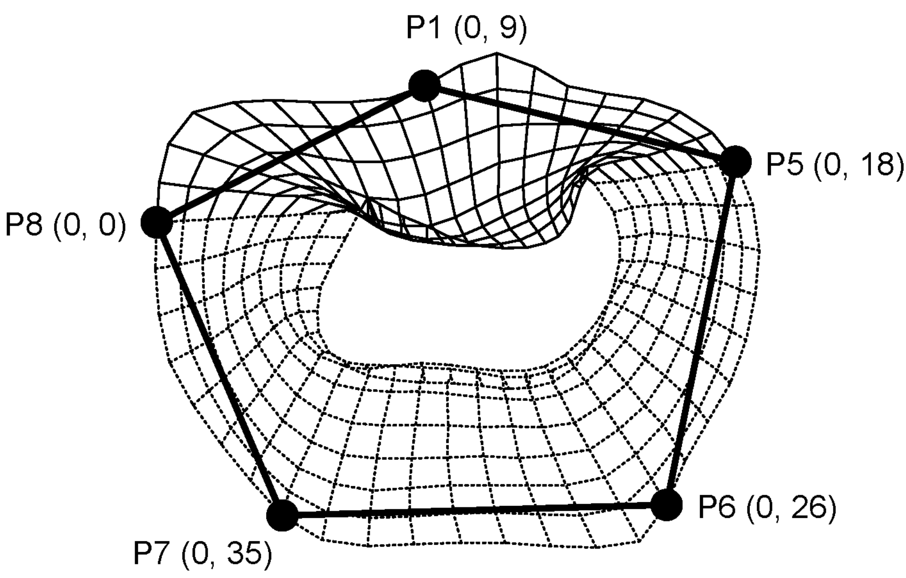
FIG. 6A is a diagram for illustrating an example of setting of the calculation rule according to the first embodiment.

For example, the setting function 354 sets the calculation rule for calculating the characteristic amount indicating the perimeter and/or area of a rectangle using the characteristic positions in the region of interest. To give an example, as illustrated in FIG. 6A, the setting function 354 specifies five points of the grid point P1 at the position (0, 9), a grid point P5 at the position (0, 18), a grid point P6 at the position (0, 26), a grid point P7 at the position (0, 35), and a grid point P8 at the position (0, 0) based on the grid point group indicating the region of interest and sets a rule calculating the perimeter and/or area of the rectangle (a pentagon in this example) with these five points as vertices.

Figure 6B:
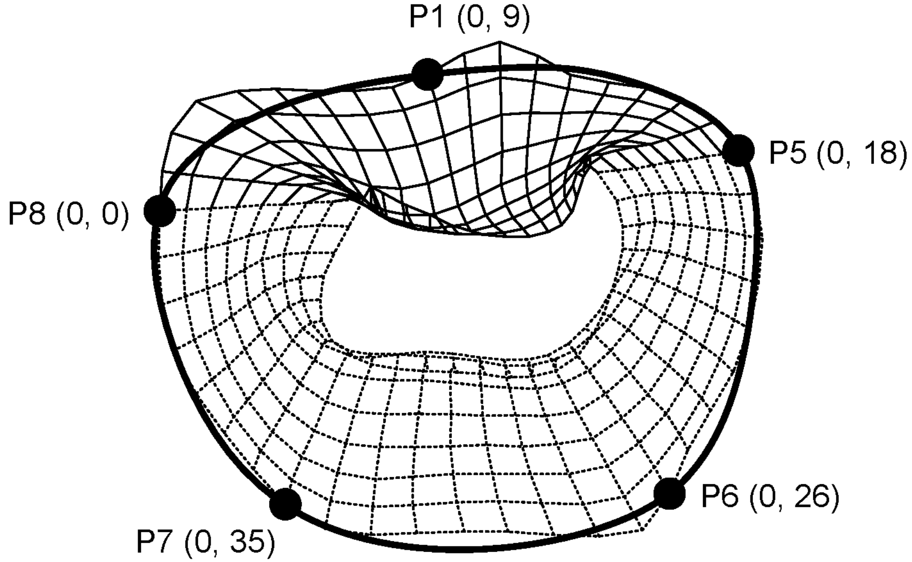
FIG. 6B is a diagram for illustrating an example of setting of the calculation rule according to the first embodiment.

Similarly, as illustrated in FIG. 6B, the setting function 354 specifies the five points of the grid point P1, the grid point P5, the grid point P6, the grid point P7, and the grid point P8, and set the calculation rule calculating the perimeter and/or area of a smooth closed curve passing through the five points. The closed curve may be calculated as a smooth curve using spline interpolation or the like or calculated as a circle or ellipse by circular approximation or elliptical approximation. Circular approximation and elliptical approximation can be easily approximated by using the least-squares method.

When calculating a circle or ellipse, the setting function 354 can also set the calculation rule calculating not only the perimeter and area but also the radius and diameter of a circle, the major diameter, minor diameter, and ellipticity of an ellipse, or the like. The setting function 354 can also set the calculation rule calculating, based on pixel values in the area inside the closed curve, pixel distribution (histogram) inside the closed curve, the average value of the pixel values, the maximum value of the pixel values, the minimum value of the pixel values, the variance and/or deviation of the pixel values, the number of pixels having pixel values within a specific range (including a certain value or more or a certain value or less), or the like.

Figure 7:
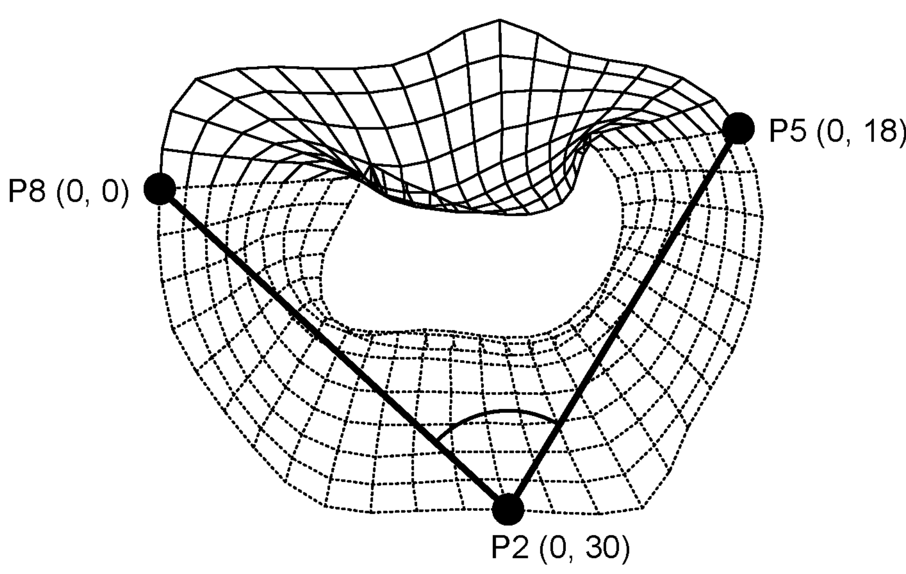
FIG. 7 is a diagram for illustrating an example of setting of the calculation rule according to the first embodiment.

For example, the setting function 354 sets the calculation rule for calculating the characteristic amount indicating an angle using the characteristic positions in the region of interest. To give an example, as illustrated in FIG. 7, the setting function 354 specifies three points of the grid point P2 at the position (0, 30), the grid point P5 at the position (0, 18), and the grid point P8 at the position (0, 0), based on the grid point group indicating the region of interest and sets the calculation rule calculating the size of an acute angle or obtuse angle formed by the three points.

For example, the setting function 354 can also set a three-dimensional region such as a cube, a rectangular parallelepiped, a polyhedron, a sphere, or an ellipsoidal sphere using the characteristic positions in the region of interest and set the calculation rule calculating the volume of the three-dimensional region, pixel distribution (histogram) inside the three-dimensional region, the average value of pixel values, the maximum value of the pixel values, the minimum value of the pixel values, the variance and/or deviation of the pixel values, the number of pixels having pixel values within a specific range (including a certain value or more or a certain value or less), or the like.

In setting the three-dimensional region, in the case of a cube, a rectangular parallelepiped, or a polyhedron, the characteristic points necessary to form the three-dimensional region, such as the center or vertices thereof, may be set, or any four or more grid points that do not exist on the same plane may be specified, and a circumscribed or inscribed rectangular parallelepiped of the grid point group may be set. In the case of a sphere or an ellipsoidal sphere too, it may be possible to set characteristic points such as the center and foci thereof and information necessary to form the three-dimensional region, such as the radius thereof. Alternatively, an algorithm calculating an approximate shape such as a polygon or sphere with a form preset based on specified grid points may be defined in advance, and the three-dimensional region may be set by applying the algorithm to any grid point group.

The above is only an example, and any calculation rule may be set so long as it is calculation of the characteristic amount based on the region of interest or the characteristic points related to the region of interest calculated at Step S102. In FIG. 4 to FIG. 7, for convenience of description, the x-coordinates of all the grid points used to set the calculation rule are 0, but of course they do not have to be 0, and a plurality of grid points having different x-coordinates may be set in the calculation rule.

The above example describes a case in which in setting the calculation rule, the calculation rule is set by specifying any grid points in the grid point group indicating the region of interest or the characteristic points related to the region of interest. However, the embodiment is not limited to this example, and instead of directly selecting the grid points from the grid point group, a point other than the grid points that can be identified from the grid point group may be specified.

Figure 8:
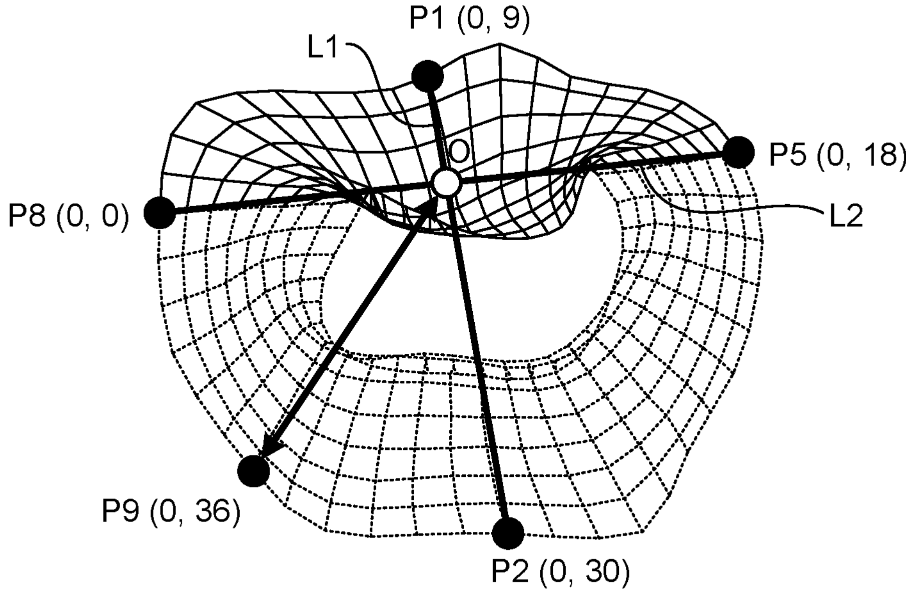
FIG. 8 is a diagram for illustrating an example of setting of the calculation rule according to the first embodiment.

For example, as illustrated in FIG. 8, the setting function 354 specifies an intersection point O of a straight line L1 with two points of the grid point P1 at the position (0, 9) and the grid point P2 at the position (0, 30), as end points and a straight line L2 with two points of the grid point P5 at the position (0, 18) and the grid point P8 at the position (0, 0), as end points as the characteristic point. The setting function 354 can thereby set the calculation rule calculating the distance between a grid point P9 at the position (0, 36) and the intersection point O, for example. The setting function 354 can set an intersection point of straight lines formed using any points, not limited to the points illustrated in the drawing. In addition, the setting function 354 can set not only the intersection point of straight lines but also an intersection point of a curve and a curve, an intersection point of a curved surface and a straight line, or the like.

Figure 9:
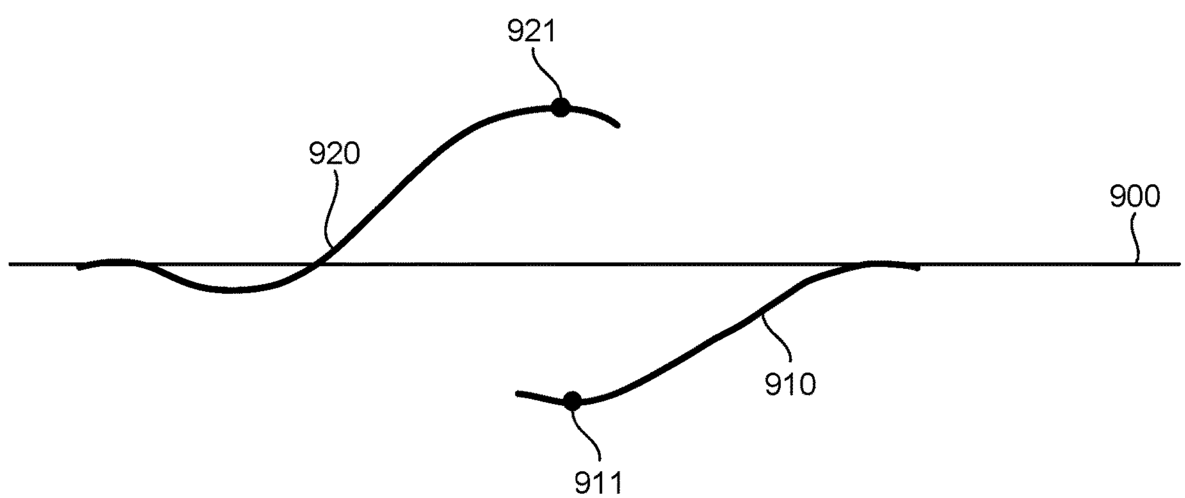
FIG. 9 is a diagram for illustrating an example of setting of the calculation rule according to the first embodiment.

The setting function 354 can also specify any grid point in the grid point group that is farthest or nearest from any point or region that can be identified from the grid point group. To give an example, the setting function 354 identifies a cross section passing through three points of the grid point P5, the grid point P2, and the grid point P8 illustrated in FIG. 8, and specifies a grid point at the farthest straight-line distance from the cross section out of the grid point group indicating the mitral valve. That is, as illustrated in FIG. 9, the setting function 354 identifies a cross section 900 passing through the three points of the grid point P5, the grid point P2, and the grid point P8, and specifies a grid point 911 that is farthest from the cross section 900 in an anterior leaflet 910 and a grid point 921 that is farthest from the cross section 900 in a posterior leaflet 920. FIG. 9 illustrates a cross section of the mitral valve formed by a plane passing through the grid point 911 that is farthest from the cross section 900 in the anterior leaflet 910 in FIG. 8 and the grid point 921 that is farthest from the cross section 900 in the posterior leaflet 920.

The setting function 354 can also set the calculation rule combining a plurality of various characteristic amounts calculated by the above calculation rules. That is, the setting function 354 can set each calculation rule and a numerical formula connecting each calculation rule. In addition, the setting function 354 can also set the calculation rule with a weight set on each characteristic amount. For user convenience, it is realistic to set the numerical formula with simple four arithmetic operations, but it may be possible to set any numerical formula.

For example, the calculation rule calculating the sum (total value) of the distance of the straight line L1 and the distance of the straight line L2 in FIG. 8 may be set, or a rule, giving a double weight to the straight line L1, calculating the sum (total value) of double the distance of the straight line L1 and the distance of the straight line L2 may be set.

In addition, to enable setting of any evaluation indices by the user, it may be possible to set a numerical formula for characteristic amounts with different types of units. For example, it may be possible to calculate the sum of the area within the closed curve illustrated in FIG. 6B and the value of the angle represented in FIG. 7.

The setting function 354 sets the various calculation rules described above in accordance with specification by the user and stores the set calculation rules in the storage circuitry 34. The setting function 354 reads the calculation rule already stored in the storage circuitry 34 to set the calculation rule for the region of interest extracted by the extraction function 353.

Figure 10A:
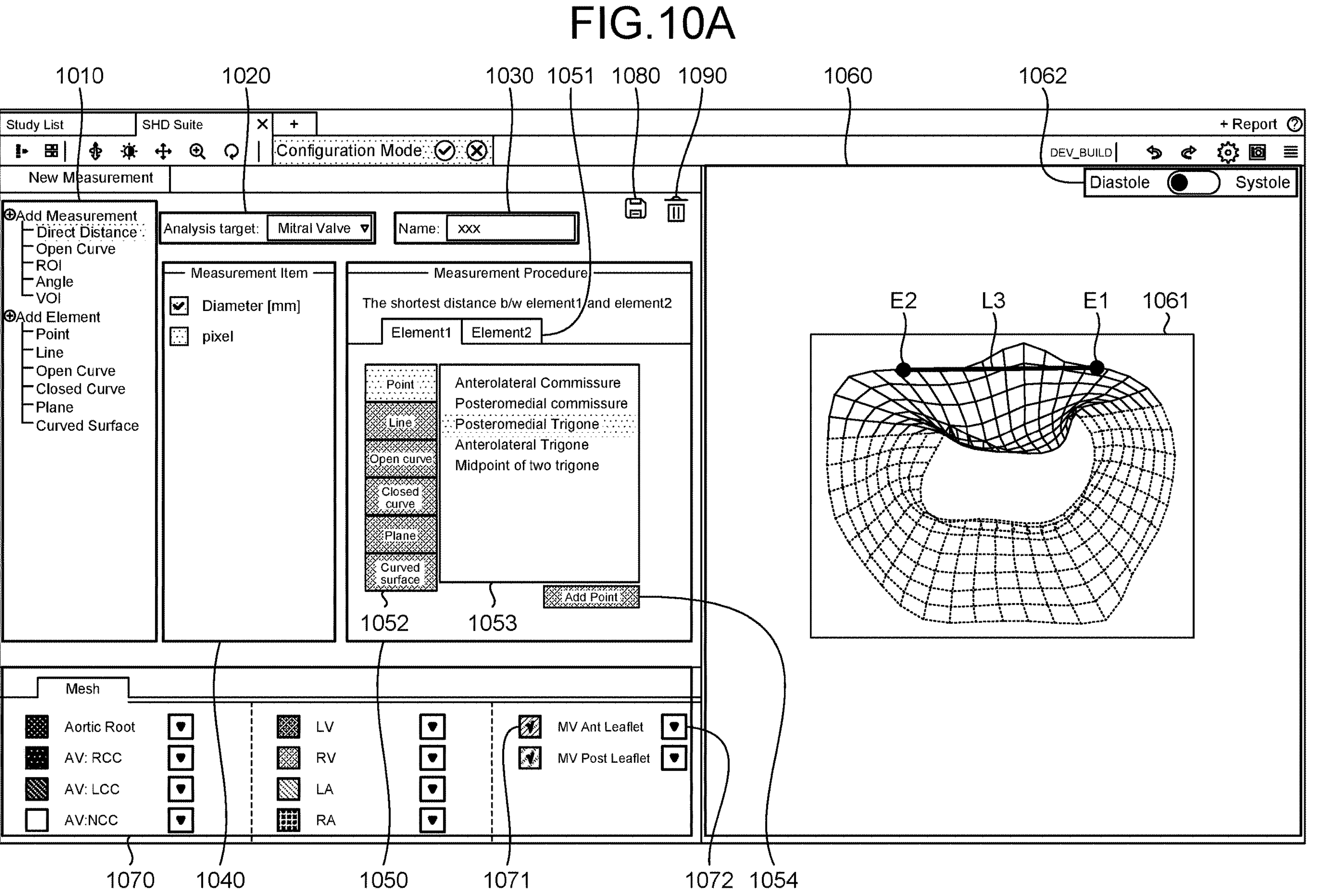
FIG. 10A is a diagram of an example of a screen for setting the calculation rule according to the first embodiment.
Figure 10B:
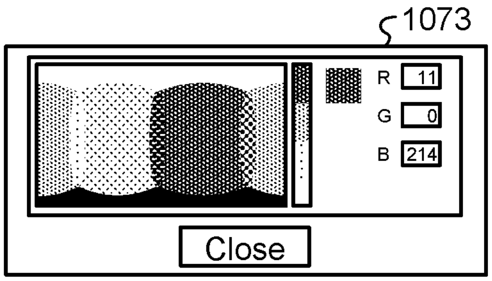
FIG. 10B is a diagram of an example of the screen for setting the calculation rule according to the first embodiment.

The following describes examples of a GUI for setting the calculation rule and examples of user operations. For example, the setting function 354 sets the calculation rule in response to user operations via the GUI described below. FIG. 10A and FIG. 10B are diagrams of examples of a screen for setting the calculation rule according to the first embodiment. For example, as illustrated in FIG. 10A, the control function 351 displays a GUI including an area 1010 to an area 1070, a button 1080, and a button 1090 on the display 33 and receives user operations via the GUI.

The area 1010 in FIG. 10A is an area for selecting the type of a measurement item to be newly set (Add Measurement) or an element making up the calculation rule (Add Element, which will be described below). The user selects one of these options.

The example in FIG. 10A illustrates a state in which the control function 351 displays, as the type of the measurement item that can be selected, "Direct Distance," "Open Curve," "ROI," "Angle," and "VOI," with "Direct Distance" being selected. The type of each measurement item and a GUI and a processing system when it is selected will be described in detail below. In the example in FIG. 10A, the control function 351 displays, as the element making up the calculation rule that can be selected, "Point," "Line," "Open Curve," "Closed Curve," "Plane," and "Cureved Surface."

These are only an example, and it may be possible to set other options. The control function 351 changes the display in the area 1040 and the area 1050 based on the selection of options in the area 1010 (this point will be described in detail below).

The area 1020 in FIG. 10A is an area selecting an analysis target, and the user selects an anatomical structure corresponding to the region of interest ("Mitral Valve," for example). The selection of the area 1020 is for selecting a template for a grid point group to be initially displayed in the area 1060, which will be described below, and for managing the measurement item (the calculation rule) to be set internally by the computer and is not necessarily necessary, and the presence or absence of this area cannot be a limiting factor of the present embodiment.

The area 1030 in FIG. 10A is an area setting the name of the measurement item to be set, and the user can set any measurement item name using the input interface 32 such as a keyboard. If the set measurement item name is the same as a measurement item name already in use, it may be controlled such that a warning is displayed and the name cannot be registered, or it may be controlled such that a preset or random character string is automatically added to the beginning or end of the name, which is then registered. Of course, it may be controlled such that names deviating from preset rules cannot be set, or a warning may be displayed to encourage correction.

The area 1040 in FIG. 10A is an area setting a measurement item corresponding to the type of the measurement item selected in the area 1010. Specifically, the area 1010 is an area setting the type of an item to be a measurement target in the measurement item to be newly set, and the area 1040 is an area setting the type of calculation details to be executed in the measurement item to be newly set. That is, the area 1040 is an area setting what calculation will be performed on the measurement target set in the area 1010. In the following, the type of the measurement item set in the area 1010 will be referred to as a measurement target item, and the type of the measurement item set in the area 1040 will be referred to as a measurement item. The type of the measurement item for the type of each measurement target item (Add Measurement) will be described below, and the example in FIG. 10A illustrates a state in which the control function 351 displays options "Diameter [mm]" and "pixel," with "Diameter [mm]" being selected. "Diameter [mm]" means that the distance (mm) of a straight line to be set in real space is calculated. In addition, "pixel" means that the number of pixels that the straight line to be set passes through in an image is calculated. In the example in FIG. 10A, only "Diameter [mm]" is selected, but both may be selected.

The area 1050 in FIG. 10A is an area setting a detailed calculation rule. The calculation rule is set mainly based on an Element. In the example in FIG. 10A, the control function 351 displays a UI for setting the calculation rule of "Direct Distance." "Direct Distance (that is, straight-line distance)" can be calculated as the minimum distance between two Elements. Thus, the area 1050 is a UI in which two Elements can be selected. In the example in FIG. 10A, the setting of the two Elements can be switched by a tab 1051. A tab 1052 enables selection of the type of the Element, and in FIG. 10A, an Element of "Point" is selected.

An area 1053 lists Elements that can be selected (that is, a list of Elements of "Point" is displayed). The Elements that can be selected listed in the area 1053 are Elements preset using "Add Element" in the area 1010. The displayed Elements may be only Elements related to the region of the analysis target set in the area 1020 or may be displayed together with Elements related to other different targets. It may also be possible to switch between them. In the example in FIG. 10A, an Element of "Posteromedial Trigone" is selected. If a desired Element is not present in the list, the user can select "Add Element" in the area 1010 to add the Element before setting the calculation rule. A button 1054 is a button to transition to the same screen as when "Point" of "Add Element" is selected.

The area 1060 in FIG. 10A is an area displaying a template of a grid point group showing an anatomical structure to which the calculation rule is applied. The control function 351 displays grid points with the positional relation maintained as in a grid point group 1061 and can thereby display the grid point group showing the anatomical structure. The grid point group 1061 shows a template of a grid point group showing the mitral valve. The grid point group (template) displayed in this GUI is a display to enable the user to visually recognize measurement positions corresponding to the set calculation rule, and thus there is no need to display a different template for each user, and there may be one template for each target structure. Of course, a plurality of templates of grid point groups may be prepared in advance for the same anatomical structure, and the user may be caused to freely select the template of the grid point group to which the calculation rule is applied when the calculation rule is set based on this GUI. The grid point group of the region can be observed from any direction by an instruction via the input interface 32 such as a mouse.

In the example in FIG. 10A, the grid point group is displayed as a mesh formed by a group of quadrangles by connecting adjacent grid points to each other by straight lines, but it may be displayed by any display form so long as the positional relation among the grid points making up the displayed grid point group is maintained. The displayed template may display only the template related to the anatomical structure specified in the area 1020, or the user may be able to freely switch to other templates. Of course, it may be possible to simultaneously display a plurality of templates.

In the grid point group 1061 in FIG. 10A, a point E1 is displayed at a position corresponding to Point set as an Element1 in the area 1050 and a point E2 is displayed at a position corresponding to Point set as an Element2 in the area 1050. The control function 351 displays a straight line L3 corresponding to the straight line for calculating Direct Distance set in the area 1010 as the calculation rule. Thus, points, lines, curves, regions, ROIs, angles, or the like corresponding to the selected Element or the calculation rule are displayed together with the grid point group, and thereby the calculation rule set by the user can be visually grasped.

A button 1062 is a button for switching templates. Heart valves move, and thus the positional relation of the grid point group differs, especially between the systolic phase and the diastolic phase of the heart. Thus, one template may not be able to set the calculation rule. Thus, selecting the button 1062 can switch between a template for the systolic phase and a template for the diastolic phase. Of course, instead of the button 1062, it may be possible to select a cardiac phase when the analysis target is selected in the area 1020 by defining a plurality of analysis targets such as the mitral valve in the diastolic phase and the mitral valve in the systolic phase. In that case, the button 1062 is not needed. In FIG. 10A, the GUI enables switching between only two phases of the systolic phase and the diastolic phase, but a GUI enabling selection of any cardiac phase in 0 to 99% may be included.

The area 1070 in FIG. 10A is an area for setting the template to be displayed in the area 1060 and its display conditions. The example in FIG. 10A sets, as the grid point group (template) that can be displayed, "Aortic Root," "AV: RCC (Aortic Valve: Right Coronary cusp)," "AV: LCC (Aortic Valve: Left Coronary cusp)," "AV: NCC (Aortic Valve: None Coronary cusp)," "LV (Left Ventricle)," "RV (Right Ventricle)," "LA (Left Atrial)," "RA (Right Atrial)," "MV Ant Leaflet (Mitral Valve Anterior Leaflet)," and "MV Post Leaflet (Mitral Valve Posterior Leaflet)," with "MV Ant Leaflet" and "MV Post Leaflet" being selected by checking a button 1071.

By selecting a button 1072, a screen such as a window 1073 illustrated in FIG. 10B is displayed, enabling the user to set the display conditions when each grid point group is displayed in the area 1060. In the window 1073, a display color can be selected by setting RGB values. Of course, the display conditions that can be set are not limited to this example, and it may be possible to set color conditions such as transparency, saturation, and brightness and the thickness of the lines connecting the grid points to each other. The display color may be able to be set in YCbCr, not limited to RGB, or in grayscale. Instead of allowing the user to input any numerical values as in the window 1073, any lookup table or candidate colors that can be used may be presented, and the user may be allowed to select one.

It may be possible to change the type of the display form of the grid point group 1061 in the area 1060. For example, the grid point group 1061 in FIG. 10A is displayed as a mesh, but it may be possible to be switched to polygon display or the display of only a grid point group with no straight lines connecting the grid points to each other.

The button 1080 is a button for saving the set calculation rule or Element, and selecting the button 1080 records the calculation rule or Element in any storage area in the storage circuitry 34. The button 1090 is a delete button, and selection of the button 1090 deletes the set calculation rule or Element.

Next, the following describes the details of the Element. The Element is a component of the calculation rule. The following describes how to define the Element for each of "Point," "Line," "Open Curve," "Closed Curve," "Plane," and "Cureved Surface" together with examples of a GUI. However, the elements making up the calculation rule are not limited to these examples, and any Element may be set.

(Setting of Point)

First, the following describes setting of the Element of "Point" using FIG. 11A to FIG. 11F. FIG. 11A to FIG. 11F are diagrams of examples of a GUI setting the Element of "Point" according to the first embodiment. FIG. 11A to FIG. 11F are screen examples corresponding to the area 1050 in FIG. 10A when "Point" of Add Element is selected in the area 1010. When Add Element is selected, nothing may be displayed in the area 1040, or the area of the area 1040 itself may not be displayed, but instead the area 1050 may be displayed in a larger size, including up to the range in which the area 1040 is displayed. This also applies to cases when the other Elements below are selected.

Figures 11A, 11B:
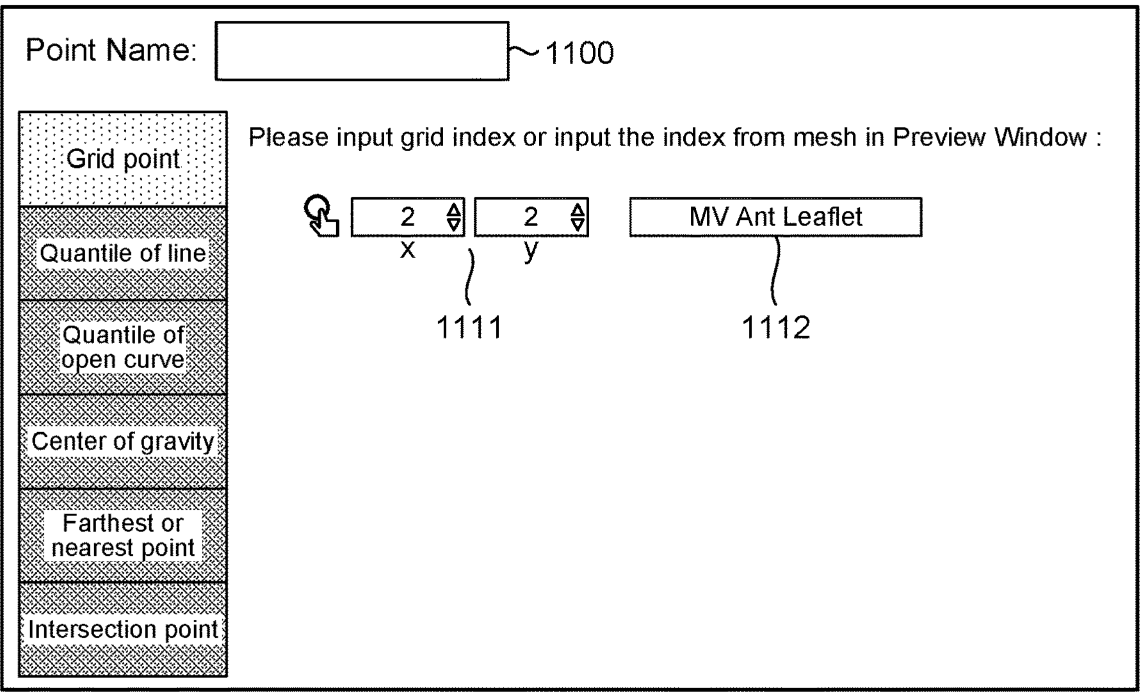
FIG. 11A is a diagram of an example of a GUI setting an Element of "Point" according to the first embodiment.
FIG. 11B is a diagram of an example of the GUI setting the Element of "Point" according to the first embodiment.

FIG. 11A illustrates an example of a GUI for a method for selecting any one grid point from a grid point group. An area 1100 in FIG. 11A is an area for setting the name of the Element to be set, and the user sets any name using the input interface 32 such as a keyboard. As described in the area 1030 in FIG. 10A, if the set measurement item name is the same as a measurement item name already in use, it may be controlled such that a warning is displayed and the name cannot be registered, or it may be controlled such that a preset or random character string is automatically added to the beginning or end of the name, which is then registered. Of course, it may be controlled such that names deviating from preset rules cannot be set, or a warning may be displayed to encourage correction.

The UIs 1111 and 1112 are UIs for selecting any grid points from the grid point group, and a target grid point group is selected in the UI 1112. In the UI 1112, it may be controlled such that the grid point group of the region displayed in the area 1060 or the grid point group corresponding to the region of interest set as the analysis target as the area 1020 is automatically set as an initial value.

The UI 1111 is information indicating the positional relation of the grid point group to be set as the Element in the grid point group set in the UI 1112. In FIG. 11A, the UI 1111 is shown in an (x, y) coordinate system, but the positional relation may be defined in any form. The information on the positional relation may be input directly in the UI 1111, or it may be controlled such that by selecting target grid points in the template displayed in the area 1060, the information on the positional relation corresponding to the selected grid points is automatically input. In FIG. 11A, the Element of "Point" is set by selecting one point from the grid point group, but if the characteristic positions in a region other than the region of interest related to the region of interest have been extracted as the characteristic points in addition to the grid point group indicating the region of interest at Step S102, it may be possible to select the characteristic points.

FIG. 11B illustrates an example of a GUI for setting any quantile point for a specified line segment. The UI 1121 displays a list of preset Elements of "Line." The user selects one Element of Line from the list. The UI 1122 is an example of a GUI for setting a quantile q (for a real number $q \notin [0,1]$, the q-quantile is a value dividing the distribution by $q:1-q$). That is, in the GUI illustrated in FIG. 11B, the point at the position of q when the selected Line is divided by $q:1-q$ is set as the Element of "Point."

Figures 11C, 11D:
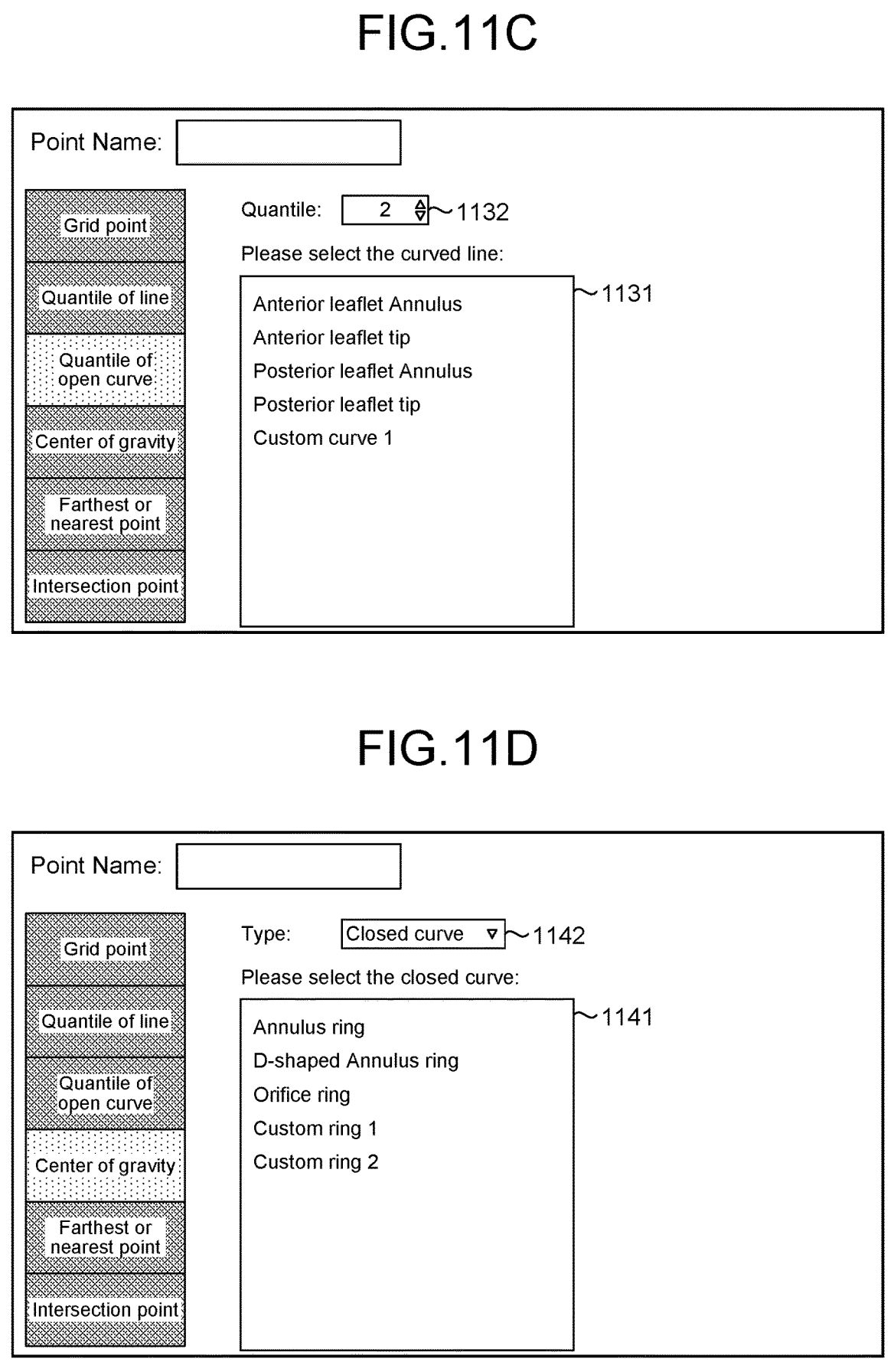

FIG. 11C illustrates an example of a GUI for setting any quantile point for a specified open curve. The UI 1131 displays a list of preset Elements of "Open Curve." The user selects one Element of "Open Curve" from the list. The UI 1132 is a GUI for setting the quantile q like FIG. 11B. That is, in the GUI illustrated in FIG. 11C, the point at the position of q when the selected "Open Curve" is divided by $q:1-q$ is set as the Element of "Point."

FIG. 11D is a diagram of an example of a GUI setting the center of gravity of a grid point group corresponding to a specified Element (open curve, closed curve, or closed surface) as the Element of "Point." The type of the Element to be specified is selected by the UI 1142. By selecting the UI 1142, a list of corresponding Elements is displayed in the UI 1141. By selecting one Element out of the list displayed in the UI 1141, the user sets the center of gravity of the Element as the Element of "Point." Not only the center of gravity, it may be possible to set a characteristic point (an inner center, an outer center, a vertical center, or an excenter, for example) that can be calculated from the grid point group.

Figure 11E:
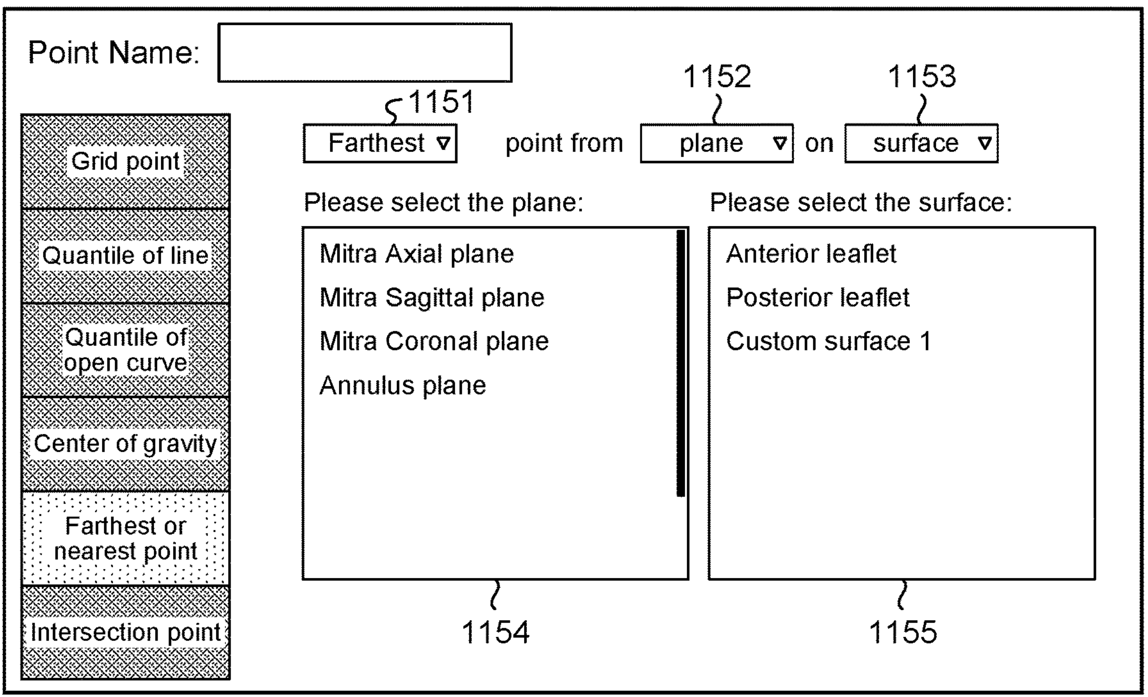
FIG. 11E is a diagram of an example of the GUI setting the Element of "Point" according to the first embodiment.

FIG. 11E is an example of a GUI setting the farthest point or the nearest point, out of a grid point group making up any Element1, from an Element2, which is different from the Element1, as the Element of "Point." Any type of the Element1 is selected by the UI 1153. Elements corresponding to the type of the Element1 are thereby listed in the UI 1155. The user then selects the Element1 from the list. The Element1 is selected from Elements including a plurality of grid points (that is, no Element of "Point" is set). Then, the type of the Element2 that will be a base point for calculating a distance is selected by the UI 1152. Elements corresponding to the type of the Element2 are thereby listed in the UI 1154. The user then selects the Element2 from the list. Finally, in the UI 1151, whether to set the grid point at the "furthest position" from the Element2 as the Element of "Point" or set the grid point at the "nearest position" as the Element of "Point" out of the grid point group making up the Element1 is selected.

Figure 11F:
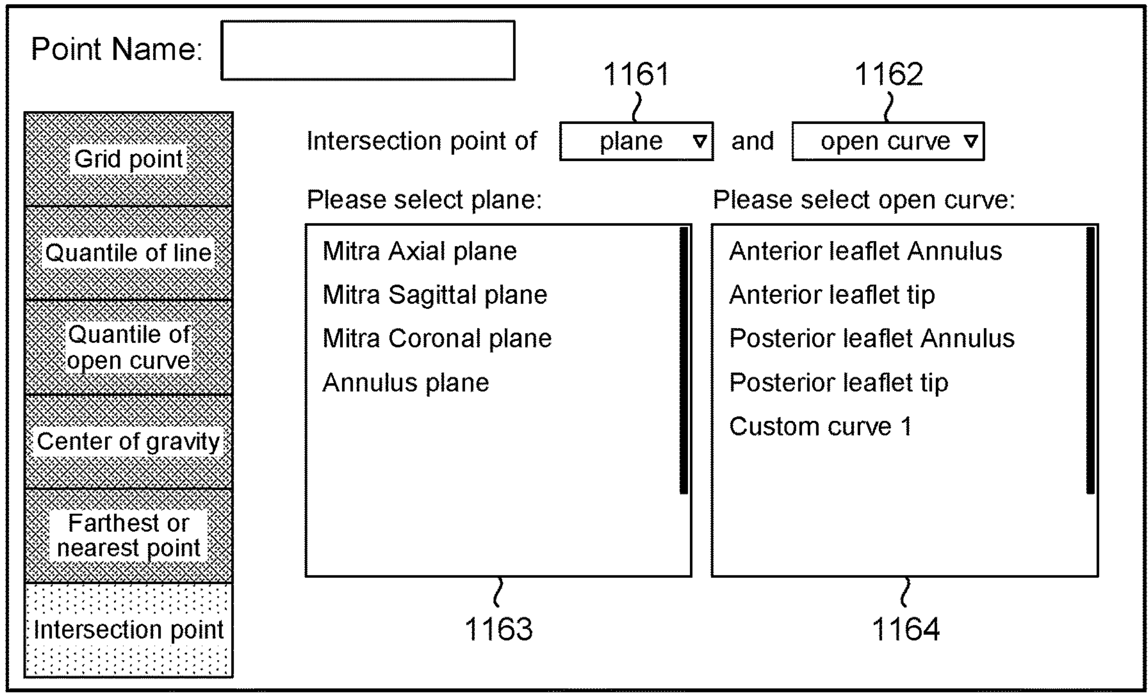
FIG. 11F is a diagram of an example of the GUI setting the Element of "Point" according to the first embodiment.

FIG. 11F illustrates an example of a GUI for setting an intersection point of any two Elements as the Element of "Point." By the UIs 1161 and 1162, the types of the two Elements for which the intersection point is determined are set. The types of the Elements set in the UIs 1161 and 1162 may be the same type or different types. By the UIs 1161 and 1162 being selected, a list of corresponding Elements is displayed in the UIs 1163 and 1164, and the user selects one Element each from the displayed lists.

It may be controlled such that if it is obvious that the two selected Elements do not have any intersection point (they are parallel, for example) (whether it is obvious is defined in advance), a warning is displayed to prohibit selection. The setting of the Element of "Point" has been specifically described so far, but the embodiment is not limited to these GUIs. The Element of "Point" may be set in any way so long as one specific point can be set from the relation of the grid point group.

(Setting of Line)

Figure 12:
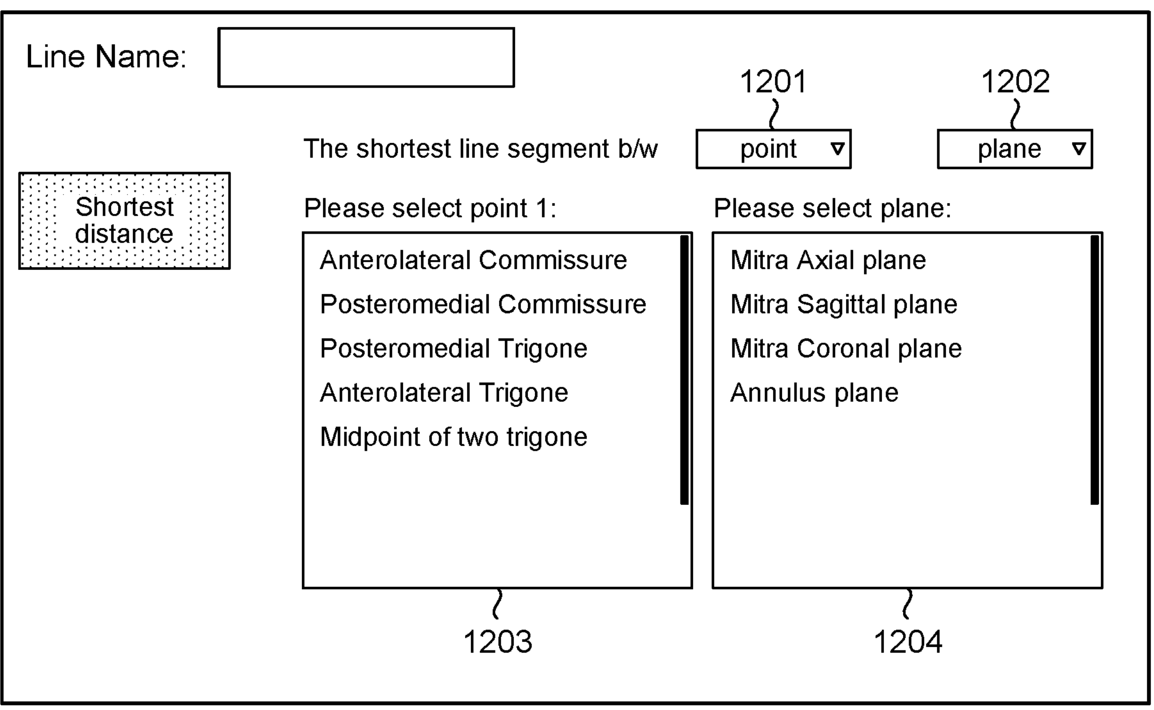
FIG. 12 is a diagram of an example of a GUI setting the Element of "Line" according to the first embodiment.

Next, the following describes setting of the Element of "Line" using FIG. 12. FIG. 12 is a diagram of an example of a GUI setting the Element of "Line" according to the first embodiment. FIG. 12 is a screen example corresponding to the area 1050 in FIG. 10A when "Line" of Add Element is selected in the area 1010. In FIG. 12, the Element of "Line" is defined as a straight line corresponding to the position of the minimum distance between any two Elements. By the UIs 1201 and 1202, the types of the two Elements for which the minimum distance is determined are set. The types of the Elements set in the UIs 1201 and 1202 may be the same type or different types. By the UIs 1201 and 1202 being selected, a list of corresponding Elements is displayed in the UIs 1203 and 1204, and the user selects one Element each from the displayed lists. The setting function 354 identifies the minimum distance between the two selected Elements and the position of the straight line having the minimum distance and sets the straight line as the Element of "Line." It may be controlled such that if it is obvious that the two selected Elements do not have any distance (they cross each other or they are a plane and a point on the plane, for example) (whether it is obvious is defined in advance), a warning is displayed to prohibit selection.

(Setting of Open Curve)

Next, the following describes setting of the Element of "Open Curve" using FIG. 13A to FIG. 13G. FIG. 13A to FIG. 13G are diagrams of examples of a GUI setting the Element of "Open Curve" according to the first embodiment. FIG. 13A to FIG. 13G are screen examples corresponding to the area 1050 in FIG. 10A when "Open Curve" of Add Element is selected in the area 1010.

Figures 13A, 13B:
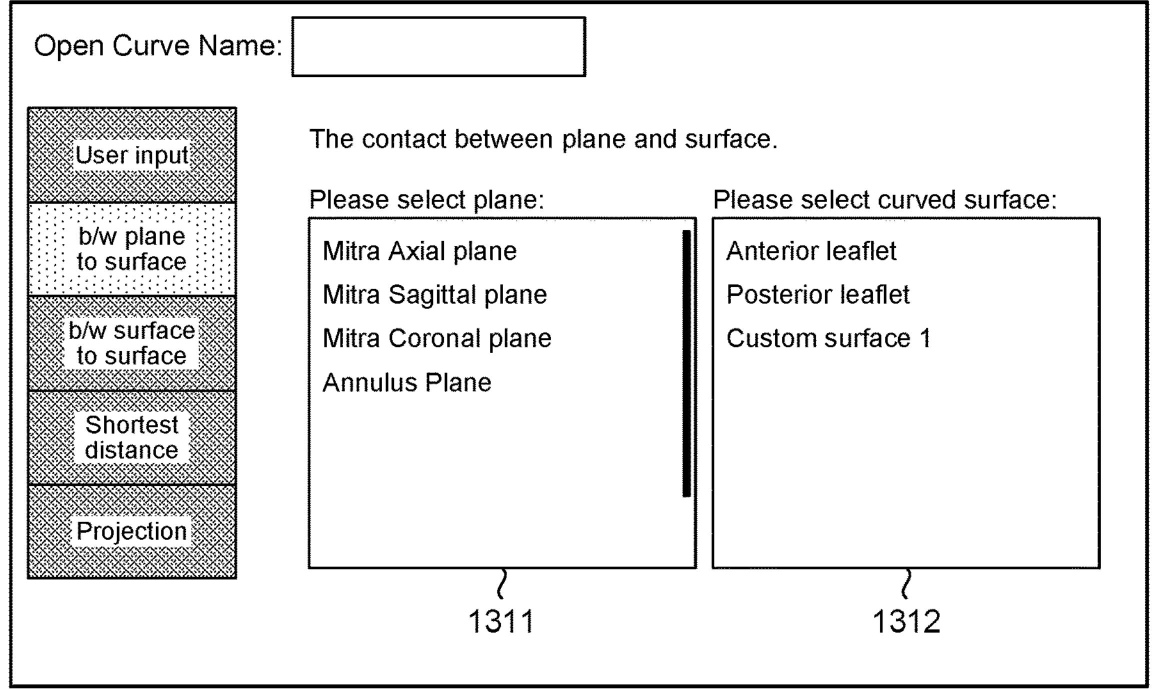
FIG. 13A is a diagram of an example of a GUI setting the Element of "Open Curve" according to the first embodiment.
FIG. 13B is a diagram of an example of the GUI setting the Element of "Open Curve" according to the first embodiment.

FIG. 13A is an example of a GUI for calculating a curve or broken line from any three or more points and setting it as the Element of "Open Curve." The three or more points may be selected from a list of Elements of "Point" displayed in the UI 1302 or selected by specifying any grid points for the template displayed in the area 1060 in FIG. 10A using the input interface 32. The UI 1301 is a UI for selecting whether the line connecting the selected point group is to be "Curve" or "Straight Line." When "Straight Line" is selected, a broken line connecting the selected point group with straight lines in a certain order (the order of being set, for example) is set as the Element of "Open Curve." When "Curve" is selected, the selected point group is interpolated using known curve approximation processing (spline curve, for example) to create a curve, which is set as the Element of "Open Curve."

Figure 13C:
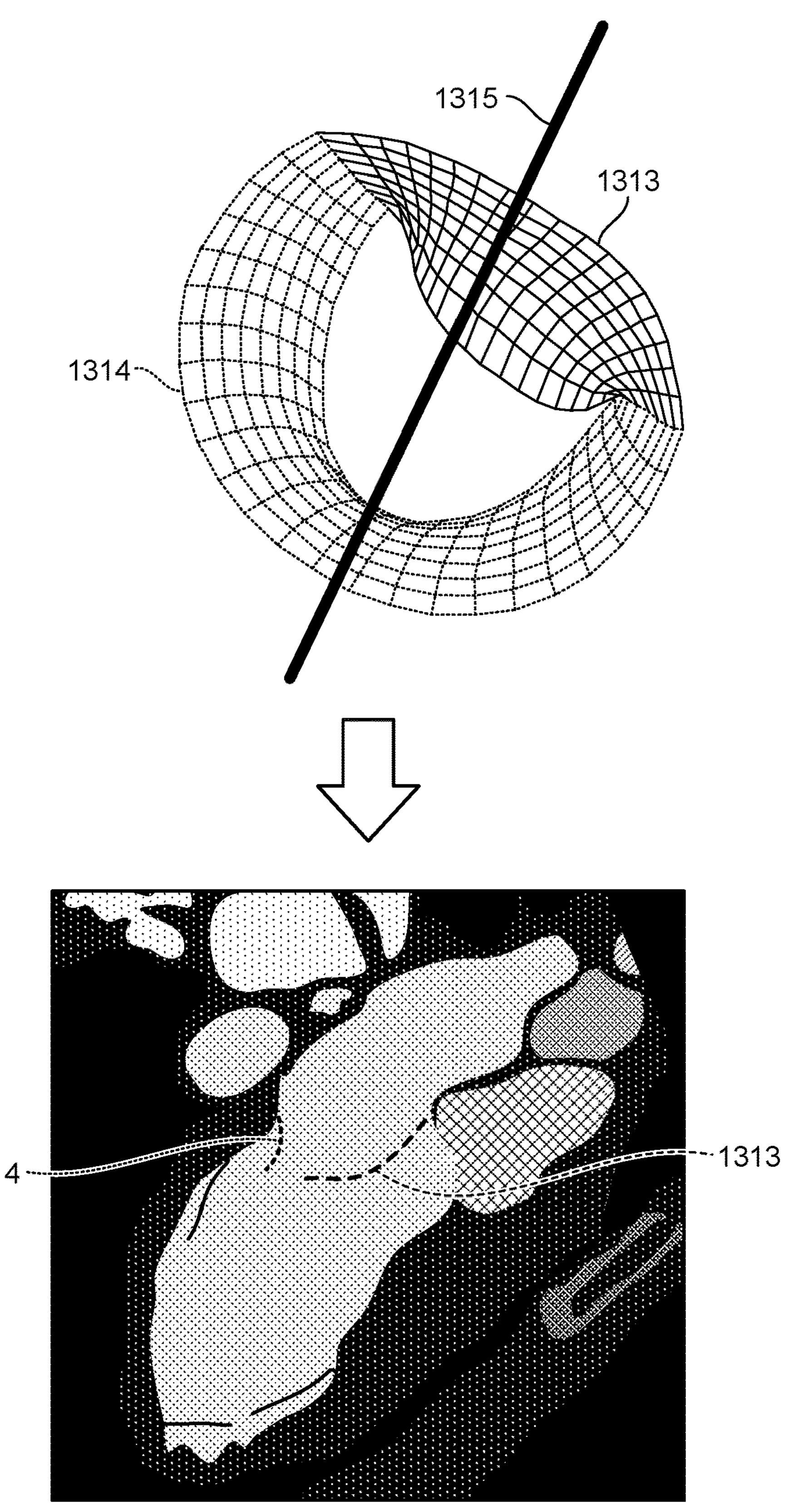
FIG. 13C is a diagram of an example of the GUI setting the Element of "Open Curve" according to the first embodiment.

FIG. 13B is an example of a GUI for setting an intersection area of any curved surface and any cross section as the Element of "Open Curve." The UI 1311 displays a list of Elements of "Plane" and the UI 1312 displays a list of Elements of "Curved Surface." By selecting one Element from each list, the user sets the open curve calculated from the Elements as the Element of "Open Curve." For example, the user selects a cross section 1315 illustrated in the upper drawing in FIG. 13C via the UI 1311 and selects an anterior leaflet 1313 and a posterior leaflet 1314 illustrated in the upper drawing in FIG. 13C via the UI 1312. The setting function 354 thereby calculates the intersection areas of the selected cross section 1315 and the selected curved surfaces (the anterior leaflet 1313 and the posterior leaflet 1314) (the open curve showing the anterior leaflet 1313 and the open curve showing the posterior leaflet 1314 illustrated in the lower drawing in FIG. 13C) and sets the calculated open curves as the Elements of "Open Curve."

Figure 13D:
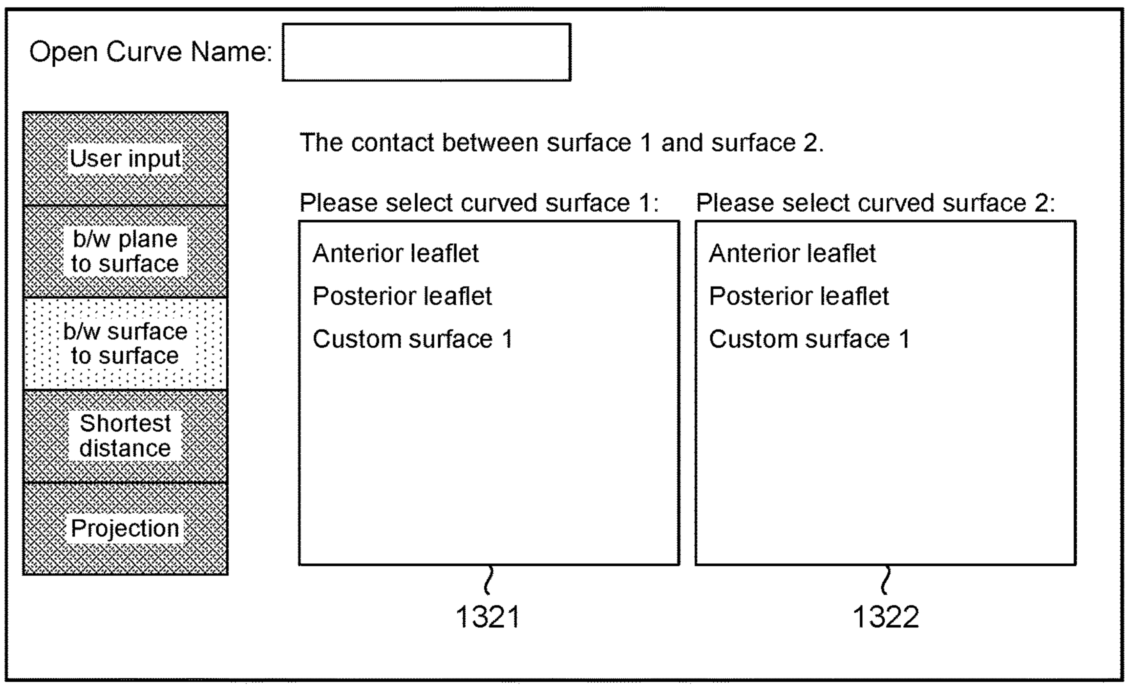
FIG. 13D is a diagram of an example of the GUI setting the Element of "Open Curve" according to the first embodiment.

FIG. 13D is an example of a GUI for setting an intersection area of any two different curved surfaces as the Element of "Open Curve." The UI 1321 and the UI 1322 display lists of Elements of "Curved Surface." By selecting one Element from each list, the user sets the open curve calculated from the Element as the Element of "Open Curve." That is, the user selects any curved surface in place of the cross section 1315 in the upper drawing in FIG. 13C, for example. The setting function 354 thereby calculates an intersection area (open curve) of the curved surface and the curved surface and sets the calculated open curve as the Element of "Open Curve".

Figure 13E:
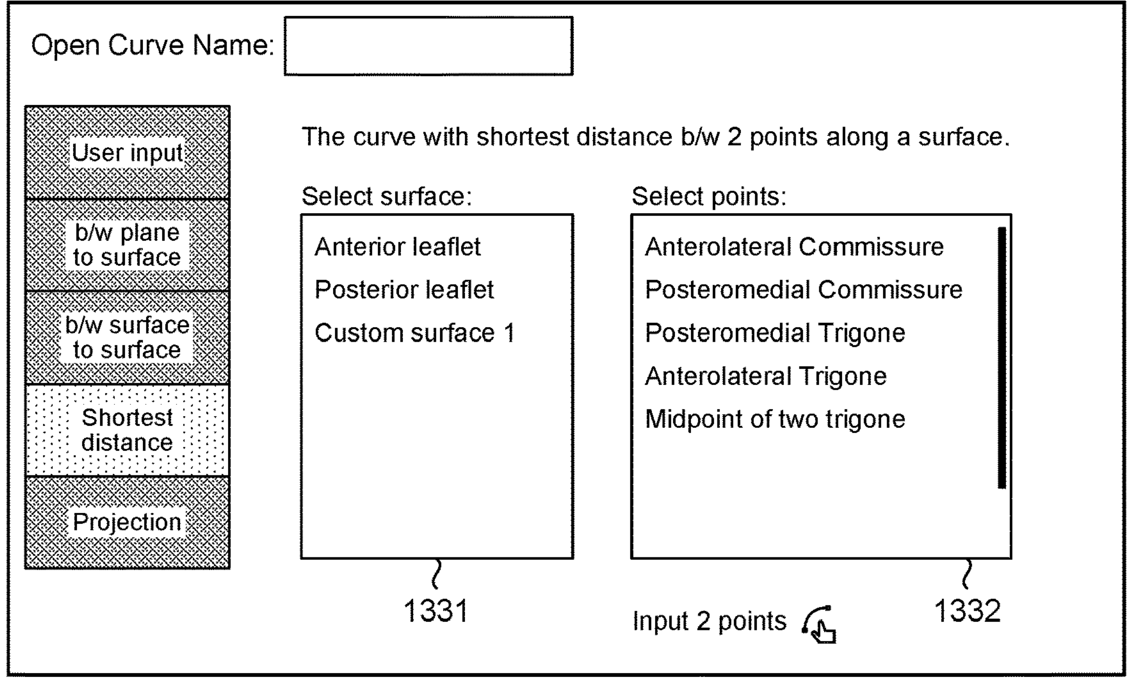
FIG. 13E is a diagram of an example of the GUI setting the Element of "Open Curve" according to the first embodiment.

FIG. 13E is an example of a GUI for selecting any curved surface and two points on the curved surface and setting a minimum curve along the curved surface with those two points as endpoints as the Element of "Open Curve." The UI 1331 displays a list of Elements of "Curved Surface." The user selects one Element from the list. The UI 1332 displays the Element of "Point" on "Curved Surface" selected by the user. The user selects two points from the Element. Any two grid points may be selected for the template displayed in the area 1060 in FIG. 10A by specifying them using the input interface 32.

Figure 13F:
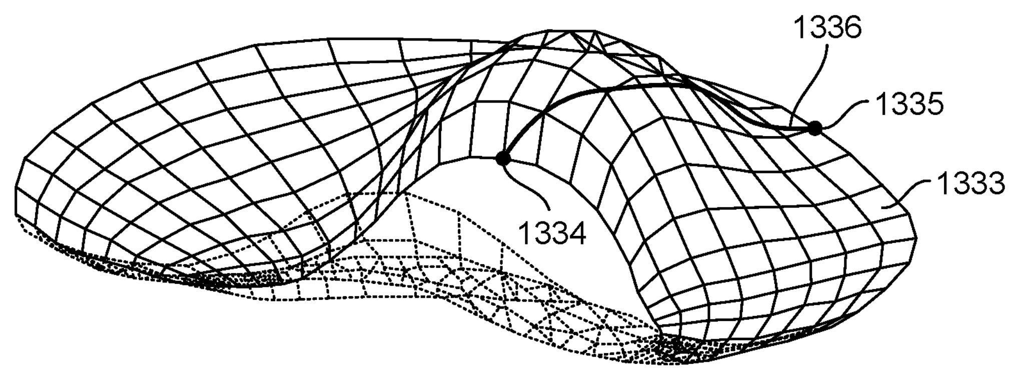
FIG. 13F is a diagram of an example of the GUI setting the Element of "Open Curve" according to the first embodiment.

For example, the user selects a posterior leaflet 1333 illustrated in FIG. 13F via the UI 1331 and selects a point 1334 and a point 1335 illustrated in FIG. 13F via the UI 1332. The setting function 354 thereby calculates a minimum curve 1336 along the curved surface of the posterior leaflet 1333 with the two selected points (the point 1334 and the point 1335) as end points and sets the calculated curve 1336 as the Element of "Open Curve."

Figure 13G:
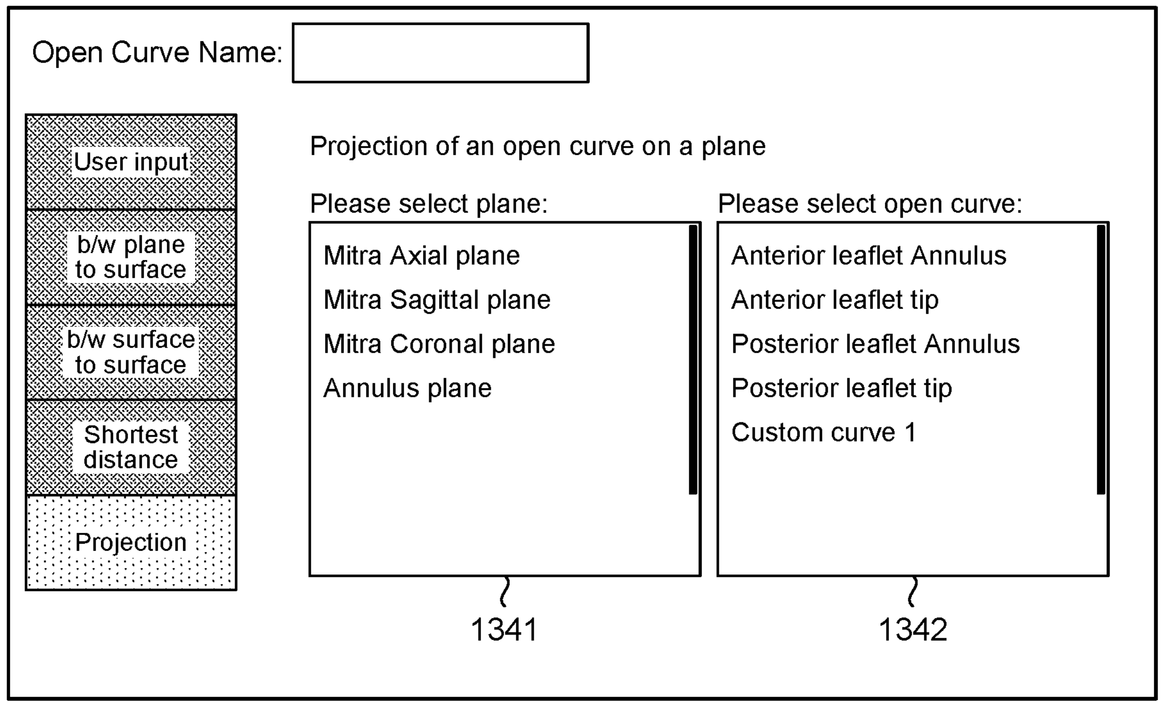
FIG. 13G is a diagram of an example of the GUI setting the Element of "Open Curve" according to the first embodiment.

FIG. 13G is an example of a GUI for setting an open curve formed by projecting any open curve onto any cross section as the Element of "Open Curve." The UI 1341 displays a list of Elements of "Plane," and thus the user selects one of them and sets it as a projection plane. The UI 1342 displays a list of Elements of "Open Curve," and thus the user selects one of them and sets it as the curve to be projected. The setting function 354 sets the open curve obtained by projecting the selected open curve onto the selected projection plane as the Element of "Open Curve."

The setting of the Element of "Open Curve" has been specifically described so far, but the embodiment is not limited to the GUIs described above. The Element of "Open Curve" may be set in any way so long as a specific curve can be set from the relation of the grid point group.

(Setting of Closed Curve)

Next, the following describes setting of the Element of "Closed Curve" using FIG. 14A to FIG. 14G. FIG. 14A to FIG. 14G are diagrams of examples of a GUI setting the Element of "Closed Curve" according to the first embodiment. FIG. 14A to FIG. 14G are screen examples corresponding to the area 1050 in FIG. 10A when "Closed Curve" of Add Element is selected in the area 1010.

Figures 14A, 14B:
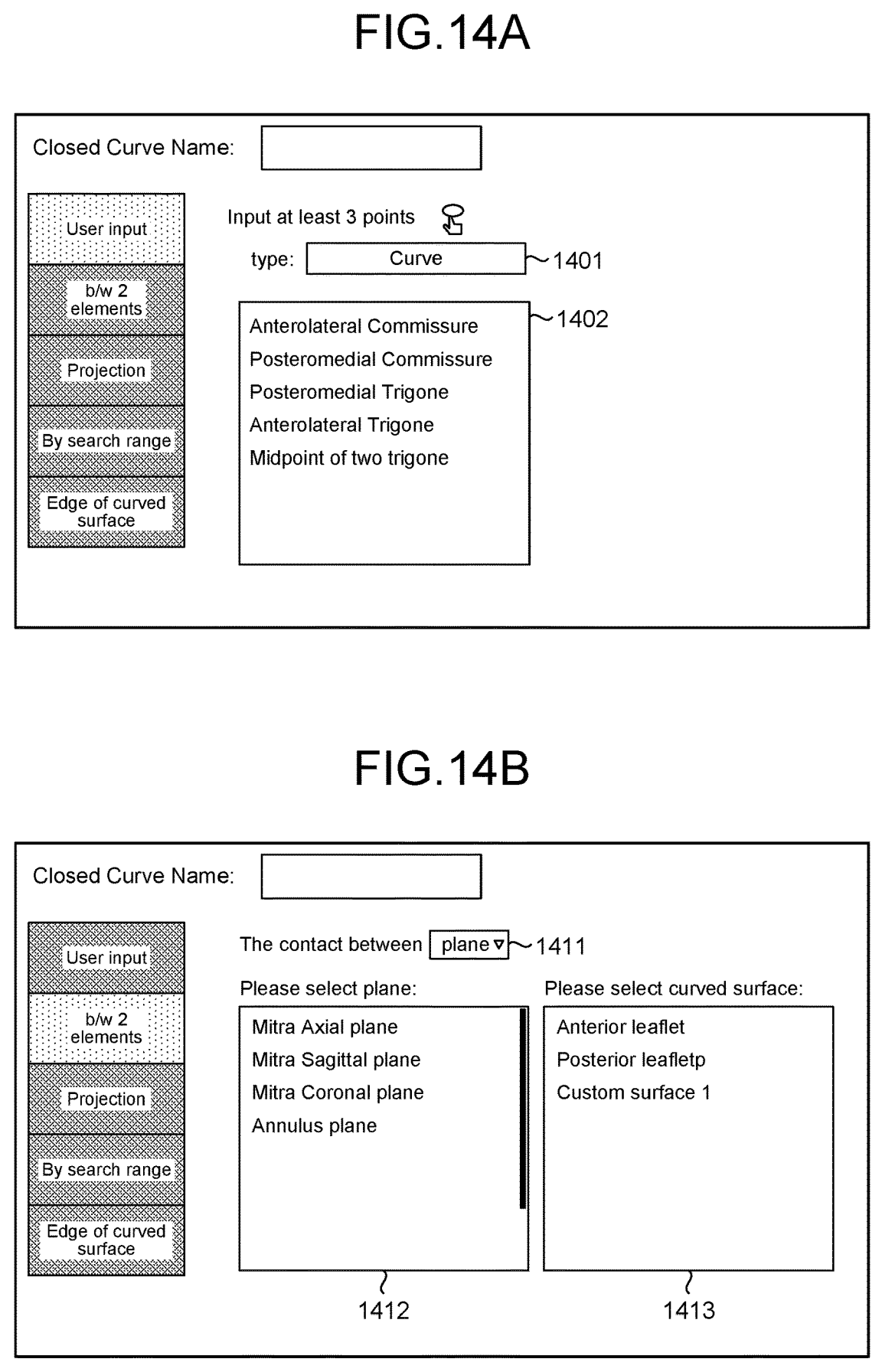

FIG. 14A is an example of a GUI for calculating a curve or polygon from any three or more points and setting it as the Element of "Closed Curve." The three or more points may be selected from a list of Elements of "Point" displayed in the UI 1402 or selected by specifying any grid points for the template displayed in the area 1060 in FIG. 10A using the input interface 32. The UI 1401 is a UI for selecting whether the line connecting the selected point group is to be "Curve" or "Straight Line." When "Straight Line" is selected, a polygon connecting the selected point group with straight lines in a certain order (the order of being set, for example) is set as the Element of "Closed Curve." When "Curve" is selected, the selected point group is interpolated using known curve approximation processing (spline curve, for example) to create a closed curve, which is set as the Element of "Closed Curve."

FIG. 14B is an example of a GUI for setting an intersection area of any plane and any curved surface or an intersection area of any two given different curved surfaces as the Element of "Closed Curve." The UI 1411 is a UI for selecting which of the setting of the intersection area of any plane and any curved surface or the setting of the intersection area of any two different curved surfaces is to be targeted. The UI 1412 displays a list of Elements corresponding to the type of the Element (plane or curved surface) selected in the UI 1411, and the UI 1413 displays a list of Elements of "Curved Surface." By selecting one Element from each list, the user sets the closed curve calculated from the Elements as the Element of "Closed Curve."

Figure 14C:
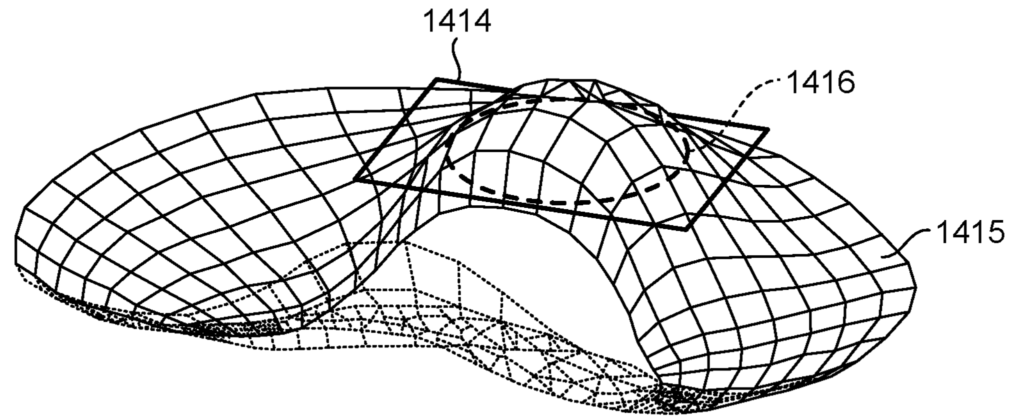
FIG. 14C is a diagram of an example of the GUI setting the Element of "Closed Curve" according to the first embodiment.

For example, the user selects a cross section 1414 illustrated in FIG. 14C via the UI 1412 and selects a posterior leaflet 1415 illustrated in FIG. 14C via the UI 1413. The setting function 354 thereby calculates the intersection area (a closed curve 1416) of the selected cross section 1414 and the curved surface of the posterior leaflet 1333 and sets the calculated closed curve 1416 as the Element of "Closed Curve."

Figure 14D:
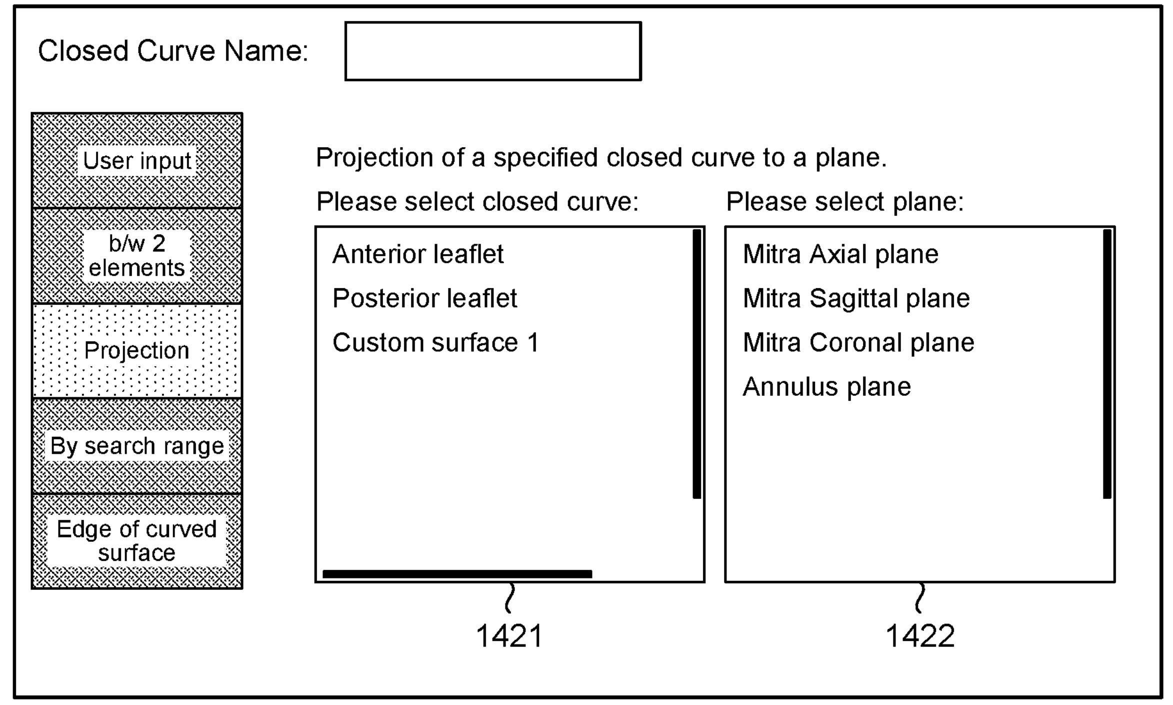
FIG. 14D is a diagram of an example of the GUI setting the Element of "Closed Curve" according to the first embodiment.

FIG. 14D is an example of a GUI for setting a closed curve obtained by projecting any closed curve onto any cross section as the Element of "Closed Curve." The UI 1422 displays a list of Elements of "Plane," and thus the user selects one of them and sets it as a projection plane. The UI 1421 displays a list of Elements of "Closed Curve," and thus the user selects one of them and sets it as the closed curve to be projected. The setting function 354 sets the closed curve obtained by projecting the selected closed curve onto the selected projection plane as the Element of "Closed Curve."

FIG. 14E is an example of a GUI for setting a closed curve indicating the contour of a cross section when any three-dimensional region has been cut at any position as the Element of "Closed Curve." The UI 1431 is a UI for selecting any three-dimensional region extracted in advance, and the UI 1436 presents options. The user specifies one three-dimensional region from the presented options. The UI 1432 to the UI 1435 set conditions for the cross section cutting the three-dimensional region. The UI 1432 designates a condition for the contour of the three-dimensional region when cut along the cross section and in FIG. 14E sets having the biggest perimeter as the condition. Having the smallest perimeter may be specified as the condition or having a perimeter (or area) that is a value nearest to any value may be specified as the condition.

The UI 1433 and the UI 1434 are UIs for setting conditions for a range in which the cross section is searched for, and the cross section satisfying other set conditions is searched for only in the region within the range surrounded by the UI 1433 and the UI 1434. The UI 1437 and the UI 1438 display lists of Elements of "Plane" as candidates for two cross sections for setting the range, and the user specifies one Element each. The UI 1435 is a UI for specifying another cross section when the cross section cutting the three-dimensional region is in parallel positional relation with the other cross section, and the UI 1439 displays a list of Elements of "Plane" as candidates for the other cross section in parallel positional relation. When specifying the cross section in parallel positional relation with the other cross section, the user specifies one Element from the UI 1439. Of course, this is only an example, and it may be possible to set any condition so long as it is a condition capable of easily identifying the cross section, such as perpendicular positional relation rather than parallel positional relation or being a certain distance apart.

The use of the condition settings by the UI 1433 to the UI 1435 facilitates the identification of the cross section, but the conditions in the UI 1433 to the UI 1435 are not necessarily necessary, and any method is acceptable so long as the cross section satisfying the condition can be identified based on a predefined method of processing. The setting function 354 sets the closed curve corresponding to the contour of the selected region on the cross section satisfying the condition as the Element of "Closed Curve."

Figures 14F, 14G:
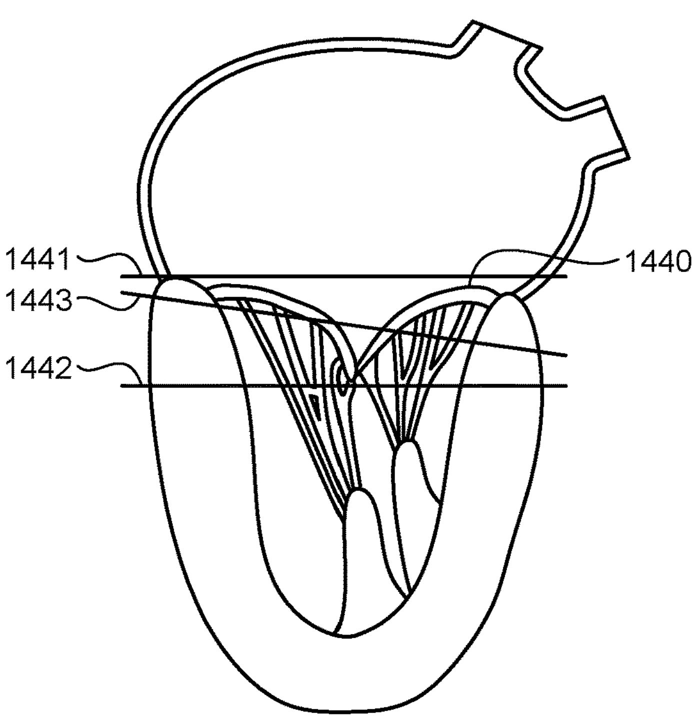
FIG. 14F is a diagram of an example of the GUI setting the Element of "Closed Curve" according to the first embodiment.
FIG. 14G is a diagram of an example of the GUI setting the Element of "Closed Curve" according to the first embodiment.

For example, the user specifies a three-dimensional region including a mitral valve 1440 illustrated in FIG. 14F via the UI 1431 and the UI 1436. FIG. 14F schematically illustrates the mitral valve 1440 and surrounding regions, but in reality, these three-dimensional regions are extracted as a mesh. The user then selects a cross section 1441 and a cross section 1442 illustrated in FIG. 14F via the UI 1433 and the UI 1434 and sets the range in which the cross section is searched for.

The setting function 354 identifies a cross section having the largest perimeter of the contour of the cross section when the three-dimensional region is cut in a cross section 1443 that can be set in the range between the cross section 1441 and the cross section 1442 and sets a closed curve indicating the contour of the three-dimensional region in the identified cross section as the Element of "Closed Curve."

FIG. 14G is an example of a GUI for setting the contour of any closed curved surface as the Element of "Closed Curve." The user selects any one Element from the list of Elements of "Curved Surface" displayed in the UI 1452, and the contour of the Element is set as the Element of "Closed Curve." If there are a plurality of closed curved surfaces in the contour of the selected Element (in the case of a cylindrical shape, the contour can be taken at the upper end and the lower end of the cylinder, for example), each of them may be listed. Alternatively, it may be controlled such that the corresponding contour is displayed in the area 1060 in FIG. 10A, and the contours are displayed one after another using the button 1451 to allow the user to display an appropriate contour.

The setting of the Element of "Closed Curve" has been specifically described so far, but the embodiment is not limited to the GUIs described above. The Element of "Closed Curve" may be set in any way so long as a specific closed curve can be set from the relation of the grid point group.

(Setting of Plane)

Next, the following describes setting of the Element of "Plane" using FIG. 15A to FIG. 15D. FIG. 15A to FIG. 15D are diagrams of examples of a GUI setting the Element of "Plane" according to the first embodiment. FIG. 15A to FIG. 15D are screen examples corresponding to the area 1050 in FIG. 10A when "Plane" of Add Element is selected in the area 1010.

Figure 15A:
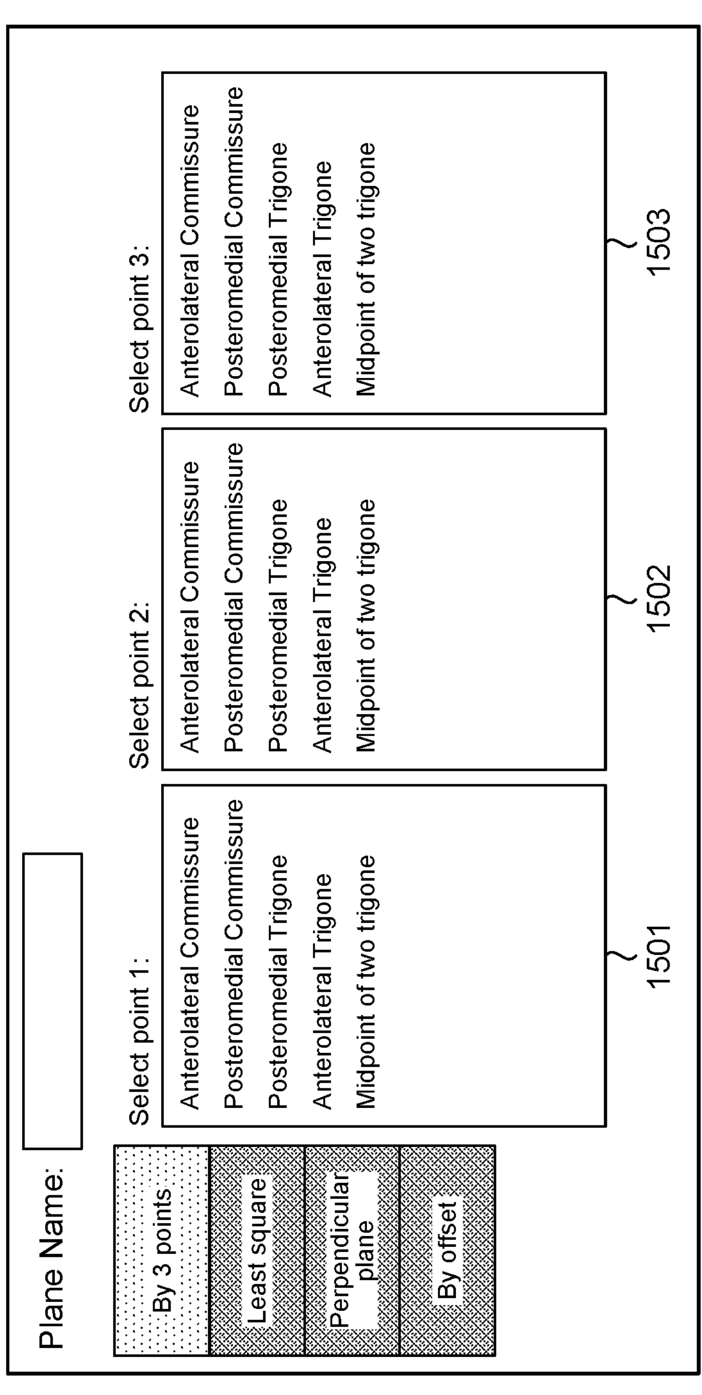
FIG. 15A is a diagram of an example of a GUI setting the Element of "Plane" according to the first embodiment.

FIG. 15A is an example of a GUI for setting a cross section passing through any three points as the Element of "Plane." The UI 1501 to the UI 1503 each display a list of Elements of "Point," and the user selects one Element from each list to automatically identify the cross section passing through the three points and sets the identified cross section as the Element of "Plane." In selecting the Element from each list, it may be controlled such that a warning is displayed when the same Element is selected, or it may be controlled such that the already selected Element is deleted from the list so that the same Element cannot be selected. It may also be controlled such that three points on the same straight line cannot be specified.

Figure 15B:
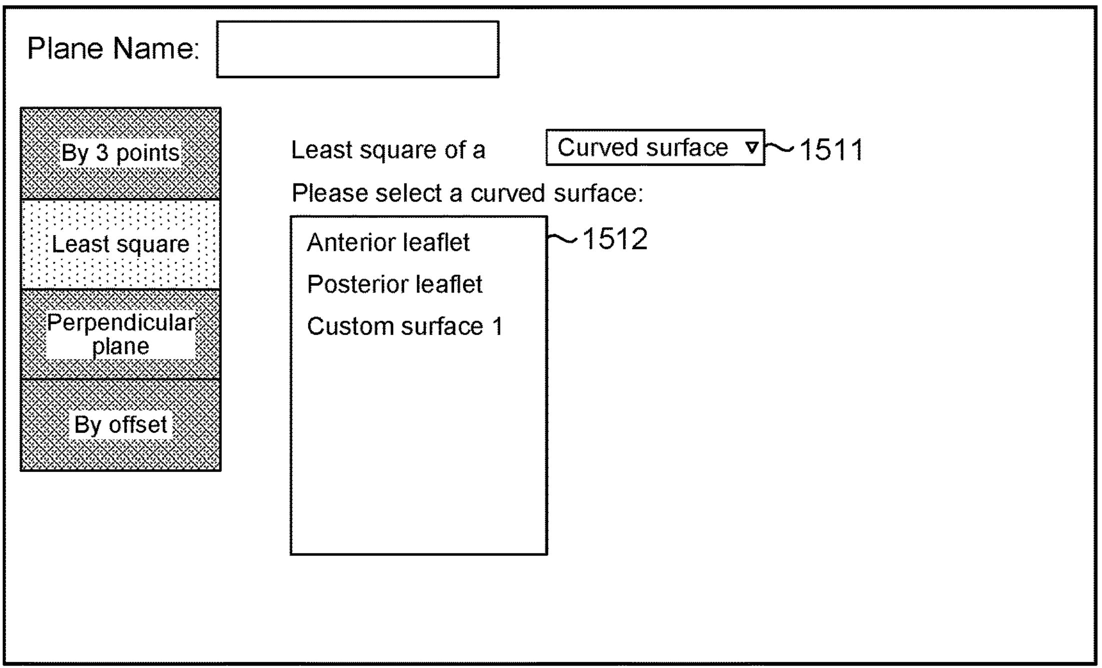
FIG. 15B is a diagram of an example of the GUI setting the Element of "Plane" according to the first embodiment.

FIG. 15B is an example of a GUI for setting a least-squares plane for any open curve, closed curve, or closed curved surface as the Element of "Plane." The UI 1511 is a UI selecting the type of the Element (open curve, closed curve, or closed curved surface), and the UI 1512 displays a list of corresponding Elements in response to selection by the user. The user selects one Element from the list. The setting function 354 automatically calculates the least-squares plane of the selected Element and sets the plane as the Element of "Plane."

Figure 15C:
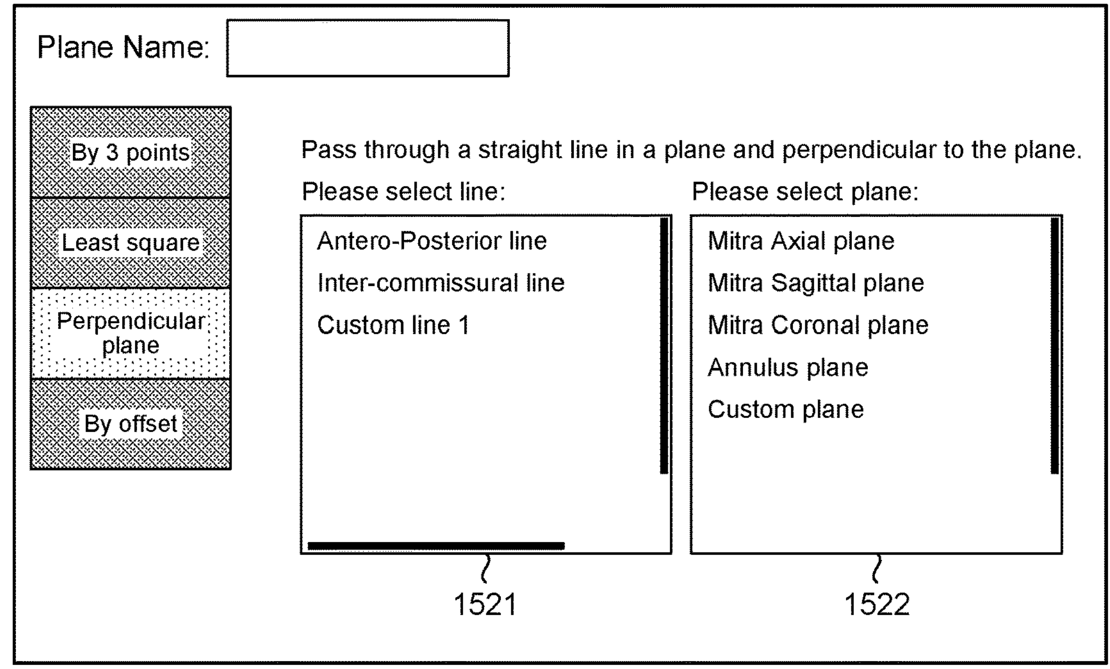
FIG. 15C is a diagram of an example of the GUI setting the Element of "Plane" according to the first embodiment.

FIG. 15C is an example of a GUI for setting a plane passing through any straight line and perpendicular to any plane as the Element of "Plane." The UI 1521 displays a list of Elements of "Line" and the UI 1522 displays a list of Elements of "Plane." The user selects one Element from each list. The setting function 354 sets the plane passing through the selected Element of "Line" and perpendicular to the selected Element of "Plane" as the Element of "Plane." Instead of the Element of "Line," two Elements of "Point" may be allowed to be selected.

Figure 15D:
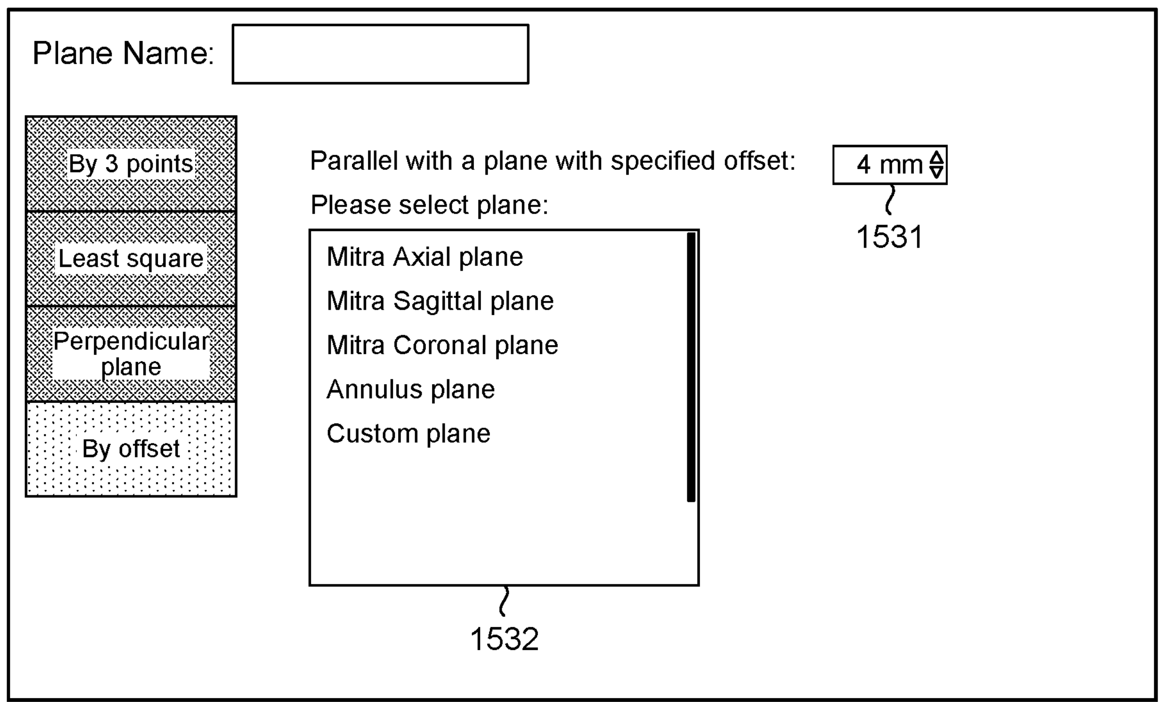
FIG. 15D is a diagram of an example of the GUI setting the Element of "Plane" according to the first embodiment.

FIG. 15D is an example of a GUI for setting a plane parallel to any plane and at a position spaced apart therefrom by any distance as the Element of "Plane." The UI 1531 is a UI for setting any distance, and the user inputs any distance using the input interface 32. The UI 1532 displays a list of Elements of "Plane," and the user selects one Element from the list. The setting function 354 sets the plane parallel to the selected Element of "Plane" and at a position spaced apart therefrom by any distance that has been set as the Element of "Plane."

The setting of the Element of "Plane" has been specifically described so far, but the embodiment is not limited to the GUIs described above. The Element of "Plane" may be set in any way so long as a specific plane can be set from the relation of the grid point group.

(Setting of Curved Surface)

Next, the following describes setting of the Element of "Curved Surface" using FIG. 16A to FIG. 16D. FIG. 16A to FIG. 16D are diagrams of examples of a GUI setting the Element of "Curved Surface" according to the first embodiment. FIG. 16A to FIG. 16D are screen examples corresponding to the area 1050 in FIG. 10A when "Curved Surface" of Add Element is selected in the area 1010.

Figure 16A:
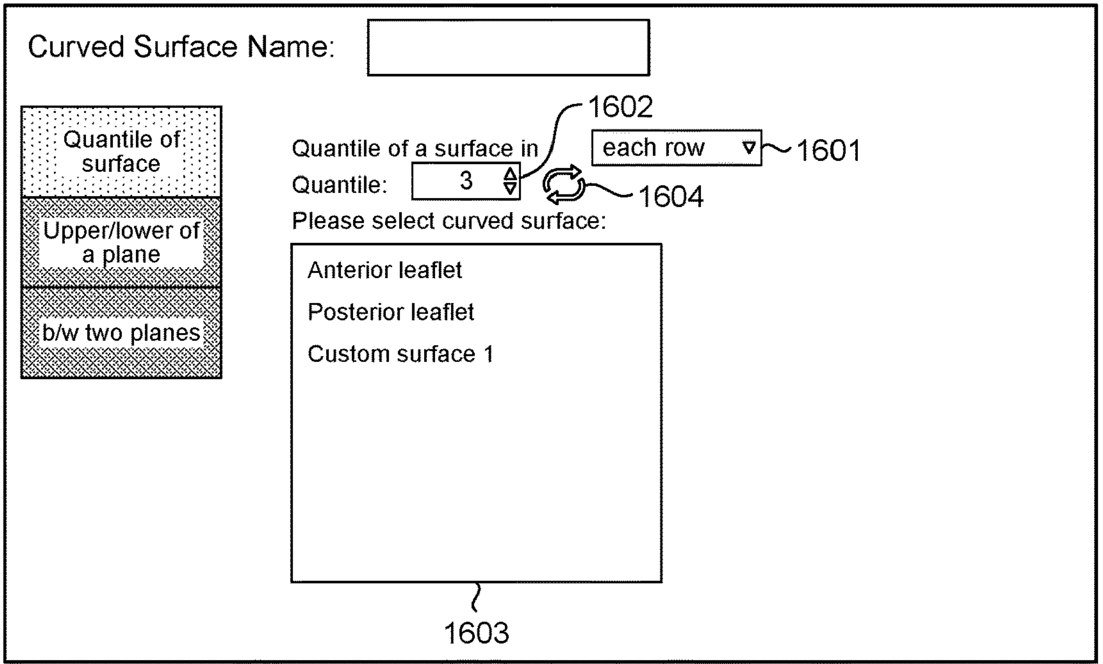
FIG. 16A is a diagram of an example of a GUI setting the Element of "Curved Surface" according to the first embodiment.

FIG. 16A is an example of a GUI for setting a curved surface at any quantile position on any curved surface as the Element of "Curved Surface" That is, FIG. 16A is a GUI for setting a curved surface formed by dividing any curved surface at any quantile position and receives specification of the curved surface to be divided and specification of the quantile position.

The UI 1603 displays a list of Elements of "Curved Surface," and the user selects one Element. The UI 1601 and the UI 1602 are UIs for specifying the quantile position in the selected Element, and the user specifies any position via the UI 1601 and the UI 1602. When the curved surface is divided at any quantile position, a plurality of curved surfaces are formed. The user can sequentially switch between the formed curved surfaces by means of the button 1604. The setting function 354 sets the curved surface specified by the user as the Element of "Curved Surface."

Figure 16B:
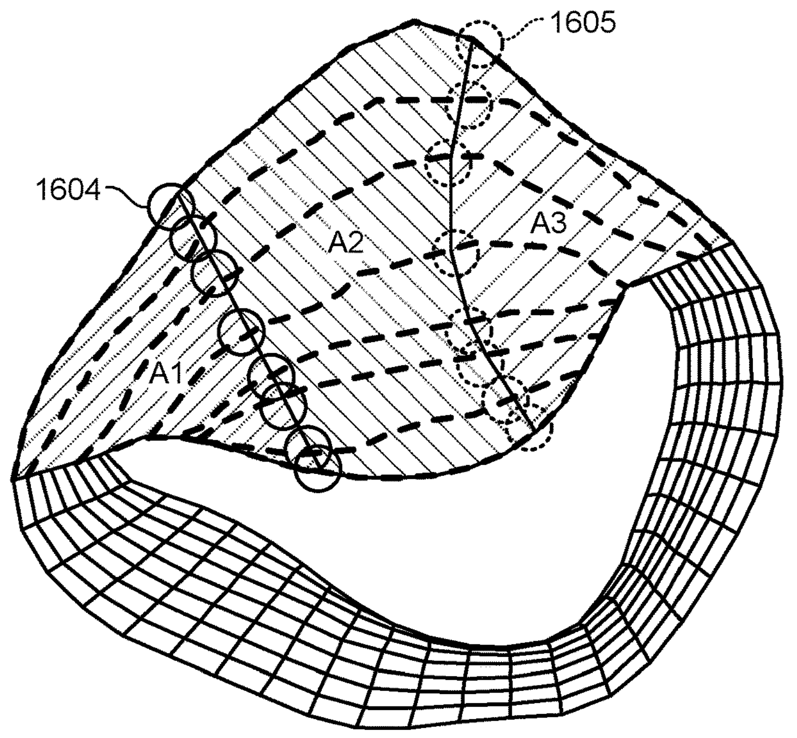
FIG. 16B is a diagram of an example of the GUI setting the Element of "Curved Surface" according to the first embodiment.

For example, the user specifies the anterior leaflet of the mitral valve as the curved surface to be divided via the UI 1603. Then, by operating the UI 1601 and the UI 1602, as illustrated in FIG. 16B, the user specifies a position 1064 with 3 quantiles and a position 1605 with 6 quantiles in the column direction, for example. The setting function 354 thereby calculates a curved surface A1, a curved surface A2, and a curved surface A3 obtained by dividing the anterior leaflet of the mitral valve at the above quantile positions and sets the calculated curved surfaces as the Elements of "Curved Surface." Only a curved surface selected by the user from the curved surfaces may be set as the Element of "Curved Surface."

Figure 16C:
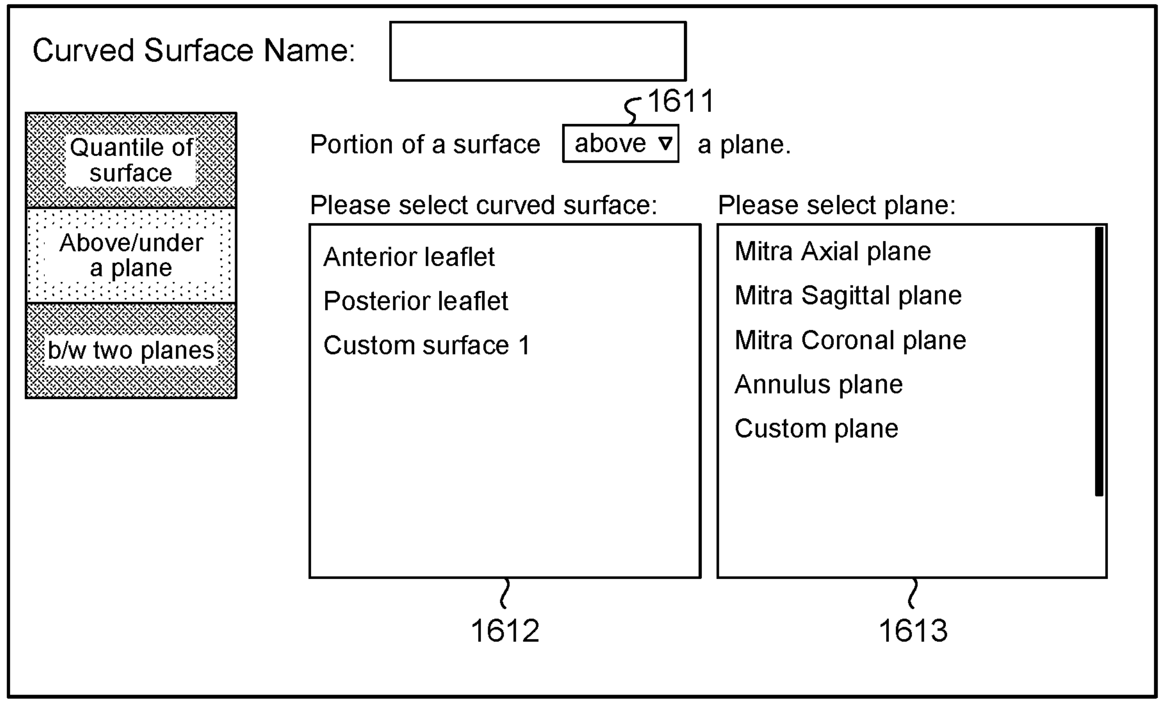
FIG. 16C is a diagram of an example of the GUI setting the Element of "Curved Surface" according to the first embodiment.

FIG. 16C is an example of a GUI for setting a partial curved surface of any curved surface positioned above or below any plane as the Element of "Curved Surface." The UI 1612 displays a list of Elements of "Curved Surface," and the user selects one Element from the list. The UI 1613 displays a list of Elements of "Plane," and the user selects one Element from the list. The UI 1611 is a UI for selecting whether the selected curved surface is positioned above the selected plane or positioned therebelow, and the user selects either of them. The setting function 354 sets the curved surface existing on the selected side of the selected Element of "Plane" in the selected Element of "Curved Surface" as the Element of "Curved Surface."

Figure 16D:
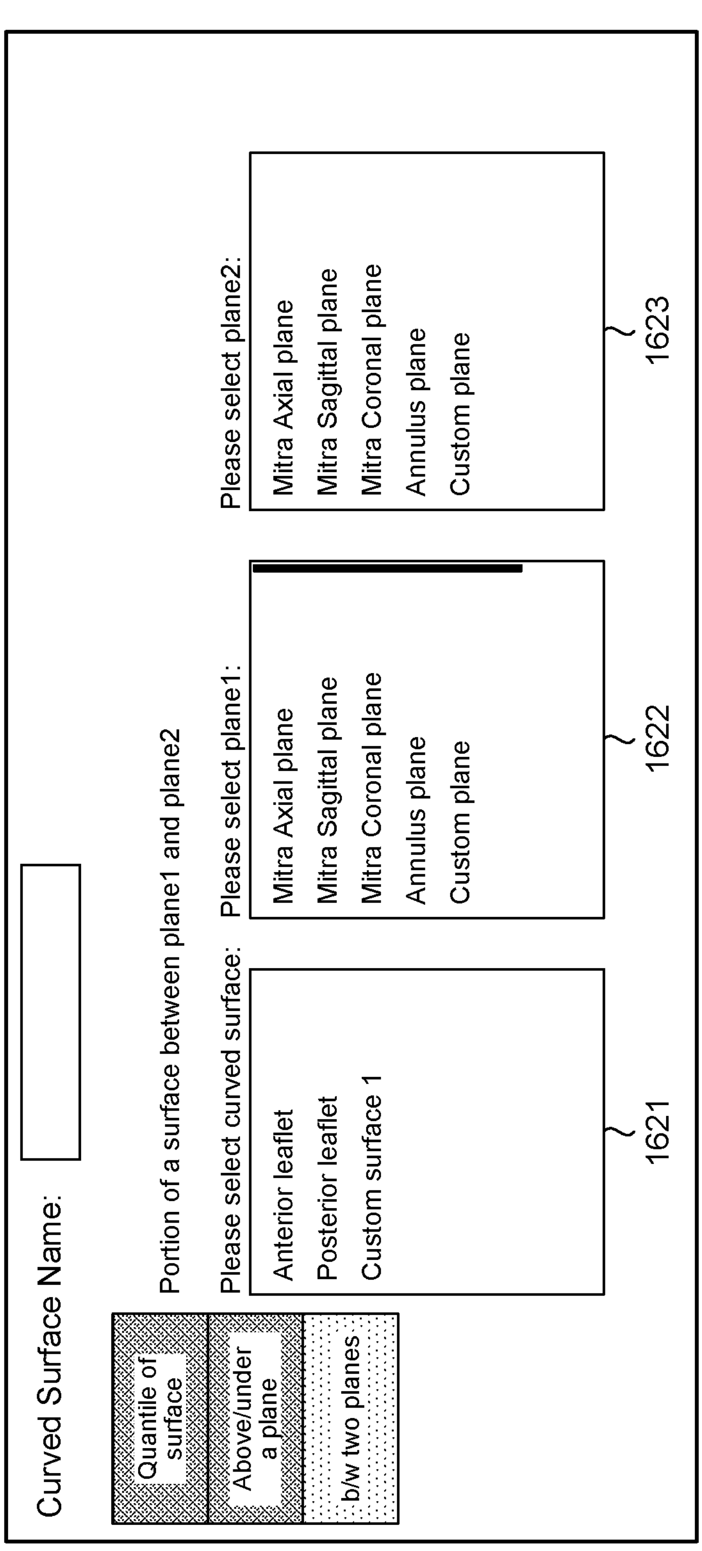
FIG. 16D is a diagram of an example of the GUI setting the Element of "Curved Surface" according to the first embodiment.

FIG. 16D is an example of a GUI for setting a partial curved surface of any curved surface surrounded by any plane as the Element of "Curved Surface." The UI 1621 displays a list of Elements of "Curved Surface," and the user selects one element from the list. The UI 1622 and the UI 1623 display lists of Elements of "Plane," and the user selects one Element each from the lists. The setting function 354 sets the curved surface positioned between the two selected Elements of "Plane" in the selected Element of "Curved Surface" as the Element of "Curved Surface."

Various nonlinear fitting functions for forming curved surfaces are known (polynomials in the Chebyshev series, polynomials in the Cos series, nonlinear logistic dose response functions, nonlinear exponential functions, and nonlinear extreme value functions, for example). The medical image processing apparatus 3 may cause the user to select any of these fitting functions and receive specification of required parameters and a required number of grid points for the selected function to set any curved surface desired by the user from the grid point group of the analysis target. In such a case, the medical image processing apparatus 3 may include a GUI enabling such settings.

The setting of the Element of "Curved Surface" has been specifically described so far, but the embodiment is not limited to the GUIs described above. The Element of "Curved Surface" may be set in any way so long as a specific plane can be set from the relation of the grid point group.

Methods for setting various Elements have been specifically described so far, but the type of the Element is not limited to these examples, and it may be possible to set any information as the Element so long as it takes a kind of form that can be set from the grid point group or the characteristic points (the characteristic points based on the grid point group or the anatomical characteristic points). In the drawings, examples in which only the Elements related to the mitral valve are listed have been described, but Elements for a plurality of anatomical structures may be listed simultaneously, or it may be possible to switch among them.

Next, the following describes a method for setting a measurement item using the set Element using FIG. 17A to FIG. 17D. FIG. 17A to FIG. 17D are diagrams of examples of a GUI setting the measurement item according to the first embodiment. The following describes a method for setting the calculation rule for each of "Direct Distance," "Open Curve," "ROI," "Angle," and "VOI" together with examples of the GUI. Settings for Direct Distance For "Direct Distance," an example in which two Elements are specified and the distance between the Elements is calculated was described using FIG. 10A. As another method, for example, the Element of "Line" may be specified, and the length of the Line may be calculated. In such a case, a line segment corresponding to the minimum distance between the two Elements is registered as the Element of "Line."

Settings for Open Curve

Figure 17A:
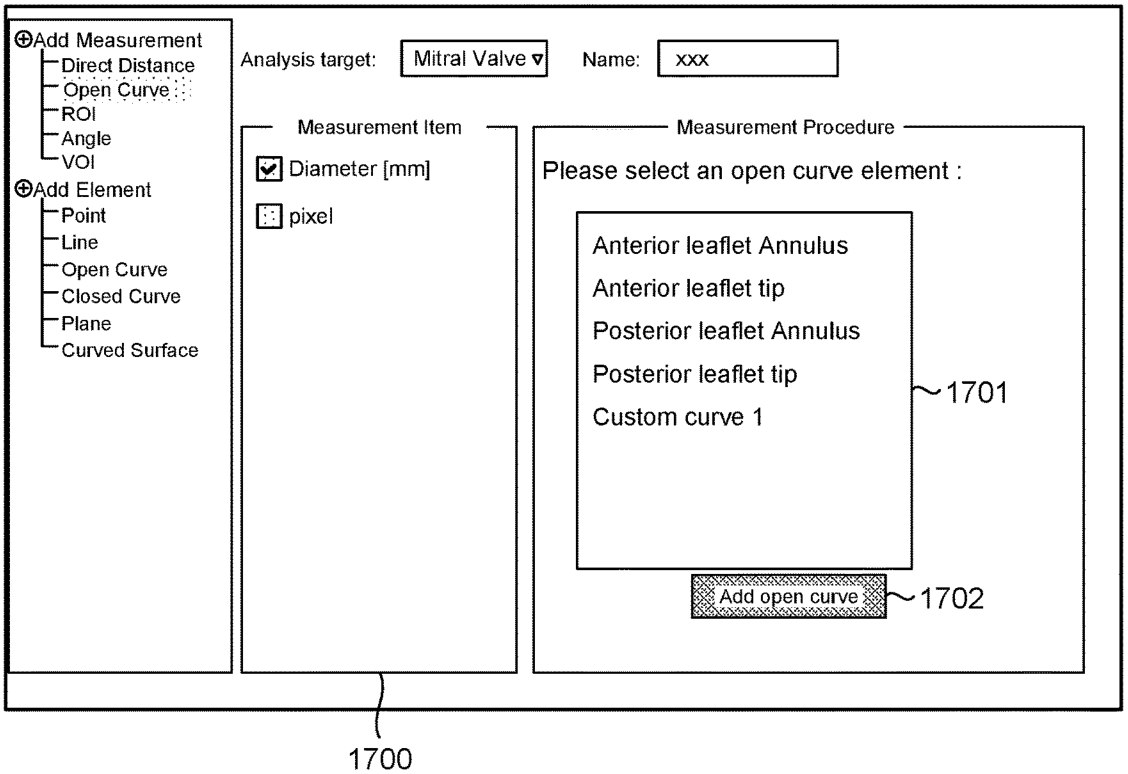
FIG. 17A is a diagram of an example of a GUI setting a measurement item according to the first embodiment.

FIG. 17A is a screen example corresponding to the area 1010, the area 1040, and the area 1050 in FIG. 10A when "Open Curve" of Add Measurement is selected in the area 1010. The area 1700 displays choices "Diameter [mm]" and "pixel" like Measurement Item displayed in the area 1040 of "Direct Distance" in FIG. 10A. These items are identical to those of Direct Distance, and thus a detailed description is omitted.

The area 1701 displays a list of Elements of "Open Curve," and the user selects one of them to set the calculation rule calculating the measurement item selected in the area 1700 at the position corresponding to the Element of "Open Curve" selected in the area 1701. If the desired Element is not present in the list, the user adds the Element before setting the calculation rule as in the area 1010 in FIG. 10A. The button 1702 is a button to transition to the same screen as when "Open Curve" of "Add Element" is selected.

Settings for ROI

Figure 17B:
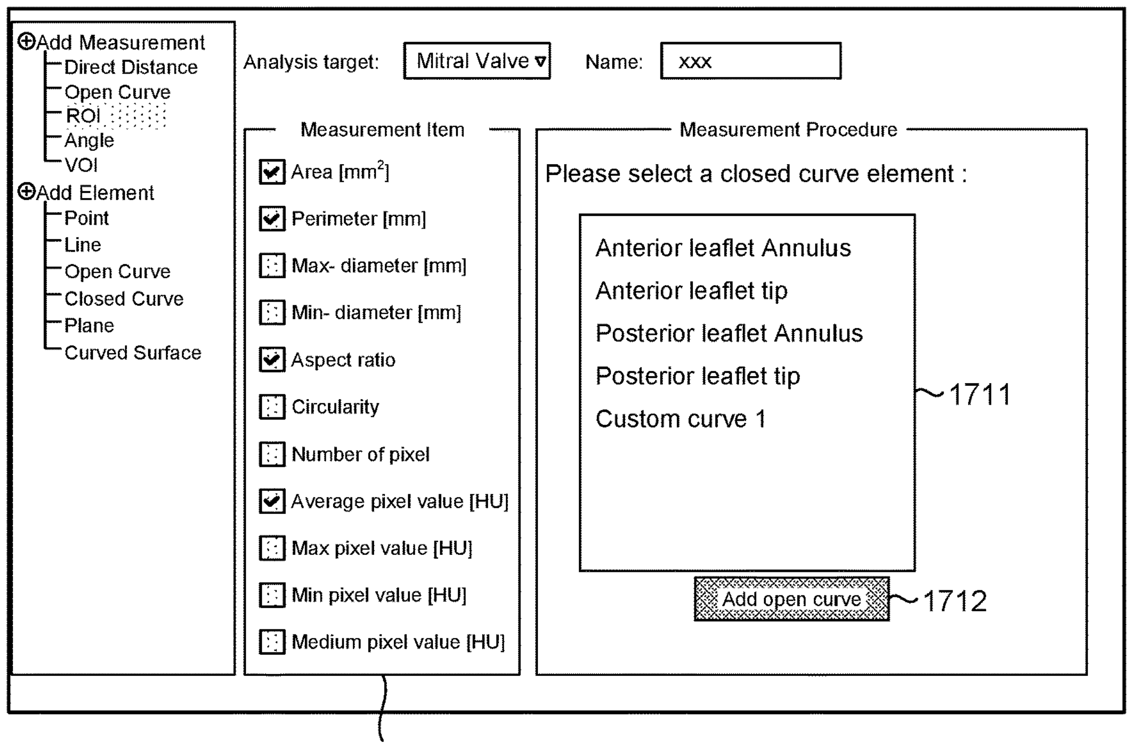
FIG. 17B is a diagram of an example of the GUI setting the measurement item according to the first embodiment.

FIG. 17B is a screen example corresponding to the area 1010, the area 1040, and the area 1050 in FIG. 10A when "ROI" of Add Measurement is selected in the area 1010. The area 1710 displays the measurement item corresponding to area, perimeter, maximum diameter, minimum diameter, aspect ratio, circularity, number of pixels, average pixel value, maximum pixel value, minimum pixel value, and medium pixel value as options as the measurement item for ROI. In FIG. 17B, area, perimeter, aspect ratio, and average pixel value are selected. The area 1711 displays a list of Elements of "Closed Curve," and the user selects one of them to set the calculation rule calculating the measurement item selected in the area 1710 at the position corresponding to the Element of "Closed Curve" selected in the area 1711. If the desired Element is not present in the list, the user adds the Element before setting the calculation rule as in the area 1010 in FIG. 10A. The button 1712 is a button to transition to the same screen as when "Closed Curve" of "Add Element" is selected.

Settings for Angle

Figure 17C:
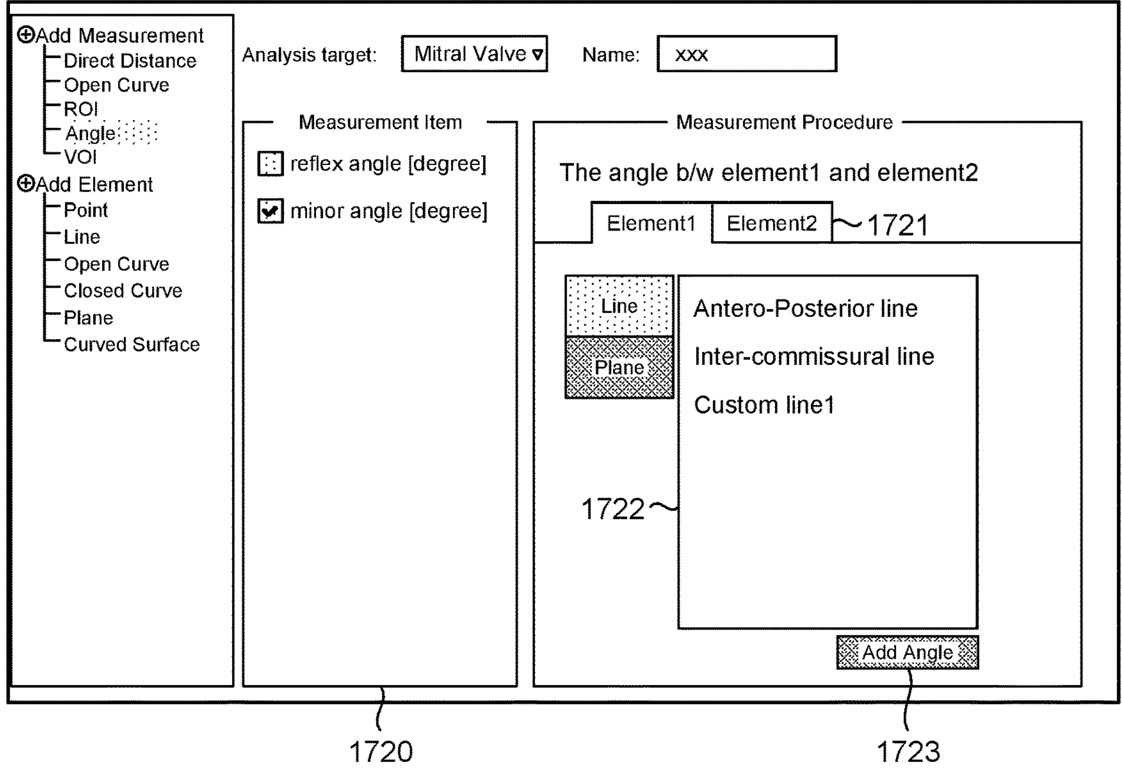
FIG. 17C is a diagram of an example of the GUI setting the measurement item according to the first embodiment.

FIG. 17C is a screen example corresponding to the area 1010, the area 1040, and the area 1050 in FIG. 10A when "Angle" of Add Measurement is selected in the area 1010. The area 1720 displays reflex angle (angle greater than 180 degrees) and minor angle (angle smaller than 180 degrees) as options as the measurement item for Angle, with minor angle being selected. Angle can be calculated as an angle formed by two Elements of line or plane. Thus, the area corresponding to the area 1050 is a UI in which two Elements can be selected from Elements of "Line" and "Plane." The setting of the two Elements can be switched by the tab 1721.

The area 1722 displays a list of Elements of selected "Line" or "Plane." By selecting the two Elements forming Angle, the user sets the calculation rule calculating the measurement item selected in the area 1720 for the angle formed by the two Elements selected in the area 1722. If the desired Element is not present in the list, the user adds the Element before setting the calculation rule as in the area 1010 in FIG. 10A. The button 1723 is a button to transition to the same screen as when "Angle" of "Add Element" is selected.

Settings for VOI

Figure 17D:
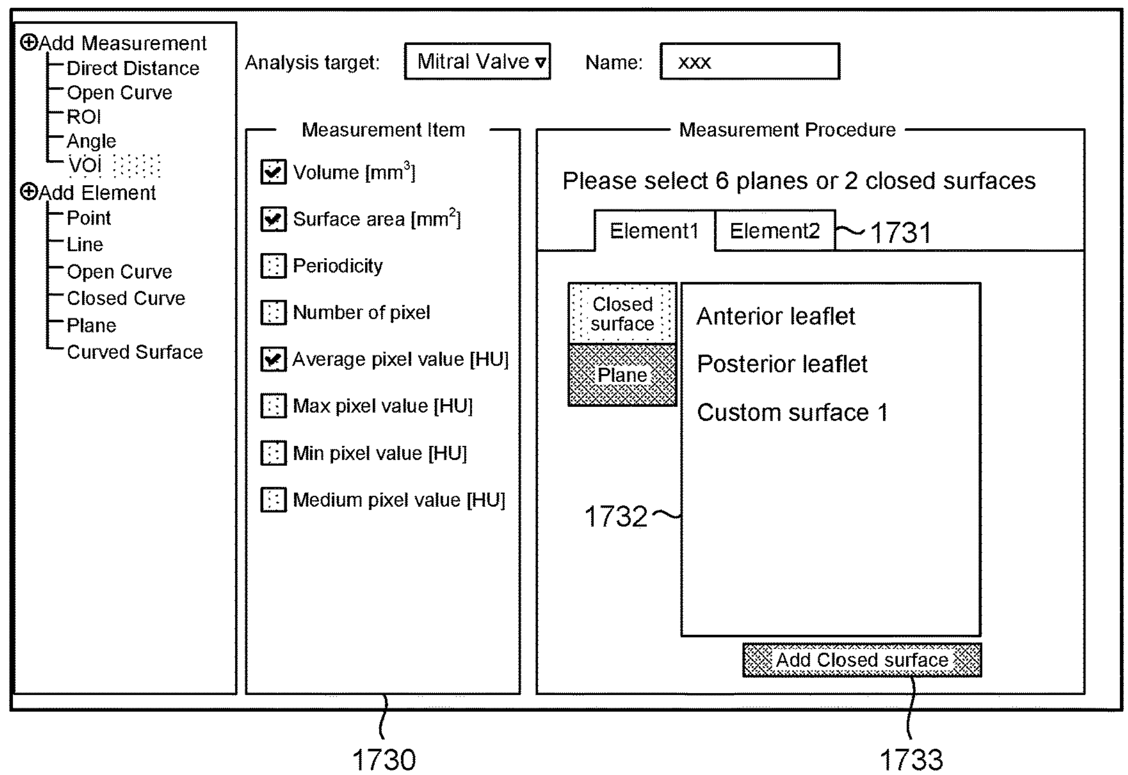
FIG. 17D is a diagram of an example of the GUI setting the measurement item according to the first embodiment.

FIG. 17D is a screen example corresponding to the area 1010, the area 1040, and the area 1050 in FIG. 10A when "VOI" of Add Measurement is selected in the area 1010. The area 1730 displays the measurement item corresponding to volume, surface area, sphericity, number of pixels, average pixel value, maximum pixel value, minimum pixel value, and medium pixel value as options as the measurement item for VOI. In FIG. 17D, area, surface area, and average pixel value are selected. VOI is defined as a region surrounded by a plurality of Elements, and the measured value of each measurement item can be calculated for the region.

In FIG. 17D, the area corresponding to the area 1050 is a GUI that can set either six Elements of "Plane" or two curved surfaces, but it may be another GUI. For example, it may be possible to select four Planes or to set three or more curved surfaces. Determination may be disabled until the region surrounded by the Elements to be selected is determined to be one. The Element may be selected from defined grid point groups (those corresponding to 1070 in FIG. such as Aortic root, LA, LV, RA, or RV, for example). In FIG. 17D, "Closed Surface" is selected, and thus the setting of the two Elements can be switched in the tab 1731. When "Plane" is selected, it may be possible to display six tabs and to set six Elements. The area 1732 displays a list of Elements of selected "Closed Surface" or "Plane." The user sets the calculation rule calculating the measurement item selected in the area 1730 for VOI prescribed by a plurality of Elements selected in the area 1732. If the desired Element is not present in the list, the user adds the Element before setting the calculation rule as in the area 1010 in FIG. 10A. The button 1733 is a button to transition to the same screen as when "Closed Surface" of "Add Element" is selected.

As described above, in the present embodiment, the measurement target is configured by the Element, and the measurement item is set for the configured target to set a new measurement item. As described above, the Element includes a figure element such as "Point," "Line," "Open Curve," "Closed Curve," "Plane," or "Cureved Surface." That is, the medical image processing apparatus 3 according to the present embodiment can set various calculation rules by a combination of the figure element and the measurement item (a calculation item). Specifically, the control function 351 receives the figure element to be applied to the region of interest and the calculation item in the region of interest. The setting function 354 then sets the calculation rule based on a combination of the figure element and the calculation item received by the control function 351.

Methods for setting various calculation rules based on the Element have been described in details, but the type of the calculation rule is not limited to this example, and the calculation rule may be set in any way so long as it takes a kind of form that can be set from the Element. In the drawings, examples in which only the Elements related to the mitral valve are listed have been described, but Elements for a plurality of anatomical structures may be listed simultaneously, or it may be possible to switch among them.

Figure 18:
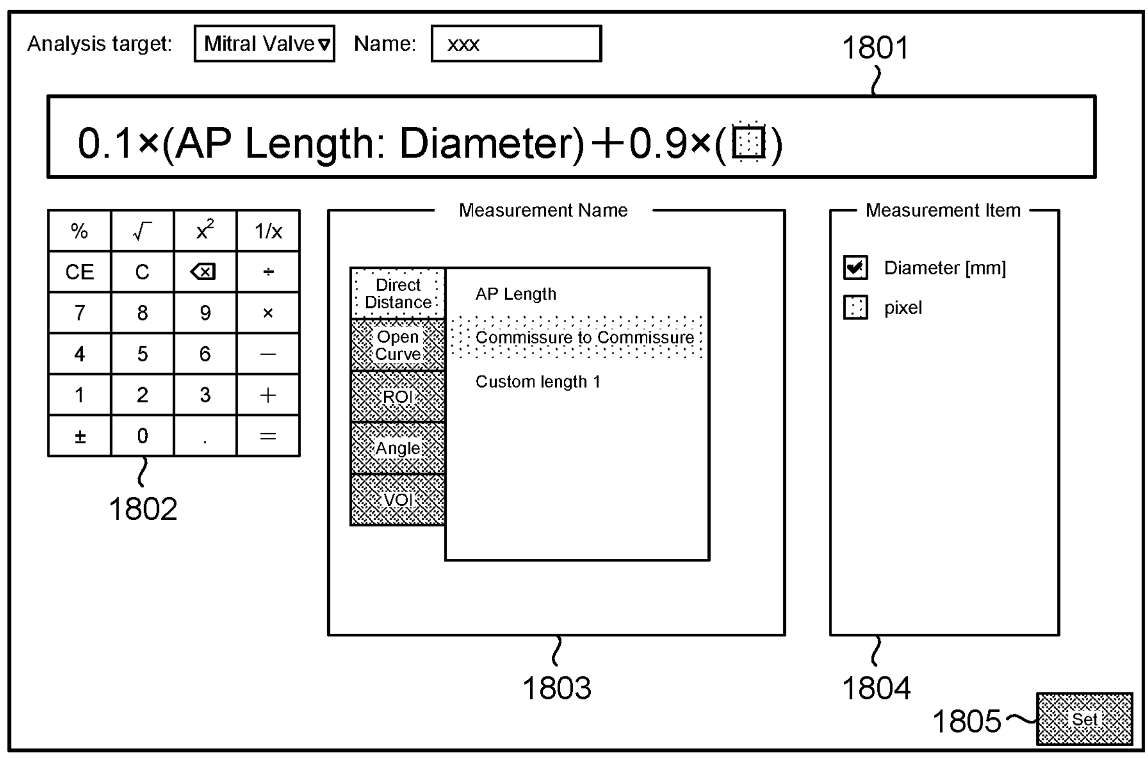
FIG. 18 is a diagram of an example of the GUI setting the measurement item according to the first embodiment.

It may be possible to set the calculation item (the calculation rule) with a plurality of calculation items integrated with each other. FIG. 18 is a diagram of an example of the GUI setting the measurement item according to the first embodiment. FIG. 18 illustrates a GUI integrating the calculation items using commonly known calculation rules such as four arithmetic operations. The area 1801 is an area displaying the calculation rule to be created, and the calculation rule is set using measurement items, numerical values, and operators specified by the area 1802 to the area 1804. The area 1802 is an area setting numerical values and operators. The user selects corresponding buttons using the input interface 32 and can thereby set numerical values and operators. The area 1803 is an area for selecting a predefined measurement target item, and measurement target item names set for each measurement type (Direct Distance, ROI, and the like) are listed. The area 1804 displays the measurement item (Diameter and the like) corresponding to the measurement target item name selected by the user, and the user selects one of them.

The example in FIG. 18 is an example in which the user sets "0.1," "×," and "( )" in order in the area 1802, within the 0 selects AP-Length in the area 1803 and selects Diameter in the area 1804, then sets "+," "0.9," "×," and "( )" in order in the area 1802, and then within the 0 attempts to select "Commissure to Commissure" in the area 1803 and to select Diameter in the area 1804. By the Set button 1805 being selected, a new measurement item with the calculation rule defined in the area 1801 is set. It may be controlled such that the Set button 1805 cannot be selected before the calculation rule has been determined, or a warning may be displayed to the user. It may be controlled such that only measurement items with the same unit can be integrated as the calculation rule. It may be possible to define more advanced operators and functions (exponential functions, trigonometric functions, logarithmic functions, and the like) for the operators displayed in the area 1802.

Various specific examples as the processing at Step S103 have been described so far, but the above examples are only examples, and the embodiment is not limited to these examples. Any method is acceptable so long as it can set the calculation rule based on the grid point group. In this article, the processing at Step S103 is performed after Steps S101 and S102 for the sake of convenience, but if the setting at Step S103 has been performed in advance for a case of another or the same subject in the past, there is no need to newly set the calculation rule as Step S103, and it may be only necessary to read the previously set calculation rule.

A function that can output the set calculation rule may be included. A function that can input the calculation rule created by others or other facilities in advance and set the calculation rule may be included.

As described above, the setting function 354 sets the calculation rule for calculating the characteristic amount for the region of interest. The setting function 354 can make a change to the set calculation rule corresponding to a characteristic of a subject. For example, the setting function 354 acquires a change rule corresponding to the characteristic of the subject and changes the calculation rule using the acquired change rule. To give an example, the setting function 354 changes the set calculation rule based on the change rule set in accordance with the age and physical information (height and weight, for example) of the subject, features in the region of interest (a loss occurring, for example), treatment details for the subject, or the like.

The following describes an example of setting the change rule. The change rule is set for each set calculation rule and is stored in the storage circuitry 34 in association with the calculation rule. For example, the change rule changing a position to be measured in accordance with the age and physical information of the subject can be set. In such a case, for example, coordinate transformation information to make a change to coordinate information in the calculation rule is set as the change rule. To describe an example using FIG. 4, it is assumed that the calculation rule measuring, for example, the straight-line distance between P1 (0, 9) and P2 (0, 30) illustrated in FIG. 4 is set. To this calculation rule, for example, coordinate transformation information "P1+(0, 1)" is set as the change rule. This coordinate transformation information means that the coordinates of P1 in the calculation rule is changed to the coordinates (0, 10) with (0, 1) added to the coordinates. That is, the calculation rule after the application of the change rule is the rule measuring the straight-line distance between (0, 10) and P2 (0, 30). This coordinate transformation information is set by the user based on knowledge about the relation between age and physical information and the region of interest.

For example, it is also possible to set the change rule changing the measurement item in accordance with features in the region of interest or treatment details for the subject. In such a case, change information for changing the measurement item is set as the change rule. For example, it is assumed that the calculation rule measuring the volume of VOI is set. To this calculation rule, for example, the change information "volume→surface area" is set as the change rule. This change information means that the measurement item in the calculation rule is changed from "volume" to "surface area." That is, the calculation rule after the application of the change rule is the calculation rule measuring the surface area of VOI. This change information is set by the user based on knowledge about the relation between features in the region of interest or treatment details for the subject and the region of interest.

The change rule described above is only an example, and any other various changes can be freely set as the change rule for changing the calculation rule. When the change rule is set by the user, a GUI for changing is displayed.

As described above, upon setting the calculation rule for calculating the characteristic amount for the region of interest, the setting function 354 transmits the set calculation rule to the calculation function 355. The setting function 354 stores the calculation rule newly set in response to user operations in the storage circuitry 34. That is, the setting function 354 transmits the calculation rule and the calculation rule changed using the change rule to the calculation function 355 or stores them in the storage circuitry 34.

For example, the setting function 354 transmits information on the set Element (coordinate information based on the anatomical structure of the region of interest or an identifier such as a character string, ID, or Tag freely assigned to the coordinate information) and the measurement item to the calculation function 355 or stores them in the storage circuitry 34. The setting function 354 assigns an identifier to identify the calculation rule to each calculation rule and stores it in the storage circuitry 34.

The storage circuitry 34 stores therein the calculation rule set by the setting function 354. The storage circuitry 34 can classify and store therein a plurality of calculation rules based on a feature of the calculation rule. For example, the storage circuitry 34 stores therein a series of calculation rules used for a specific manipulation or a plurality of calculation rules used for the same subject each together. When the calculation rule changed using the change rule is included, the storage circuitry 34 stores therein the calculation rule and the calculation rule changed using the change rule together.

The above example describes a case in which the setting function 354 sets the calculation rule in response to user operations via the GUI. However, the setting function 354 can also set the calculation rule by reading the calculation rule already stored in the storage circuitry 34. For example, the setting function 354 acquires an identifier (information on the subject, information on the manipulation, or the like) for identifying the calculation rule and reads the calculation rule corresponding to the identifier desired to be acquired from the storage circuitry 34 to set the calculation rule. The identifier for identifying the calculation rule may be acquired, for example, from information input by the user.

Calculation Processing for Characteristic Amount

As described at Step S104 in FIG. 2, the calculation function 355 calculates the characteristic amount for the region of interest using the set calculation rule. Specifically, the calculation function 355 applies the Element and the measurement item set by the setting function 354 to the region of interest (the grid point group, for example) extracted by the extraction function 353 to calculate the characteristic amount in the region of interest.

The calculation function 355 can also be controlled to use the calculation rule appropriate for the manipulation. Specifically, the calculation function 355 acquires the calculation rule corresponding to a manipulation procedure and calculates the characteristic amount of the region of interest based on the acquired calculation rule. For example, the calculation function 355 reads the appropriate calculation rule from the storage circuitry 34 in line with each step or scene in a manipulation workflow and calculates the characteristic amount (measured value) in line with the read calculation rule.

In such a case, first, correspondence information associating each calculation rule with each step or scene in the manipulation workflow is stored in the storage circuitry 34. For example, for each step or scene in the manipulation workflow, identification information for identifying each is set. Then, based on operations by the user, correspondence information associating each calculation rule with the identification information is generated, and the generated correspondence information is stored in the storage circuitry 34. The calculation rule to be associated with the identification information is freely selected by the user.

The calculation function 355 identifies a workflow step or scene based on the identification information input by the user and reads the calculation rule associated with the identified workflow step or scene from the storage circuitry 34. The calculation function 355 then calculates the measured value for the region of interest based on the read calculation rule. For example, the user inputs the identification information corresponding to a series of steps included in the workflow in the order of implementation and performs a switching operation at a timing of the changeover of each step during the manipulation. The calculation function 355 reads the calculation rule corresponding to the identification information in the order of implementation in response to the switching operation and calculates the measured value based on the read calculation rule.

Once the characteristic amount (measured value) is calculated by the calculation function 355, the control function 351 performs various processing on the calculated measured value. For example, the control function 351 performs control to display the calculated measured value on the display 33. For example, the control function 351 can output the measured value to external apparatuses in CSV format or the like or output the measured value to other medical software (electronic medical records, reporting software, or the like) as digital information. For example, the control function 351 can also be controlled to automatically store the measured value in a hospital database (DB) or a storage device such as a hard disk drive (HDD) in a computer in which the medical image processing program according to the present embodiment is operating.

As described above, according to the first embodiment, the image acquisition function 352 acquires a medical image. The extraction function 353 extracts a region of interest from the medical image. The setting function 354 sets a calculation rule for calculating a characteristic amount for the region of interest. The storage circuitry 34 stores therein the calculation rule. Thus, the medical image processing apparatus 3 according to the first embodiment makes it possible to easily calculate a measured value of a new measurement item.

According to the first embodiment, the calculation function 355 calculates the characteristic amount of the region of interest based on the calculation rule. Thus, the medical image processing apparatus 3 according to the first embodiment makes it possible to automatically calculate a measured value based on any calculation rule set by the user even for an unregistered measurement item.

According to the first embodiment, the setting function 354 sets a rule for extracting anatomical information of the region of interest as the calculation rule for calculating the characteristic amount. Thus, the medical image processing apparatus 3 according to the first embodiment calculates the characteristic amount based on the set calculation rule to make it possible to calculate an anatomically meaningful measured value.

According to the first embodiment, the extraction function 353 extracts the region of interest as a grid point group in a certain format. The setting function 354 sets the calculation rule based on the grid point group. Thus, the medical image processing apparatus 3 according to the first embodiment can extract the region of interest with grid points in a preset format and makes it possible to extract each position of the region of interest as a position having anatomical meaning.

According to the first embodiment, the extraction function 353 extracts the region of interest based on anatomical characteristic points. The setting function 354 sets the calculation rule based on the anatomical characteristic points.

Thus, the medical image processing apparatus 3 according to the first embodiment makes it possible to extract each position of the region of interest as a position having anatomical meaning.

According to the first embodiment, the setting function 354 makes a change to the set calculation rule corresponding to a characteristic of a subject. Thus, the medical image processing apparatus 3 according to the first embodiment makes it possible to set the calculation rule more suitable for the subject.

According to the first embodiment, the storage circuitry 34 classifies and stores therein a plurality of calculation rules based on a feature of the calculation rule. Thus, the medical image processing apparatus 3 according to the first embodiment makes it possible to easily perform management of the calculation rule.

According to the first embodiment, the calculation function 355 acquires the calculation rule corresponding to a manipulation procedure and calculates the characteristic amount of the region of interest based on the acquired calculation rule. Thus, the medical image processing apparatus 3 according to the first embodiment makes it possible to automatically use the appropriate calculation rule in accordance with a situation.

According to the first embodiment, the control function 351 receives a figure element to be applied to the region of interest and a calculation item in the region of interest. The setting function 354 sets the calculation rule based on a combination of the figure element and the calculation item received by the control function 351. Thus, the medical image processing apparatus 3 according to the first embodiment makes it possible to easily set a new measurement item.

According to the first embodiment, the setting function 354 sets the calculation rule for calculating, as the characteristic amount for the region of interest, at least one of morphological information and property information of the region of interest. Thus, the medical image processing apparatus 3 according to the first embodiment makes it possible to calculate morphological and property features in the region of interest.

According to the first embodiment, the morphological information of the region of interest includes distance, area, volume, and angle in the region of interest. The property information of the region of interest includes the maximum value, minimum value, average value, variance value, and histogram of pixel values in a certain range in the region of interest. Thus, the medical image processing apparatus 3 according to the first embodiment makes it possible to calculate various features in the region of interest.

Second Embodiment

The second embodiment describes a medical system providing others with the calculation rule described in the first embodiment. As described in the first embodiment, the medical image processing apparatus according to the present application extracts each position in the region of interest as a position having anatomical meaning and sets the calculation rule using the extracted position. Unlike measurement based on absolute positional information (pixel and image density) of an image, measurement using this calculation rule can calculate a measured value having the same anatomical meaning no matter what shape the region of interest has. In addition, the medical image processing apparatus according to the present application can freely set the above calculation rule, and thus even when a new measurement item for the region of interest arises, the calculation rule for calculating the measured value of the measurement item can be easily set.

Figure 19:
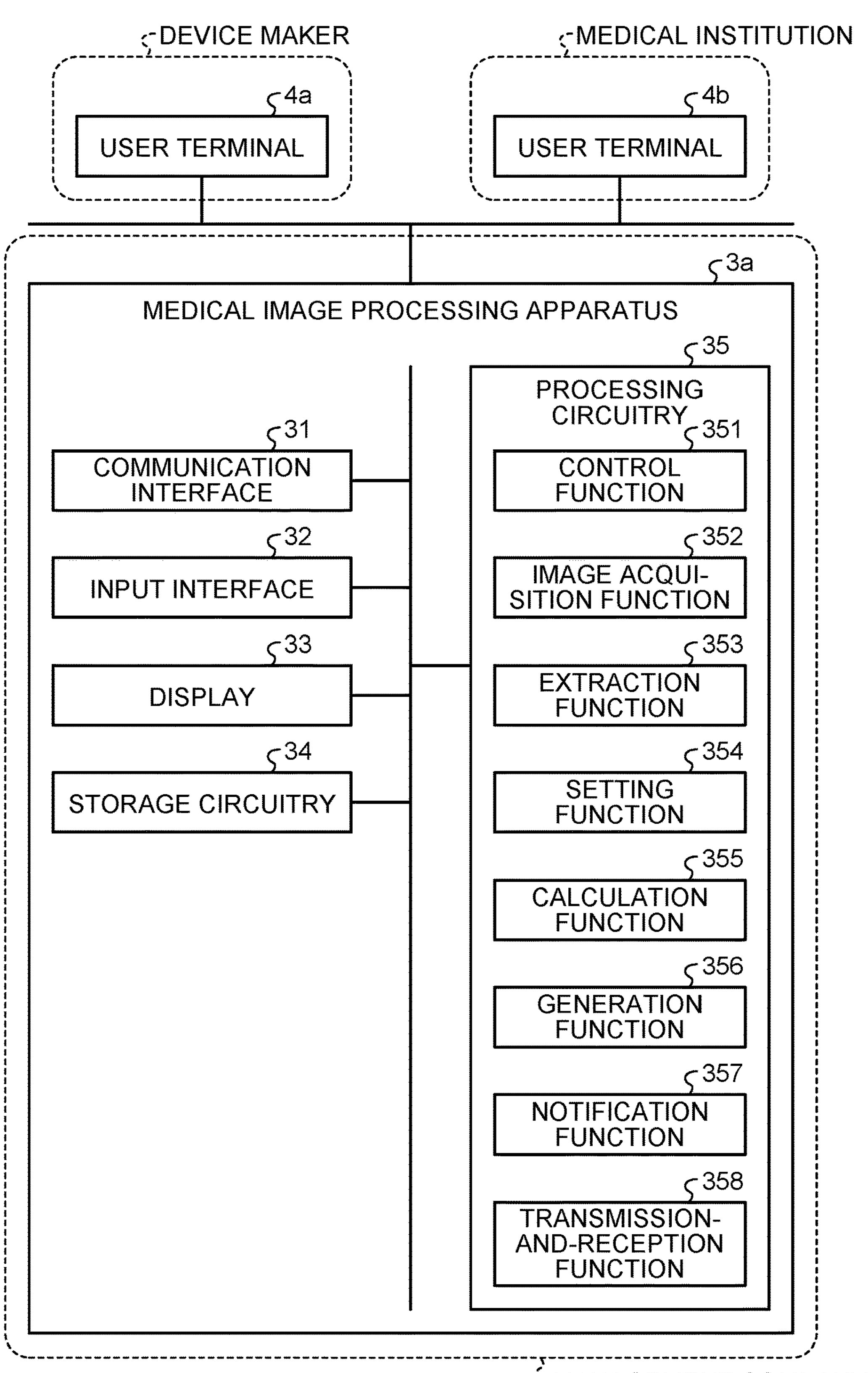
FIG. 19 is a diagram of a configuration example of a medical system according to a second embodiment.

Thus, the present embodiment describes a medical system providing services making such a calculation rule available to medical institutions and medical device makers. FIG. 19 is a diagram of a configuration example of the medical system according to the second embodiment. For example, as illustrated in FIG. 19, the medical system according to the present embodiment includes a medical image processing apparatus 3*a* installed in a management company, a user terminal 4*a* installed in a device maker, and a user terminal 4*b* installed in a medical institution, which are communicably connected to each other via a network. FIG. 19 illustrates only the medical image processing apparatus 3*a*, the user terminal 4*a*, and the user terminal 4*b*, but various other apparatuses and systems may be connected to the network. For example, an apparatus installed in an administrative agency or the like may be connected thereto.

The device maker is a company manufacturing and selling various medical devices and manages the user terminal 4*a*. The user terminal 4*a* incorporates the medical image processing program according to the first embodiment and can execute the various processing described in the first embodiment. That is, the user terminal 4*a* can execute the same processing as that by the medical image processing apparatus 3 according to the first embodiment.

The medical institution is, for example, a hospital or clinic and manages the user terminal 4*b*. The user terminal 4*b* incorporates the medical image processing program according to the first embodiment and can execute the various processing described in the first embodiment. That is, the user terminal 4*b* can execute the same processing as that by the medical image processing apparatus 3 according to the first embodiment.

The management company operates and manages the medical image processing apparatus 3*a* to manage provision of the calculation rule. Specifically, the management company contracts with the device maker and the medical institution to license the use of the medical image processing program according to the present application and to provide various services related to the use of the calculation rule.

For example, the medical image processing apparatus 3*a* differs from the medical image processing apparatus 3 according to the first embodiment in that it executes various functions for providing the calculation rule. Specifically, the medical image processing apparatus 3*a* differs in that it newly executes a generation function 356, a notification function 357, and a transmission-and-reception function 358 and in the processing details by the control function 351. The following describes mainly these points. FIG. 19 illustrates a case in which a single medical image processing apparatus 3*a* executes the various functions described in the first embodiment and various functions for the provision of the calculation rule, but the embodiment is not limited to this example, and an apparatus executing the various functions described in the first embodiment and an apparatus executing the various functions for the provision of the calculation rule may be separate from each other.

The control function 351 according to the second embodiment receives an update of information on a medical device. Specifically, the control function 351 acquires information on a new medical device and information on an existing device. The processing by the control function 351 will be described in detail below.

The generation function 356 generates notification information for a user terminal based on a timing when the control function 351 has received the update of the information on the medical device. Specifically, the generation function 356 generates notification information on the calculation rule for calculating a characteristic amount in a biological organ in which the medical device is involved. The processing by the generation function 356 will be described in detail below.

The notification function 357 provides notification of the notification information to the user terminal. Specifically, the notification function 357 provides notification of the notification information on the calculation rule to the user terminal. The processing by the notification function 357 will be described in detail below.

The transmission-and-reception function 358 transmits and receives information on the calculation rule to and from the user terminal **4*b*. Specifically, the transmission-and-reception function 358 receives request information for the calculation rule corresponding to acquisition of a new medical device and, based on the request information, transmits an update program on the calculation rule for calculating the characteristic amount in the biological organ in which the medical device is involved to the user terminal 4*b*. The processing by the transmission-and-reception function 358** will be described in detail below.

Figure 20:
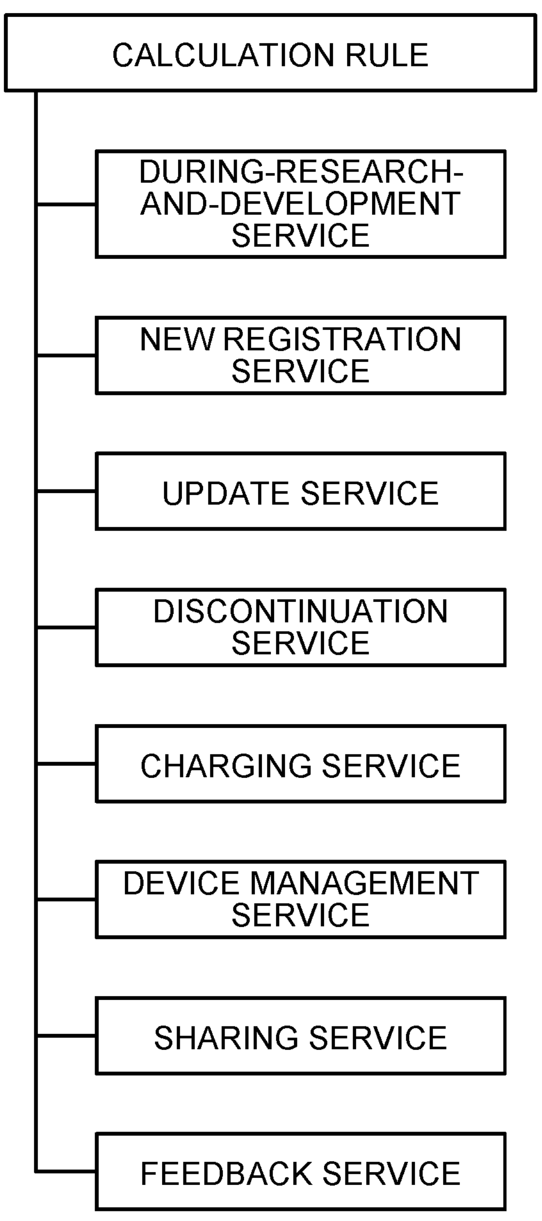
FIG. 20 is a diagram of an example of provided services according to the second embodiment.

The medical image processing apparatus **3*a* according to the second embodiment provides, under operation and management by the management company, a "during-research-and-development service," a "new registration service," an "update service," a "discontinuation service," a "charging service," a "device management service," a "sharing service," and a "Feedback service," for example, illustrated in FIG. 20 to the device maker and the medical institution by the functions described above. FIG. 20** is a diagram of an example of provided services according to the second embodiment.

During-Research-and-Development Service

The during-research-and-development service is a service provided to the device maker and is a service licensing free use of the medical image processing program. That is, the device maker having received provision of the during-research-and-development service can develop new devices and freely set the calculation rule for the developed devices using the user terminal **4*a*. The control function 351 of the medical image processing apparatus 3*a* can also be controlled to provide new functions, improved functions, and the like of the apparatus to the user terminal 4*a*** while providing the during-research-and-development service.

For example, the storage circuitry 34 stores therein information on the device maker signing a contract for the during-research-and-development service (identification information of the device maker, contract details, an address to and from which information is transmitted and received, or the like). The control function 351 licenses free use of the medical image processing program based on the information on the device maker stored in storage circuitry 34. For example, based on the identification information of the device maker, the control function 351 approves a use request for the calculation rule stored in the storage circuitry 34 from the device maker and permits free access to the calculation rule. The notification function 357 provides notification of new functions, improved functions, and the like of the apparatus to the user terminal **4*a*** of the device maker signing the contract for the during-research-and-development service.

The during-research-and-development service may be provided free of charge, provided that the calculation rule set by the device maker is provided to the management company. That is, the management company provides the medical image processing program free of charge in exchange for the calculation rule adapted to medical devices developed by the device maker on its own.

New Registration Service

The new registration service is a service to be provided to the medical institution and provides the calculation rule adapted to a new device to the medical institution having been licensed to use the medical image processing program. For example, the control function 351 acquires information on a new medical device from the device maker and the calculation rule adapted to the medical device. The generation function 356 generates notification information including the acquired information on the medical device and the information on the calculation rule. The notification function 357 provides notification of the notification information generated by the generation function 356 to the user terminal **4*b* of the medical institution. The notification function 357 provides notification of the notification information making it possible to download a file of the calculation rule to the user terminal 4*b*. That is, the notification function 357** provides the notification information such that users in the medical institution can view the notification information and download and use the calculation rule for which notification has been provided.

The notification information may be provided in accordance with permission and approval of the medical device. That is, the control function 351 acquires information on permission and approval of the medical device, and the generation function 356 generates notification information for the user terminal **4*b* at a timing when the medical device has been permitted and approved. To give an example, the control function 351 acquires information on the medical device having been approved or information on the medical device having been covered by insurance. The generation function 356 generates the notification information at a timing when the medical device has been approved or when the medical device has been covered by insurance. The control function 351** may acquire the information on permission and approval of the medical device in response to an input operation by the user or acquire the information from an external apparatus via a network.

The transmission-and-reception function 358 receives request information on acquisition of the new medical device from the user terminal **4*b* and transmits the calculation rule corresponding to the received request to the user terminal 4*b*. For example, the transmission-and-reception function 358 transmits the file of the calculation rule to the user terminal 4*b* in response to a request to download the calculation rule from the user terminal 4*b*** having received the notification information.

Figure 21:
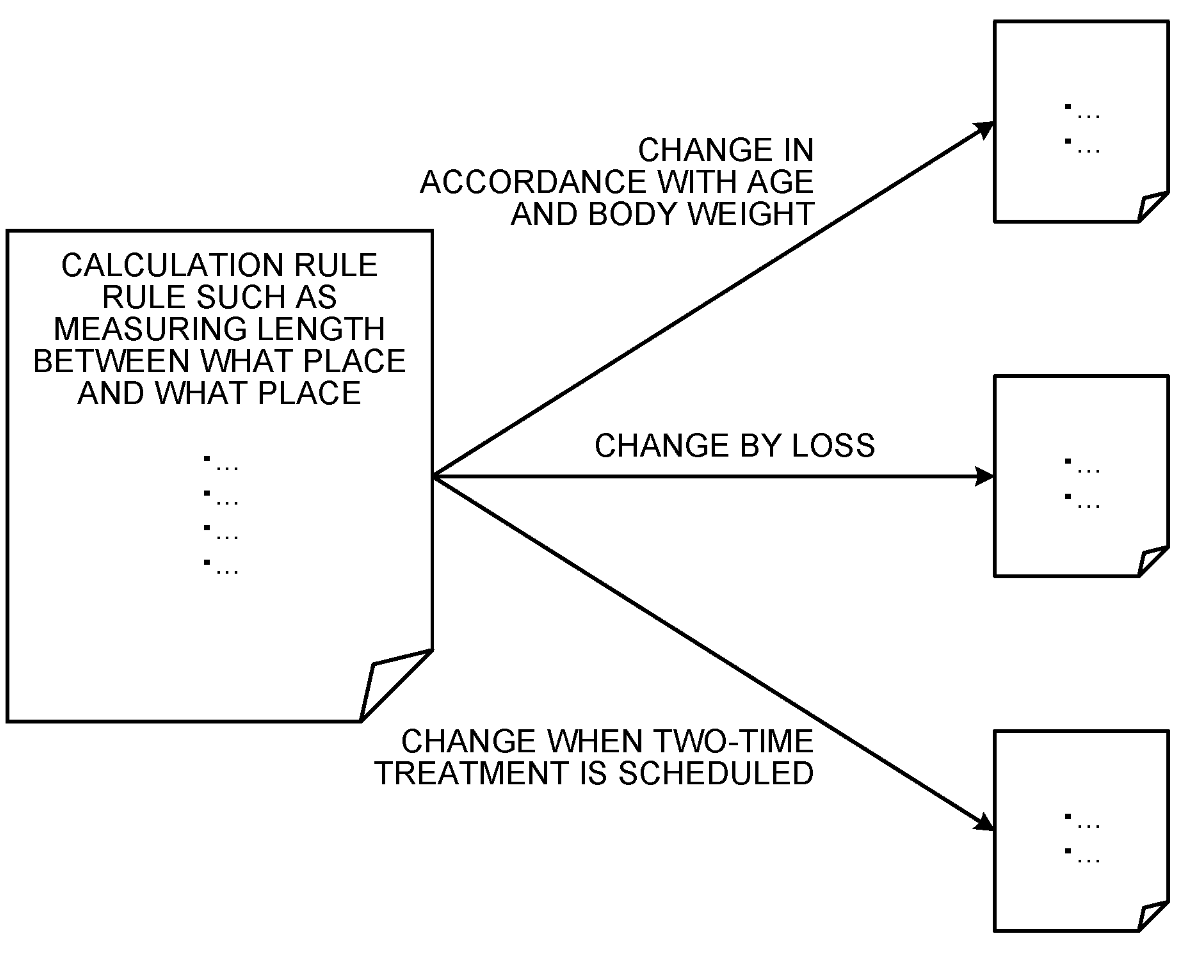
FIG. 21 is a diagram for illustrating an example of the calculation rule to be provided to a user terminal according to the second embodiment.
Figure 22:
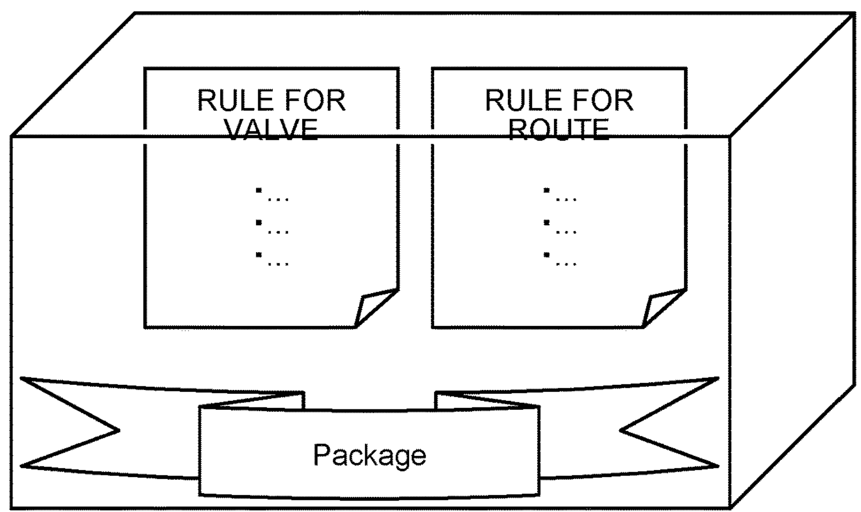
FIG. 22 is a diagram for illustrating an example of the calculation rule to be provided to a user terminal according to the second embodiment.
Figure 22:
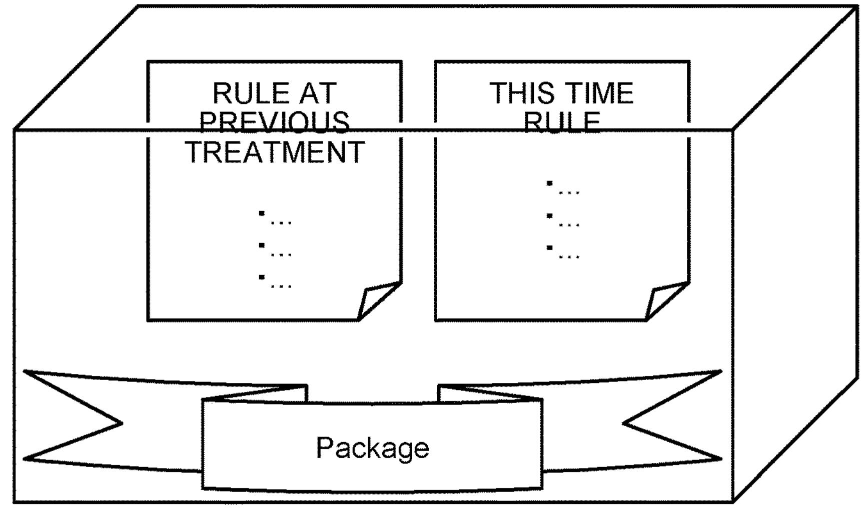
Figure 22:
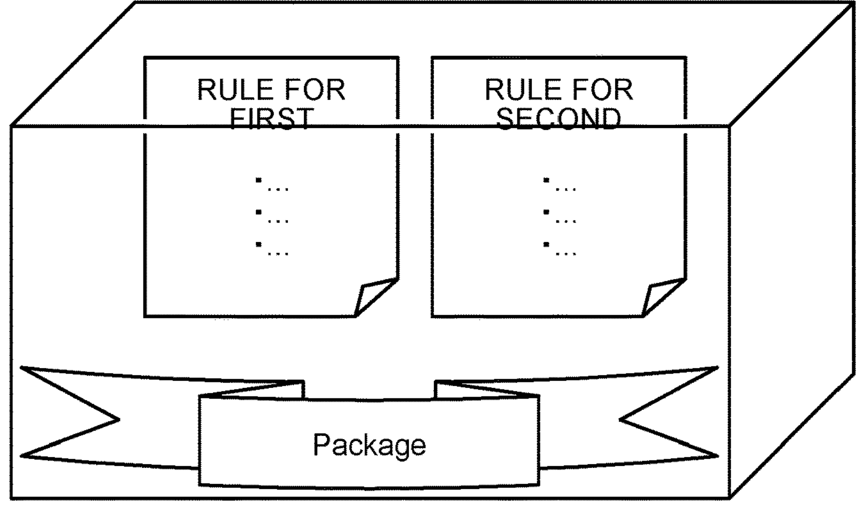
Figure 23:
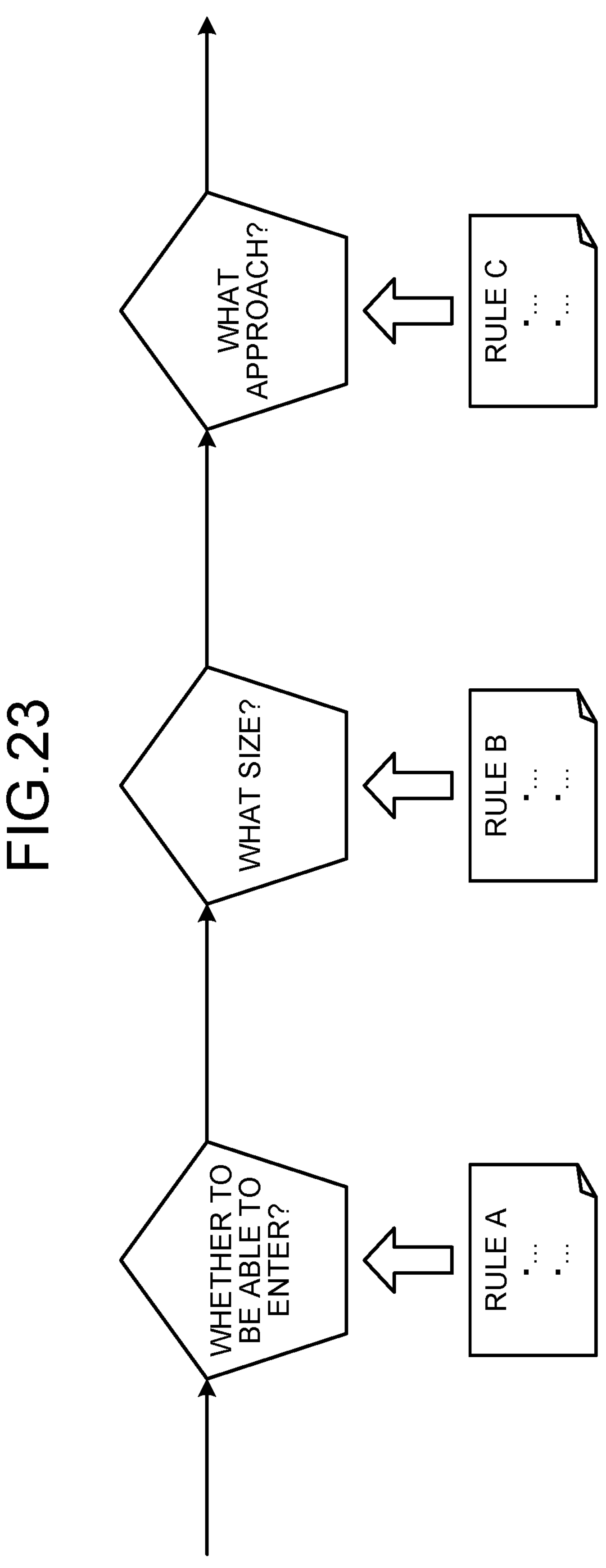
FIG. 23 is a diagram for illustrating an example of the calculation rule to be provided to a user terminal according to the second embodiment.

The transmission-and-reception function 358 can provide the calculation rule to the user terminal **4*b* in the various forms described in the first embodiment. FIG. 21 to FIG. 23 are diagrams for illustrating examples of the calculation rule to be provided to the user terminal 4*b*** according to the second embodiment.

For example, the transmission-and-reception function 358 transmits the calculation rule and the calculation rule changed using the change rule to the user terminal **4*b*. To give an example, as illustrated in FIG. 21, the transmission-and-reception function 358 transmits an original calculation rule "such as measuring length between what place and what place," a derived calculation rule obtained by changing the original calculation rule in accordance with age and body weight, a derived calculation rule obtained by changing the original calculation rule by a loss in the region of interest, and a derived calculation rule obtained by changing the original calculation rule in accordance with a schedule of two-time treatment together to the user terminal 4***b*.

For example, the transmission-and-reception function 358 transmits a plurality of calculation rules classified based on the feature of the calculation rules to the user terminal 4*b*. To give an example, as illustrated in FIG. 22, the transmission-and-reception function 358 transmits the calculation rule as a package of a "rule for valve" and a "rule for route" to the user terminal 4*b*.

For example, the transmission-and-reception function 358 transmits a plurality of calculation rules assigned to each step or scene in the manipulation workflow to the user terminal 4*b*. To give an example, as illustrated in FIG. 23, the transmission-and-reception function 358 transmits the calculation rule including Rule A assigned to "Whether to be able to enter?," Rule B assigned to "What size?," and Rule C assigned to "What approach?" to the user terminal 4*b*.

Rule A includes, for example, the calculation rule calculating length and area for determining whether the medical device can enter the body. Rule B includes, for example, the calculation rule calculating a measured value for selecting the medical device to be indwelled in the body. Rule C includes the calculation rule for measuring a site (an aorta, a hand, a foot, or an abdomen, for example) through which the medical device passes before reaching the region of interest.

The new registration service may perform charging in accordance with permission and approval of a new medical device. For example, the calculation rule may be provided free of charge before the new medical device is approved or covered by insurance, and the calculation rule may be provided for a fee after the new medical device is approved or covered by insurance. In this case, for example, the timing of permission and approval differs from country to country, and thus the details of the provided service will vary in accordance with the status of permission and approval from country to country.

Update Service

The update service is a service to be provided to the medical institution and provides the calculation rule changed in accordance with a change of the existing device to the medical institution having been licensed to use the medical image processing program. For example, the control function 351 acquires from the device maker information on the change of the medical device and the calculation rule changed in order to adapt to the medical device. The generation function 356 generates notification information including the acquired information on the change of the medical device and the information on the changed calculation rule. The notification function 357 provides notification of the notification information generated by the generation function 356 to the user terminal 4*b* of the medical institution. The notification function 357 provides notification of the notification information making it possible to download a file of the calculation rule to the user terminal 4*b*.

For example, the control function 351 acquires information on an update of at least one of a specification and a price of the medical device and a method of use and a guideline for the medical device, and the generation function 356 generates notification information for the user terminal 4*b* at a timing when at least one of the specification and the price of the medical device and the method of use and the guideline for the medical device has been updated. When the calculation rule is not changed, the generation function 356 generates notification information including information indicating that there is no change to the calculation rule.

The transmission-and-reception function 358 receives from the user terminal 4*b* request information on acquisition of the changed calculation rule corresponding to the changed medical device and transmits the changed calculation rule corresponding to the received request to the user terminal 4*b*. For example, the transmission-and-reception function 358 transmits a file of the changed calculation rule to the user terminal 4*b* in response to a request to download the calculation rule from the user terminal 4*b* having received the notification information.

If the calculation rule based on the change rule is associated with the calculation rule changed in accordance with the change of the medical device, the transmission-and-reception function 358 transmits, together with the calculation rule changed in accordance with the change of the medical device, the calculation rule obtained by changing the calculation rule based on the change rule together.

FIG. 24 is a diagram for illustrating an example of a change of the calculation rule according to the second embodiment. FIG. 24 illustrates changes to the derived calculation rules when a change occurs in the original calculation rule in FIG. 21. For example, if a change occurs in the original calculation rule in FIG. 21, as illustrated in FIG. 24, the setting function 354 applies the change rule described in FIG. 21 to the changed calculation rule, thereby making a change to the derived calculation rules each. The transmission-and-reception function 358 transmits the changed calculation rule and the changed derived calculation rules altogether to the user terminal 4*b*.

Discontinuation Service

The discontinuation service is a service to be provided to the medical institution and provides information on a discontinued device to the medical institution having been licensed to use the medical image processing program. For example, the control function 351 acquires information on discontinuation of the medical device from the device maker. The generation function 356 generates notification information for the user terminal 4*b* at a timing when the medical device has been discontinued. That is, the generation function 356 generates the notification information including the acquired information on discontinuation of the medical device. The notification function 357 provides notification of the notification information generated by the generation function 356 to the user terminal 4*b* of the medical institution.

The generation function 356 can generate the notification information including information on deletion of the calculation rule corresponding to the discontinued device. For example, the generation function 356 generates the notification information inquiring whether the calculation rule corresponding to the discontinued device may be deleted. When information to the effect that the calculation rule may be deleted is acquired from the user terminal 4*b*, the license to use the calculation rule in the contract between the management company and the medical institution is deleted.

Charging Service

The charging service is a service to be provided to the medical institution and provides various charging services to the medical institution having been licensed to use the medical image processing program. For example, the control function 351 can provide the charging service charging a fixed fee at a point in time of incorporating the medical image processing program and making subsequent downloads of the measurement rule free of charge. For example, the control function 351 can provide the charging service making a charge each time the measurement rule is downloaded. For example, the control function 351 can perform the charging service that is provided free of charge until a certain period of time elapses or until a certain number of calculation rules are downloaded and then makes a charge from a point in time when these are exceeded. For example, the control function 351 can perform the charging service providing use for a fixed period of time (one year, for example) at a fixed fee.

Figure 25A:
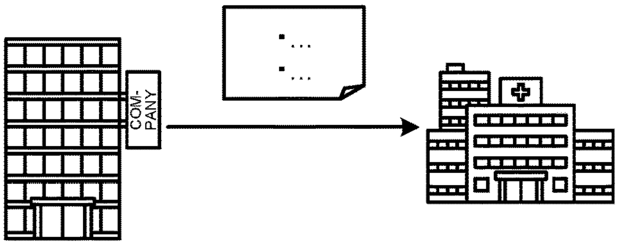
FIG. 25A is a diagram of an example of a charging service according to the second embodiment.

For example, as illustrated in FIG. 25A, the control function 351 can also provide the charging service that distributes the updated calculation rule monthly or makes it freely downloadable during a contract period. FIG. 25A is a diagram of an example of the charging service according to the second embodiment.

Device Management Service

The device management service is a service to be provided to the medical institution and is a service managing, for the medical institution having been licensed to use the medical image processing program, information on the medical device employed by the medical institution. For example, the control function 351 creates a list of medical devices employed by the user terminal 4*b* based on a download history of the calculation rule received from the user terminal 4*b* and stores the list in the storage circuitry 34. The control function 351 then updates the list of the medical devices based on information on addition of new medical devices or discontinuation of medical devices.

By using this list, the notification function 357 enables control to, when providing notification of an update of the medical device, provide notification of information on the update only to the user terminal 4*b* of the medical institution employing the updated medical device.

Sharing Service

The sharing service is a service to be provided to the medical institution and is a service enabling the medical institution having been licensed to use the medical image processing program to provide the calculation rule created in the medical institution to another medical institution. To achieve this service, the management company first authorizes new creation of the calculation rule and modification of the downloaded calculation rule in the user terminal 4*b* of the medical institution. On top of that, the management company provides the following sharing service. For example, the management company provides the sharing service authorizing the sharing of the calculation rule among medical institutions. That is, the management company provides the sharing service to allow medical institutions to share the calculation rule without the management company interposed therebetween (without acquiring authentication from the management company).

The management company can also provide the sharing service that authenticates and then shares the calculation rule created by the medical institution. Specifically, the transmission-and-reception function 358 receives the calculation rule for calculating the characteristic amount in the biological organ in which the medical device is involved from a first user terminal. The transmission-and-reception function 358 then transmits the calculation rule to a second user terminal based on an authentication result of the calculation rule.

Figure 25B:
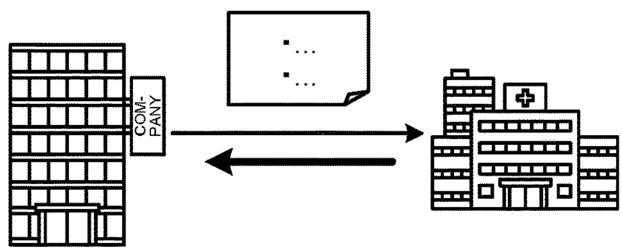
FIG. 25B is a diagram for illustrating authentication in a sharing service according to the second embodiment.
Figure 25C:
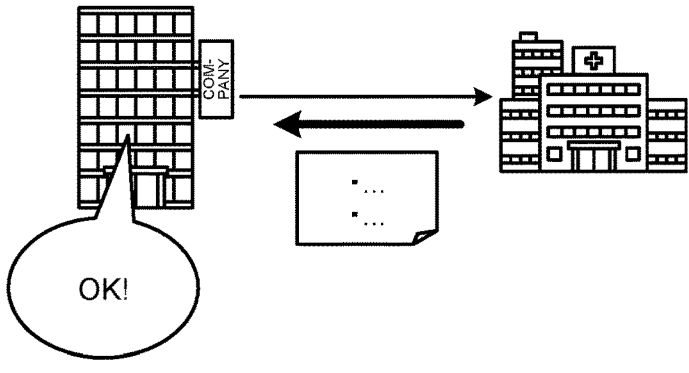
FIG. 25C is a diagram for illustrating the authentication in the sharing service according to the second embodiment.

For example, as illustrated in FIG. 25B, the transmission-and-reception function 358 receives notification of the number of times the calculation rule has been used (the number of subjects and the number of times used) and upload of a definition file of the calculation rule created by the medical institution. The management company then authenticates the uploaded file based on the received details as illustrated in FIG. 25C. The calculation rule authenticated by the management company becomes a file that can be shared. For example, the transmission-and-reception function 358 transmits information to the effect that the file has been authenticated to the medical institution having uploaded the file. The transmission-and-reception function 358 then transmits the uploaded calculation rule to the user terminal 4*b* of the other medical institution. This processing enables the medical institution to share the calculation rule created on its own with the other medical institution. The authentication of the calculation rule is not limited to the management company but may also be performed by the device maker.

Feedback Service

The Feedback service is a service to be provided to the medical institution and is a service providing the usage of the calculation rule at various medical institutions to the medical institution having been licensed to use the medical image processing program. Specifically, the transmission-and-reception function 358 receives from a plurality of user terminals respective use histories of the calculation rule for calculating the characteristic amount in the biological organ in which the medical device is involved. The transmission-and-reception function 358 then transmits use history information obtained by integrating the use histories to the user terminals.

Figure 26:
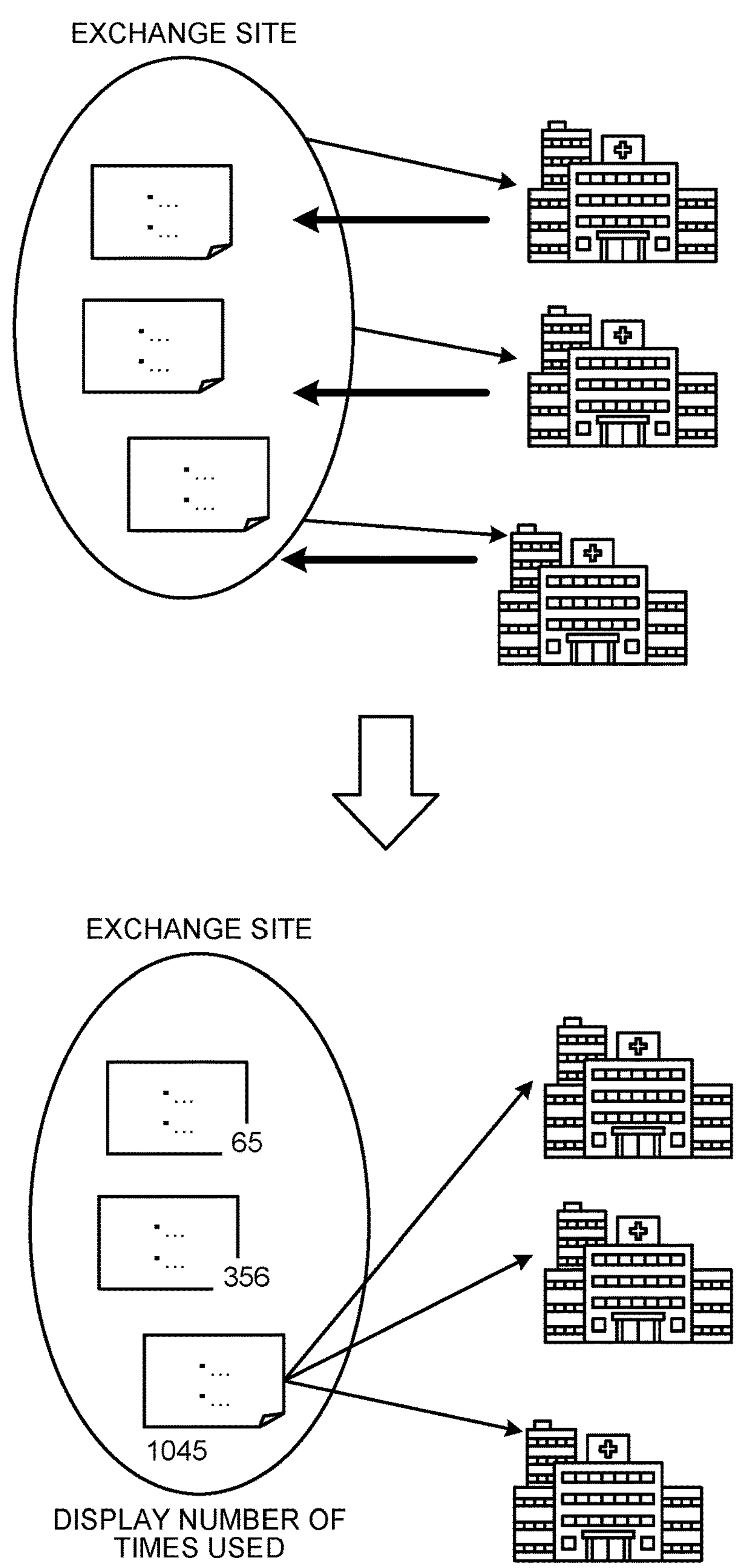
FIG. 26 is a diagram of an example of a Feedback service according to the second embodiment.

For example, the transmission-and-reception function 358 receives notification of the number of times the calculation rule has been used (the number of subjects and the number of times used) from the user terminal 4*b* of each medical institution. The transmission-and-reception function 358 then calculates the total number of the number of times used for each type of the calculation rule and transmits the calculated total number to the user terminal 4*b* of each medical institution. In such a case, for example, as illustrated in FIG. 26, the management company operates an exchange site providing the number of times used of the calculation rule and provides the total value of the number of times used for each type of the calculation rule by the exchange site. For example, the transmission-and-reception function 358 can also be controlled to display the number of times used on a download screen for the calculation rule. The information fed back from the medical institution is not limited to the number of times used but may also include, for example, actual results on use (information on whether the calculation rule was appropriate or the like). FIG. 26 is a diagram of an example of the Feedback service according to the second embodiment.

As described above, according to the second embodiment, the control function 351 receives an update of information on a medical device. The generation function 356 generates notification information for a user terminal based on a timing of the update. The notification function 357 provides notification of the notification information to the user terminal. Thus, the medical system according to the second embodiment can provide notification to the user terminal in response to the update of the information on the medical device, makes it possible to immediately respond to a case in which a new measurement item related to the medical device arises, and makes it possible to easily calculate a measured value of the new measurement item.

According to the second embodiment, the control function 351 acquires information on permission and approval of the medical device. The generation function 356 generates notification information for the user terminal at a timing when the medical device has been permitted and approved. Thus, the medical system according to the second embodiment makes it possible to provide notification of the information on the condition that the medical device has been permitted and approved.

According to the second embodiment, the control function 351 acquires information on an update of at least one of a specification and a price of the medical device and a method of use and a guideline for the medical device The generation function 356 generates notification information for the user terminal at a timing when at least one of the specification and the price of the medical device and the method of use and the guideline for the medical device has been updated. Thus, the medical system according to the second embodiment makes it possible to respond to various updates for the medical device.

According to the second embodiment, the control function 351 acquires information on discontinuation of the medical device. The generation function 356 generates notification information for the user terminal at a timing when the medical device has been discontinued. Thus, the medical system according to the second embodiment makes it possible to provide information on the medical device having been discontinued to the user.

According to the second embodiment, the generation function 356 generates notification information on the calculation rule for calculating the characteristic amount in the biological organ in which the medical device is involved. The notification function 357 provides notification of the notification information on the calculation rule to the user terminal. Thus, the medical system according to the second embodiment makes it possible to provide notification of the calculation rule.

According to the second embodiment, the transmission-and-reception function 358 receives request information on purchase and acquisition of the medical device from the user terminal. The transmission-and-reception function 358 transmits an update program on the calculation rule for calculating the characteristic amount in the biological organ in which the medical device is involved to the user terminal based on the request information. Thus, the medical system according to the second embodiment makes it possible to provide the updated calculation rule to the user terminal.

According to the second embodiment, the transmission-and-reception function 358 receives the calculation rule for calculating the characteristic amount in the biological organ in which the medical device is involved from a first user terminal. The transmission-and-reception function 358 transmits the calculation rule to a second user terminal based on an authentication result of the calculation rule. Thus, the medical system according to the second embodiment makes it possible to share the calculation rule received from the user with other users.

According to the second embodiment, the transmission-and-reception function 358 receives from a plurality of user terminals respective use histories of the calculation rule for calculating the characteristic amount in the biological organ in which the medical device is involved. The transmission-and-reception function 358 transmits use history information obtained by integrating the use histories to the user terminals. Thus, the medical system according to the second embodiment makes it possible to provide the calculation rule with actual results on use taken into account to the user.

OTHER EMBODIMENTS

The embodiments described above have been described an example in which a reception unit, an acquisition unit, an extraction unit, a setting unit, a calculation unit, a generation unit, a notification unit, a reception unit, and a transmission unit in the present specification are implemented by the control function, the image acquisition function, the extraction function, the setting function, the calculation function, the generation function, the notification function, and the transmission-and-reception function, respectively, of the processing circuitry, but the embodiment is not limited to this example. For example, apart from implementing the reception unit, the acquisition unit, the extraction unit, the setting unit, the calculation unit, the generation unit, the notification unit, the reception unit, and the transmission unit in the present specification by the control function, the image acquisition function, the extraction function, the setting function, the calculation function, the generation function, the notification function, and the transmission-and-reception function described in the embodiments, those functions may be implemented by hardware alone, software alone, or a combination of hardware and software.

The term "processor" used in the description of the embodiments described above means, for example, a circuit such as a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). In place of storing the computer program in the storage circuitry, the computer program may directly be embedded in the circuitry of the processor. In this case, the processor reads the computer program embedded in the circuitry and executes it to implement its function. Each processor of the present embodiment is not limited to being configured as a single circuit for each processor but may also be configured as one processor by combining a plurality of independent circuits to implement its functions.

The medical image processing program to be executed by the processor is provided embedded in advance in a read only memory (ROM), storage circuitry, or the like. This medical image processing program may be provided recorded in a computer-readable, non-transitory storage medium such as a compact disc (CD)-ROM, a flexible disk (FD), a CD-recordable (R), or a digital versatile disc (DVD) in a file of a format installable to or a format executable by these apparatuses. This medical image processing program may also be stored on a computer connected to a network such as the Internet and provided or distributed by being downloaded over the network. For example, this medical image processing program includes a module including each processing function described above. As actual hardware, a CPU reads the medical image processing program from a storage medium such as a ROM and executes it, and thereby each module is loaded onto a main memory and generated on the main memory.

In the embodiments and modifications described above, the illustrated components of each apparatus are functionally conceptual ones and do not necessarily need to be physically configured as illustrated in the drawing. That is to say, the specific form of the dispersion or integration of each apparatus is not limited to the one illustrated in the drawing, but the whole or part thereof can be configured in a functionally or physically distributed or integrated manner in any unit in accordance with various kinds of loads, use conditions, and the like. Further, the whole or any part of the processing functions performed by each apparatus can be implemented by a CPU and a computer program that is analyzed and executed by the CPU or be implemented as hardware by wired logic.

Of the processing described in the embodiments and modifications described above, the whole or part of the processing described as being performed automatically can be performed manually, or the whole or part of the processing described as being performed manually can be performed automatically by known methods. In addition, information including processing procedures, control procedures, specific names, and various data and parameters described in the above document and drawings can be changed as desired, except as specified.

At least one of the embodiments described above can easily calculate a measured value of a new measurement item.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
processing circuitry configured to
acquire a medical image,
extract, from the medical image, a particular region of interest as a grid point group having a number of grid points and a grid point arrangement specified for each type of a region of interest, and
set a calculation rule for calculating a characteristic amount for the extracted region of interest based on the grid point group; and
storage circuitry configured to store therein the calculation rule.

2. The medical image processing apparatus according to claim 1, wherein the processing circuitry is further configured to calculate a characteristic amount of the extracted region of interest based on the calculation rule.

3. The medical image processing apparatus according to claim 2, wherein the processing circuitry is further configured to acquire the calculation rule corresponding to a manipulation procedure and calculate the characteristic amount of the extracted region of interest based on the acquired calculation rule.

4. The medical image processing apparatus according to claim 1, wherein the processing circuitry is further configured to set a rule for extracting anatomical information of the extracted region of interest as the calculation rule for calculating the characteristic amount.

5. The medical image processing apparatus according to claim 4, wherein the processing circuitry is further configured to:
extract the particular region of interest based on anatomical characteristic points, and set the calculation rule based on the anatomical characteristic points.

6. The medical image processing apparatus according to claim 1, wherein the processing circuitry is further configured to make a change to the set calculation rule corresponding to a characteristic of a subject.

7. The medical image processing apparatus according to claim 1, wherein the storage circuitry is further configured to classify and store therein a plurality of the calculation rules based on a feature of the calculation rule.

8. The medical image processing apparatus according to claim 1, wherein
the processing circuitry is further configured to receive a figure element to be applied to the extracted region of interest and a calculation item in the extracted region of interest, and
the processing circuitry is further configured to set the calculation rule based on a combination of the figure element and the calculation item received.

9. The medical image processing apparatus according to claim 1, wherein the processing circuitry is further configured to set the calculation rule for calculating, as the characteristic amount for the region of interest, at least one of morphological information and property information of the extracted region of interest.

10. The medical image processing device according to claim 9, wherein
the morphological information of the extracted region of interest includes a distance, an area, a volume, and an angle in the extracted region of interest, and
the property information of the region of interest includes a maximum value, a minimum value, an average value, a variance value, and a histogram of pixel values in a certain range in the extracted region of interest.

11. A method for processing a medical image, the method comprising:
acquiring a medical image;
extracting, from the medical image, a particular region of interest as a grid point group having a number of grid points and a grid point arrangement specified for each type of a region of interest;
setting a calculation rule for calculating a characteristic amount for the extracted region of interest based on the grid point group; and
storing the calculation rule in storage circuitry.

* * * * *